(12) United States Patent
Briard et al.

(10) Patent No.: US 8,093,406 B2
(45) Date of Patent: Jan. 10, 2012

(54) CYCLIC SULFONES WITH AMINOBENZYL SUBSTITUTION USEFUL AS BACE INHIBITORS

(75) Inventors: Emmanuelle Briard, Huningue (FR);
Rainer Martin Lueoend, Therwil (CH);
Rainer Machauer, Freiburg (DE);
Henrik Moebitz, Freiburg (DE); Olivier Rogel, Hésingue (FR); Jean-Michel Rondeau, Rixheim (FR); Heinrich Rueeger, Flueh (CH); Marina Tintelnot-Blomley, Maulburg (DE);
Siem Jacob Veenstra, Lörrach (DE)

(73) Assignee: Novartis AG, Basel (CH)

( * ) Notice: Subject to any disclaimer, the term of this patent is extended or adjusted under 35 U.S.C. 154(b) by 62 days.

(21) Appl. No.: 12/500,093

(22) Filed: Jul. 9, 2009

(65) Prior Publication Data

US 2010/0056490 A1    Mar. 4, 2010

Related U.S. Application Data

(60) Provisional application No. 61/154,573, filed on Feb. 23, 2009.

(30) Foreign Application Priority Data

Jul. 10, 2008    (EP) .................................... 08160123

(51) Int. Cl.
*C07D 335/02*    (2006.01)

(52) U.S. Cl. ................ 549/28; 549/13; 549/1; 514/432; 514/430; 514/183

(58) Field of Classification Search .................. None
See application file for complete search history.

(56) References Cited

U.S. PATENT DOCUMENTS

| | | | | |
|---|---|---|---|---|
| 4,535,163 | A | * | 8/1985 | Sach .............................. 546/300 |
| 2004/0198832 | A1 | * | 10/2004 | Szarek et al. .................. 514/599 |
| 2009/0054427 | A1 | * | 2/2009 | Briard et al. ................ 514/231.5 |
| 2009/0099207 | A1 | * | 4/2009 | Rueeger et al. ............... 514/256 |

FOREIGN PATENT DOCUMENTS

WO    WO 2007/093621 A1    8/2007

OTHER PUBLICATIONS

John Varghese et al., "Human â-Secretase (BACE) and BACE Inhibitors", Journal of Medicinal Chemistry, 2003 vol. 46 No. 22 pp. 4625-4630.

\* cited by examiner

*Primary Examiner* — Anish Gupta
*Assistant Examiner* — Theodore R West

(57) ABSTRACT

The invention relates to novel heterocyclic compounds of the formula

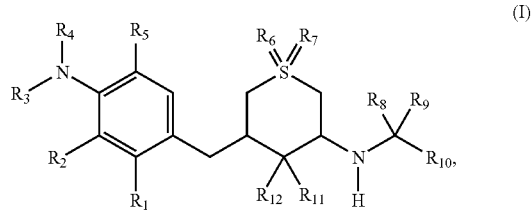

(I)

in which all of the variables are as defined in the specification, in free form or in salt form, to their preparation, to their use as medicaments and to medicaments comprising them.

7 Claims, No Drawings

CYCLIC SULFONES WITH AMINOBENZYL SUBSTITUTION USEFUL AS BACE INHIBITORS

This application claims benefit under 35 U.S.C. §119(e) of U.S. Provisional Application No. 61/076,462, filed Jun. 27, 2008, and benefit under 35 U.S.C. §119(a)-(d) or (f) or 365(b) of EP Application No. 08160123.9, filed Jul. 10, 2008, the contents of which are incorporated herein by reference in their entirety.

The present invention relates to novel heterocyclic compounds, to their preparation, to their use as medicaments and to medicaments comprising them.

More particularly, the invention relates to a compound of the formula

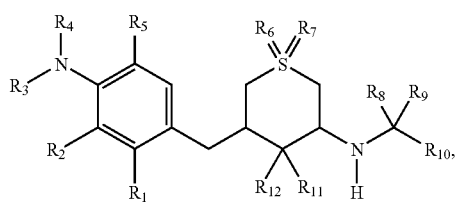

in which $R_1$ is hydrogen; halogen; or $(C_{1-8})$alkyl;

$R_2$ is hydrogen; halogen; $(C_{1-8})$alkyl; halogen-$(C_{1-8})$alkyl; $(C_{1-8})$alkoxy; or halogen-$(C_{1-8})$alkoxy;

either $R_3$ is hydrogen; and $R_4$ is hydrogen; $(C_{1-8})$alkoxy-$(C_{1-8})$alkyl; $(C_{1-8})$alkylcarbonyloxy-$(C_{1-8})$alkyl; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; N—$(C_{3-8})$cycloalkylamino-$(C_{1-8})$alkyl; formyl; $(C_{1-8})$alkylcarbonyl; $(C_{1-8})$alkoxy-$(C_{1-8})$alkylcarbonyl; amino-$(C_{1-8})$alkylcarbonyl; N—$(C_{1-8})$alkylamino-$(C_{1-8})$alkylcarbonyl; N,N-di-[$(C_{1-8})$alkyl]amino-$(C_{1-8})$alkylcarbonyl with two identical or different $(C_{1-8})$alkyl moieties in the N,N-di-[$(C_{1-8})$alkyl]amino moiety, which two $(C_{1-8})$alkyl moieties, taken together, can complete, together with the nitrogen atom, to which they are attached, a ring with 3 to 7 ring members; N—$(C_{3-8})$cycloalkylamino-$(C_{1-8})$alkylcarbonyl; or $(C_{1-8})$alkoxycarbonyl;

or $R_3$ is halogen-$(C_{1-8})$alkyl; hydroxy-$(C_{1-8})$alkyl; $(C_{1-8})$alkoxy-$(C_{1-8})$alkyl; formyl; $(C_{1-8})$-alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; $(C_{1-8})$alkoxycarbonyl; halogen-$(C_{1-8})$alkoxycarbonyl; or an aryl-$(C_{1-8})$alkyl group, which aryl-$(C_{1-6})$alkyl group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$-alkoxy; and $R_4$ is hydrogen; $(C_{1-8})$alkyl; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl;

$R_5$ is hydrogen; halogen; $(C_{1-8})$alkyl; halogen-$(C_{1-6})$alkyl; halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; $(C_{2-8})$alkenyl; $(C_{3-8})$cycloalkyl-$(C_{2-8})$alkenyl; halogen-$(C_{2-8})$alkenyl; $(C_{1-8})$alkoxy; halogen-$(C_{1-8})$alkoxy; halogen-$(C_{1-8})$alkoxy substituted by hydroxy; halogen-$(C_{1-8})$alkoxy substituted by $(C_{1-8})$alkoxy; halogen-$(C_{1-8})$alkoxy substituted by $(C_{1-8})$alkoxy-$(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkyl; halogen-$(C_{1-8})$alkoxy-$(C_{1-8})$alkyl; $(C_{1-8})$alkoxy-$(C_{1-8})$alkoxy; halogen-$(C_{1-8})$alkoxy-$(C_{1-8})$alkoxy; $(C_{1-8})$alkoxy-$(C_{1-8})$alkoxy-$(C_{1-8})$alkyl; halogen-$(C_{1-8})$alkoxy-$(C_{1-8})$alkoxy-$(C_{1-8})$alkyl; formyl; $(C_{1-8})$alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; aminocarbonyl; N—$(C_{1-8})$alkylaminocarbonyl optionally substituted by halogen; N,N-di-[$(C_{1-8})$alkyl]aminocarbonyl with two identical or different $(C_{1-8})$alkyl moieties, which two identical or different $(C_{1-8})$alkyl moieties can be substituted, identically or differently, by halogen; N—$(C_{3-8})$cycloalkylaminocarbonyl; N—[$(C_{3-8})$cycloalkyl-$(C_{1-8})$alkyl]aminocarbonyl; $(C_{1-8})$alkoxycarbonyl; halogen-$(C_{1-8})$alkoxycarbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy, and in which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, non-aromatic heterocyclyl or non-aromatic heterocyclyloxy group 1 or 2 —$CH_2$— ring members are optionally replaced with —$C(=O)$— ring members;

either $R_6$ is absent; and $R_7$ is absent;

or $R_6$ is oxo; and $R_7$ is absent;

or $R_6$ is oxo; and $R_7$ is oxo; imino; $(C_{1-8})$alkylimino; benzylimino; formylimino; or $(C_{1-8})$alkylcarbonyl-imino;

either $R_8$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl; and $R_9$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl;

or $R_8$ and $R_9$, taken together, complete, together with the carbon atom, to which they are attached, a $(C_{3-8})$cycloalkylidene moiety, in which $(C_{3-8})$cycloalkylidene moiety 1 of its —CH$_2$— ring members can be replaced with —O—;

$R_{10}$ is an aryl or heteroaryl group, which aryl or heteroaryl group is optionally mono-, di-, tri- or tetra-substituted by substituents independently selected from the group, consisting of (i) the univalent substituents halogen, hydroxy, —Si[$(C_{1-8})$alkyl]$_3$ with 3 identical or 2 or 3 different $(C_{1-8})$alkyl moieties, $(C_{1-8})$alkyl, halogen-$(C_{1-8})$alkyl, hydroxy-$(C_{1-8})$alkyl, hydroxy-$(C_{1-8})$alkyl substituted by halogen, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —CH$_2$— ring members can be replaced with —O—, and which $(C_{3-8})$cycloalkyl group, in which 1 of its —CH$_2$— ring members is optionally replaced with —O—, is optionally substituted by 1 to 4 substituents independently selected from the group, consisting of halogen, $(C_{1-8})$alkyl and halogen-$(C_{1-8})$alkyl, and (ii) the bivalent substituents $(C_{3-16})$alkylene, oxa-$(C_{2-16})$alkylene and $(C_{1-8})$alkylenoxa-$(C_{1-8})$alkylene, any such optional bivalent substituent being attached to two adjacent ring carbon atoms of the aryl or heteroaryl group; and either $R_{11}$ is hydrogen; and $R_{12}$ is hydroxy;

or $R_{11}$ and $R_{12}$ taken together are oxo, in free form or in salt form.

E.g. on account of one or more than one asymmetrical carbon atom, which may be present in a compound of the formula I, a corresponding compound of the formula I may exist in pure optically active form or in the form of a mixture of optical isomers, e.g. in the form of a racemic mixture. All of such pure optical isomers and all of their mixtures, including the racemic mixtures, are part of the present invention.

A compound of the formula I may exist in free form or in salt form, e.g. a basic compound in acid addition salt form or an acidic compound in the form of a salt with a base. All of such free compounds and salts are part of the present invention.

A compound of the formula I may exist in tautomeric form. All of such tautomers are part of the present invention.

The present invention includes all pharmaceutically acceptable isotope-labeled compounds of the formula I, wherein one or more than one atom is/are replaced by one or more than one atom having the same atomic number as, but an atomic mass different from, the one(s) usually found in nature. Examples of such isotopes are those of carbon, such as $^{11}$C, $^{13}$C or $^{14}$C, chlorine, such as $^{36}$Cl, fluorine, such as $^{18}$F, bromine, such as $^{76}$Br, hydrogen, such as $^2$H or $^3$H, iodine, such as $^{123}$I, $^{124}$I, $^{125}$I or $^{131}$I, nitrogen, such as $^{13}$N or $^{15}$N, oxygen, such as $^{15}$O, $^{17}$O or $^{18}$O, phosphorus, such as $^{32}$P, or sulphur, such as $^{35}$S. An isotope-labeled compound of the formula I can be prepared by a process analogous to those described in the Examples or by a conventional technique known to those skilled in the art using an appropriate isotopically-labeled reagent or starting material. The incorporation of a heavier isotope, such as $^2$H, may provide greater metabolic stability to a compound of the formula I, which may result in, for example, an increased in vivo-half-life of the compound or in reduced dosage requirements. Certain isotope-labeled compounds of the formula I, for example those incorporating a radioactive isotope, such as $^3$H or $^{14}$C, may be used in drug or substrate-tissue distribution studies. Compounds of the formula I with a positron emitting isotope, such as $^{11}$C, $^{18}$F, $^{13}$N or $^{15}$O, may be useful in positron emission tomography (PET) or single photon emission computed tomography (SPECT) studies, e.g. to examine substrate-receptor occupancies.

Halogen denotes fluorine, chlorine, bromine or iodine.

A halogenated group or moiety, such as halogenalkyl, can be mono-, poly- or per-halogenated.

An aryl group, ring or moiety is a naphthyl or, preferably, phenyl group, ring or moiety.

A heteroaryl group, ring or moiety is an aromatic 5- or 6-membered structure, in which structure 1, 2, 3 or 4 ring members are hetero ring members independently selected from the group, consisting of a nitrogen ring member, an oxygen ring member and a sulfur ring member, such as furyl, pyrrolyl, thienyl, pyrazolyl, imidazolyl, thiazolyl, isothiazolyl, oxazolyl, isoxazolyl, triazolyl, tetrazolyl, pyridazinyl, pyrimidyl or pyridyl.

A non-aromatic heterocyclyl group, ring or moiety is a non-aromatic 4-, 5-, 6- or 7-membered cyclic structure, in which cyclic structure 1, 2 or 3 ring members are hetero ring members independently selected from the group, consisting of a nitrogen ring member, an oxygen ring member and a sulfur ring member, such as azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

Any non-cyclic carbon containing group or moiety with more than 1 carbon atom is straight-chain or branched.

Unless defined otherwise, carbon containing groups, moieties or molecules contain 1 to 8, preferably 1 to 6, preferably 1 to 4, preferably 1 or 2, carbon atoms.

Examples of alkylene, oxaalkylene and alkylenoxaalkylene are prop-1,3-ylene, but-1,3-ylene, but-1,4-ylene, —O—CH$_2$—CH$_2$—, —O—CH$_2$—CH$_2$—CH$_2$—, —CH$_2$—O—CH$_2$—, —O—C(CH$_3$)$_2$—CH$_2$— and —CH$_2$—O—C(CH$_3$)$_2$—.

In preferred embodiments, the invention relates to a compound of the formula I, in free form or in salt form, in which (1) $R_1$ is hydrogen; halogen; or $(C_{1-8})$alkyl;

preferably hydrogen;

(2) $R_2$ is hydrogen; halogen; $(C_{1-8})$alkyl; halogen-$(C_{1-8})$alkyl; $(C_{1-8})$alkoxy; or halogen-$(C_{1-8})$-alkoxy;

preferably hydrogen; halogen; $(C_{1-8})$alkoxy; or halogen-$(C_{1-8})$alkoxy;

preferably hydrogen; halogen; $(C_{1-6})$alkoxy; or halogen-$(C_{1-6})$alkoxy;

(3) either $R_3$ is hydrogen; and $R_4$ is hydrogen; $(C_{1-8})$alkoxy-$(C_{1-8})$alkyl; $(C_{1-8})$alkylcarbonyloxy-$(C_{1-8})$alkyl; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; N—$(C_{3-8})$cycloalkylamino-$(C_{1-8})$alkyl; formyl; $(C_{1-8})$alkylcarbonyl; $(C_{1-8})$alkoxy-$(C_{1-8})$alkylcarbonyl;

amino-$(C_{1-8})$alkylcarbonyl; N—$(C_{1-8})$alkylamino-$(C_{1-8})$alkylcarbonyl; N,N-di-[$(C_{1-8})$alkyl]amino-$(C_{1-8})$alkylcarbonyl with two identical or different $(C_{1-8})$alkyl moieties in the N,N-di-[$(C_{1-8})$alkyl]amino moiety, which two $(C_{1-8})$alkyl moieties, taken together, can complete, together with the nitrogen atom, to which they are attached, a ring with 3 to 7 ring members; N—$(C_{3-8})$cycloalkylamino-$(C_{1-8})$alkylcarbonyl; or $(C_{1-8})$alkoxycarbonyl;

or $R_3$ is halogen-$(C_{1-8})$alkyl; hydroxy-$(C_{1-8})$alkyl; $(C_{1-8})$alkoxy-$(C_{1-8})$alkyl; formyl; $(C_{1-8})$-alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; $(C_{1-8})$alkoxycarbonyl; halogen-$(C_{1-8})$alkoxycarbonyl; or an aryl-$(C_{1-8})$alkyl group, which aryl-$(C_{1-8})$alkyl group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$-alkoxy; and $R_4$ is hydrogen; $(C_{1-8})$alkyl; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl; preferably either $R_3$ is hydrogen; and $R_4$ is hydrogen; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl;

or $R_3$ is halogen-$(C_{1-8})$alkyl; hydroxy-$(C_{1-8})$alkyl; $(C_{1-8})$alkoxy-$(C_{1-8})$alkyl; formyl; $(C_{1-8})$-alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; $(C_{1-8})$alkoxycarbonyl; halogen-$(C_{1-8})$alkoxycarbonyl; or an aryl-$(C_{1-8})$alkyl group, which aryl-$(C_{1-8})$alkyl group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$-alkoxy; and $R_4$ is hydrogen; $(C_{1-8})$alkyl; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl; preferably $R_3$ is hydrogen; and $R_4$ is hydrogen;

(4) $R_5$ is hydrogen; halogen; $(C_{1-8})$alkyl; halogen-$(C_{1-8})$alkyl; halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; $(C_{2-8})$alkenyl; $(C_{3-8})$cycloalkyl-$(C_{2-8})$alkenyl; halogen-$(C_{2-8})$alkenyl; $(C_{1-8})$alkoxy; halogen-$(C_{1-8})$alkoxy; halogen-$(C_{1-8})$alkoxy substituted by hydroxy; halogen-$(C_{1-8})$alkoxy substituted by $(C_{1-8})$alkoxy; halogen-$(C_{1-8})$alkoxy substituted by $(C_{1-8})$alkoxy-$(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkyl; halogen-$(C_{1-8})$alkoxy-$(C_{1-8})$alkyl; $(C_{1-8})$alkoxy-$(C_{1-8})$alkoxy; halogen-$(C_{1-8})$alkoxy-$(C_{1-8})$alkoxy; $(C_{1-8})$alkoxy-$(C_{1-8})$alkoxy-$(C_{1-8})$alkyl; halogen-$(C_{1-8})$alkoxy-$(C_{1-8})$alkoxy-$(C_{1-8})$alkyl; formyl; $(C_{1-8})$alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; aminocarbonyl; N—$(C_{1-8})$alkylaminocarbonyl optionally substituted by halogen; N,N-di-[$(C_{1-8})$alkyl]aminocarbonyl with two identical or different $(C_{1-8})$alkyl moieties, which two identical or different $(C_{1-8})$alkyl moieties can be substituted, identically or differently, by halogen; N—$(C_{3-8})$cycloalkylaminocarbonyl; N—[$(C_{3-8})$cycloalkyl-$(C_{1-8})$alkyl]aminocarbonyl; $(C_{1-8})$alkoxycarbonyl; halogen-$(C_{1-8})$alkoxycarbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy, and in which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, non-aromatic heterocyclyl or non-aromatic heterocyclyloxy group 1 or 2 —CH$_2$— ring members are optionally replaced with —C(═O)— ring members;

preferably hydrogen; halogen; $(C_{1-8})$alkyl; halogen-$(C_{1-8})$alkyl; halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; $(C_{2-8})$alkenyl; $(C_{3-8})$cycloalkyl-$(C_{2-8})$alkenyl; halogen-$(C_{2-8})$alkenyl; $(C_{1-8})$alkoxy; halogen-$(C_{1-8})$alkoxy; halogen-$(C_{1-8})$alkoxy substituted by hydroxy; halogen-$(C_{1-8})$alkoxy substituted by $(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkyl; halogen-$(C_{1-8})$alkoxy-$(C_{1-8})$alkyl; $(C_{1-8})$alkoxy-$(C_{1-8})$alkoxy; halogen-$(C_{1-8})$alkoxy-$(C_{1-8})$alkoxy; $(C_{1-8})$alkoxy-$(C_{1-8})$alkoxy-$(C_{1-8})$alkyl; halogen-$(C_{1-8})$alkoxy-$(C_{1-8})$alkoxy-$(C_{1-8})$alkyl; formyl; $(C_{1-8})$alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; aminocarbonyl; N—$(C_{1-8})$alkylaminocarbonyl optionally substituted by halogen; N,N-di-[$(C_{1-8})$alkyl]aminocarbonyl with two identical or different $(C_{1-8})$alkyl moieties, which two identical or different $(C_{1-8})$alkyl moieties can be substituted, identically or differently, by halogen; N—$(C_{3-8})$cycloalkylaminocarbonyl; N—[$(C_{3-8})$cycloalkyl-$(C_{1-8})$alkyl]aminocarbonyl; $(C_{1-8})$alkoxycarbonyl; halogen-$(C_{1-8})$alkoxycarbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$ alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy;

preferably hydrogen; halogen; $(C_{1-8})$alkyl; halogen-$(C_{1-8})$alkyl; $(C_{2-8})$alkenyl; $(C_{3-8})$cycloalkyl-$(C_{2-8})$alkenyl; halogen-$(C_{2-8})$alkenyl; $(C_{1-8})$alkoxy; halogen-$(C_{1-8})$alkoxy; $(C_{1-8})$alkoxy-$(C_{1-8})$alkyl; halogen-$(C_{1-8})$alkoxy-$(C_{1-8})$alkyl; $(C_{1-8})$alkoxy-$(C_{1-8})$alkoxy-$(C_{1-8})$alkyl; halogen-$(C_{1-8})$alkoxy-$(C_{1-8})$alkoxy-$(C_{1-8})$alkyl; formyl; $(C_{1-8})$alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; $(C_{1-8})$alkoxycarbonyl; halogen-$(C_{1-8})$alkoxy-carbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$-cycloalkoxy, aryl, aryloxy, heteroaryl, heteroaryloxy, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy;

preferably hydrogen; halogen; $(C_{1-8})$alkyl; halogen-$(C_{1-8})$alkyl; halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; $(C_{2-8})$alkenyl; $(C_{1-8})$alkoxy; halogen-$(C_{1-8})$alkoxy; halogen-$(C_{1-8})$alkoxy substituted by hydroxy; halogen-$(C_{1-8})$alkoxy substituted by $(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkoxy; formyl; $(C_{1-8})$alkylcarbonyl; aminocarbonyl; N—$(C_{1-8})$alkylaminocarbonyl optionally substituted by halogen; N—$(C_{3-8})$cycloalkylaminocarbonyl; N—[$(C_{3-8})$cycloalkyl-$(C_{1-8})$alkyl]aminocarbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, heteroaryl, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, heteroaryl, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy;

preferably hydrogen; halogen; $(C_{1-8})$alkyl; halogen-$(C_{1-8})$alkyl; $(C_{2-8})$alkenyl; formyl; $(C_{1-8})$-alkylcarbonyl; or a heteroaryl group, which heteroaryl group is optionally substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy;

preferably hydrogen; halogen; $(C_{1-8})$alkyl; halogen-$(C_{1-8})$alkyl; halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; $(C_{2-8})$alkenyl; $(C_{1-8})$alkoxy; halogen-$(C_{1-8})$alkoxy; halogen-$(C_{1-8})$alkoxy substituted by $(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkoxy; $(C_{1-8})$alkylcarbonyl; aminocarbonyl; N—$(C_{1-8})$alkylaminocarbonyl optionally substituted by halogen; N—[$(C_{3-8})$cycloalkyl-$(C_{1-8})$alkyl]aminocarbonyl; or a $(C_{3-8})$cycloalkyl-$(C_{1-8})$alkoxy, $(C_{3-8})$cycloalkoxy, heteroaryl, non-aromatic heterocyclyl or non-aromatic heterocyclyloxy group, which $(C_{3-8})$cycloalkyl-$(C_{1-8})$alkoxy, $(C_{3-8})$cycloalkoxy, heteroaryl, non-aromatic heterocyclyl or non-aromatic heterocyclyloxy group is optionally ring-substituted by 1 to 4 substituents independently selected from the group, consisting of halogen, $(C_{1-8})$alkyl and halogen-$(C_{1-8})$alkyl;

preferably hydrogen; halogen; $(C_{1-8})$alkyl; halogen-$(C_{1-8})$alkyl; $(C_{2-8})$alkenyl; $(C_{1-8})$alkylcarbonyl; or heteroaryl;

preferably hydrogen; halogen; $(C_{1-8})$alkyl; halogen-$(C_{1-6})$alkyl; halogen-$(C_{1-6})$alkyl monosubstituted by hydroxy; halogen-$(C_{1-6})$alkyl monosubstituted by $(C_{1-6})$alkoxy; N—$(C_{1-6})$alkylamino-$(C_{1-6})$alkyl; $(C_{2-8})$alkenyl; $(C_{1-8})$alkoxy; halogen-$(C_{1-6})$alkoxy; halogen-$(C_{1-6})$alkoxy monosubstituted by hydroxy; halogen-$(C_{1-6})$alkoxy monosubstituted by $(C_{1-6})$alkoxy; halogen-$(C_{1-6})$alkoxy monosubstituted by amino; halogen-$(C_{1-6})$alkoxy monosubstituted by N—$(C_{1-6})$alkylamino; halogen-$(C_{1-6})$alkoxy monosubstituted by N,N-di-[$(C_{1-6})$alkyl]amino with two identical or different $(C_{1-6})$alkyl moieties, which two $(C_{1-6})$ alkyl moieties, taken together, can complete, together with the nitrogen atom, to which they are attached, a ring with 3 to 7 ring members; $(C_{1-6})$alkoxy-$(C_{1-6})$alkoxy; $(C_{1-8})$alkylcarbonyl; N—$(C_{1-6})$alkylaminocarbonyl optionally substituted by halogen; N—[$(C_{3-8})$cycloalkyl-$(C_{1-6})$alkyl]aminocarbonyl; or a $(C_{3-8})$cycloalkyl-$(C_{1-6})$alkoxy, $(C_{3-8})$cycloalkoxy, heteroaryl, non-aromatic heterocyclyl or non-aromatic heterocyclyloxy group, which $(C_{3-8})$cycloalkyl-$(C_{1-6})$alkoxy, $(C_{3-8})$cycloalkoxy, heteroaryl, non-aromatic heterocyclyl or non-aromatic heterocyclyloxy group is optionally ring-substituted by 1 to 4 substituents independently selected from the group, consisting of halogen and $(C_{1-6})$alkyl; preferably hydrogen; halogen; $(C_{1-8})$alkyl; halogen-$(C_{1-6})$alkyl; $(C_{2-8})$alkenyl; $(C_{1-6})$alkylcarbonyl; or furyl; preferably halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; halogen-$(C_{1-8})$alkoxy substituted by hydroxy; halogen-$(C_{1-8})$alkoxy substituted by $(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl] amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkoxy; halogen-$(C_{1-8})$alkoxy-$(C_{1-8})$alkoxy; aminocarbonyl; N—$(C_{1-8})$alkylaminocarbonyl optionally substituted by halogen; N,N-di-[$(C_{1-8})$alkyl]aminocarbonyl with two identical or different $(C_{1-8})$alkyl moieties, which two identical or different $(C_{1-8})$alkyl moieties can be substituted, identically or differently, by halogen; N—$(C_{3-8})$cycloalkylaminocarbonyl; or N—[$(C_{3-8})$cycloalkyl-$(C_{1-8})$alkyl]aminocarbonyl; preferably halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; halogen-$(C_{1-8})$alkoxy substituted by hydroxy; halogen-$(C_{1-8})$alkoxy substituted by $(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkoxy; aminocarbonyl; N—$(C_{1-8})$alkylaminocarbonyl optionally substituted by halogen; N—$(C_{3-8})$cycloalkylaminocarbonyl; or N—[$(C_{3-8})$cycloalkyl-$(C_{1-8})$alkyl]aminocarbonyl; preferably halogen-$(C_{1-6})$alkyl monosubstituted by hydroxy; halogen-$(C_{1-6})$alkyl monosubstituted by $(C_{1-6})$alkoxy; N—$(C_{1-6})$alkylamino-$(C_{1-6})$alkyl; halogen-$(C_{1-6})$alkoxy monosubstituted by hydroxy; halogen-$(C_{1-6})$alkoxy monosubstituted by $(C_{1-6})$alkoxy; halogen-$(C_{1-6})$alkoxy monosubstituted by amino; halogen-$(C_{1-6})$alkoxy monosubstituted by N—$(C_{1-6})$alkylamino; halogen-$(C_{1-6})$alkoxy monosubstituted by N,N-di-[$(C_{1-6})$alkyl]amino with two identical or different $(C_{1-6})$alkyl moieties, which two $(C_{1-6})$alkyl moieties, taken together, can complete, together with the nitrogen atom, to which they are attached, a ring with 3 to 7 ring members; $(C_{1-6})$alkoxy-$(C_{1-6})$alkoxy; N—$(C_{1-6})$alkylaminocarbonyl optionally substituted by halogen; or N—[$(C_{3-8})$cycloalkyl-$(C_{1-6})$alkyl]aminocarbonyl;

(5) either
$R_6$ is absent; and
$R_7$ is absent;
or
$R_6$ is oxo; and
$R_7$ is absent;
or
$R_6$ is oxo; and
$R_7$ is oxo; imino; $(C_{1-8})$alkylimino; benzylimino; formylimino; or $(C_{1-8})$alkylcarbonyl-imino;
preferably either
$R_6$ is absent; and
$R_7$ is absent;
or
$R_6$ is oxo; and
$R_7$ is absent;
or
$R_6$ is oxo; and
$R_7$ is oxo; or imino;
preferably either
$R_6$ is oxo; and
$R_7$ is absent;
or
$R_6$ is oxo; and
$R_7$ is oxo; or imino;
preferably either
$R_6$ is oxo; and
$R_7$ is absent;
or
$R_6$ is oxo; and
$R_7$ is oxo;
preferably $R_6$ is oxo; and $R_7$ is oxo;

(6) either
$R_8$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl; and
$R_9$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl;
or
$R_8$ and $R_9$, taken together, complete, together with the carbon atom, to which they are attached, a $(C_{3-8})$cycloalkylidene moiety, in which $(C_{3-8})$cycloalkylidene moiety 1 of its —$CH_2$— ring members can be replaced with —O—; preferably either
$R_8$ is hydrogen; or $(C_{1-8})$alkyl; and
$R_9$ is hydrogen;
or
$R_8$ and $R_9$, taken together, complete, together with the carbon atom, to which they are attached, a $(C_{3-8})$cycloalkylidene moiety; preferably either
$R_8$ is hydrogen; or $(C_{1-8})$alkyl; and
$R_9$ is hydrogen;
or
$R_8$ and $R_9$, taken together, complete, together with the carbon atom, to which they are attached, a cyclopropylidene moiety;
preferably $R_8$ is hydrogen; or $(C_{1-6})$alkyl; and $R_9$ is hydrogen;
preferably $R_8$ is hydrogen; and $R_9$ is hydrogen;

(7) $R_{10}$ is an aryl or heteroaryl group, which aryl or heteroaryl group is optionally mono-, di-, tri- or tetra-substituted by substituents independently selected from the group, consisting of (i) the univalent substituents halogen, hydroxy, —Si[$(C_{1-8})$alkyl]$_3$ with 3 identical or 2 or 3 different $(C_{1-8})$alkyl moieties, $(C_{1-8})$alkyl, halogen-$(C_{1-8})$alkyl, hydroxy-$(C_{1-8})$alkyl, hydroxy-$(C_{1-8})$alkyl substituted by halogen, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —$CH_2$— ring members can be replaced with —O—, and which $(C_{3-8})$cycloalkyl group, in which 1 of its —$CH_2$— ring members is optionally replaced with —O—, is optionally substituted by 1 to 4 substituents independently selected from the group, consisting of halogen, $(C_{1-8})$alkyl and halogen-$(C_{1-8})$alkyl, and (ii) the bivalent substituents $(C_{3-16})$alkylene, oxa-$(C_{2-16})$alkylene and $(C_{1-8})$alkylenoxa-$(C_{1-8})$alkylene, any such optional bivalent substituent being attached to two adjacent ring carbon atoms of the aryl or heteroaryl group; preferably an aryl or heteroaryl group, which aryl or heteroaryl group is optionally mono-, di-, tri- or tetra-substituted by substituents independently selected from the group, consisting of (i) the univalent substituents halogen, hydroxy, $(C_{1-8})$alkyl, halogen-$(C_{1-8})$alkyl, hydroxy-$(C_{1-8})$alkyl, hydroxy-$(C_{1-8})$alkyl substituted by halogen, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —$CH_2$— ring members can be replaced with —O—, and which $(C_{3-8})$cycloalkyl group, in which 1 of its —$CH_2$— ring members is optionally replaced with —O—, is optionally substituted by 1 to 4 substituents independently selected from the group, consisting of halogen, $(C_{1-8})$alkyl and halogen-$(C_{1-8})$alkyl, and (ii) the bivalent substituents $(C_{3-16})$alkylene, oxa-$(C_{2-16})$alkylene and $(C_{1-8})$alkylenoxa-$(C_{1-8})$ alkylene, any such optional bivalent substituent being attached to two adjacent ring carbon atoms of the aryl or heteroaryl group;

preferably an aryl or heteroaryl group, which aryl or heteroaryl group is optionally substituted by 1 to 4 substituents independently selected from the group, consisting of halogen, hydroxy, $(C_{1-8})$alkyl, halogen-$(C_{1-8})$alkyl, hydroxy-$(C_{1-8})$alkyl, halogen-substituted hydroxy-$(C_{1-8})$alkyl, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —CH$_2$-ring members can be replaced with —O—, and which $(C_{3-8})$cycloalkyl group, in which 1 of its —CH$_2$— ring members is optionally replaced with —O—, is optionally substituted by 1 to 4 substituents independently selected from the group, consisting of halogen, $(C_{1-8})$alkyl and halogen-$(C_{1-8})$alkyl;

preferably an aryl or heteroaryl group, which aryl or heteroaryl group is optionally mono-, di-, tri- or tetra-substituted by substituents independently selected from the group, consisting of (i) the univalent substituents halogen, hydroxy, $(C_{1-8})$alkyl, halogen-$(C_{1-8})$alkyl, hydroxy-$(C_{1-8})$alkyl, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —CH$_2$-ring members can be replaced with —O—, and which $(C_{3-8})$cycloalkyl group, in which 1 of its —CH$_2$-ring members is optionally replaced with —O—, is optionally substituted by 1 to 4 substituents independently selected from the group, consisting of halogen, $(C_{1-8})$alkyl and halogen-$(C_{1-8})$alkyl, and (ii) the bivalent substituents $(C_{3-16})$alkylene, oxa-$(C_{2-16})$alkylene and $(C_{1-8})$alkylenoxa-$(C_{1-8})$alkylene, any such optional bivalent substituent being attached to two adjacent ring carbon atoms of the aryl or heteroaryl group;

preferably an aryl or heteroaryl group, which aryl or heteroaryl group is optionally substituted by 1 to 4 substituents independently selected from the group, consisting of halogen, hydroxy, $(C_{1-8})$alkyl, halogen-$(C_{1-8})$alkyl, hydroxy-$(C_{1-8})$alkyl, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —CH$_2$— ring members can be replaced with —O—, and which $(C_{3-8})$-cycloalkyl group, in which 1 of its —CH$_2$— ring members is optionally replaced with —O—, is optionally substituted by 1 to 4 substituents independently selected from the group, consisting of halogen, $(C_{1-8})$alkyl and halogen-$(C_{1-8})$alkyl;

preferably an aryl or heteroaryl group, which aryl or heteroaryl group is optionally mono- or di-substituted by substituents independently selected from the group, consisting of (i) the univalent substituents halogen, hydroxy, $(C_{1-8})$alkyl, halogen-$(C_{1-8})$alkyl, hydroxy-$(C_{1-8})$alkyl, an unsubstituted heteroaryl group and an oxetanyl group, which oxetanyl group is optionally substituted by 1 or 2 substituents independently selected from the group, consisting of halogen, $(C_{1-8})$alkyl and halogen-$(C_{1-8})$alkyl, and (ii) the bivalent substituents $(C_{1-8})$alkylenoxa-$(C_{1-8})$alkylene, any such optional bivalent substituent being attached to two adjacent ring carbon atoms of the aryl or heteroaryl group;

preferably an aryl or heteroaryl group, which aryl or heteroaryl group is optionally substituted by 1 or 2 substituents independently selected from the group, consisting of halogen, hydroxy, $(C_{1-8})$alkyl, halogen-$(C_{1-8})$alkyl, hydroxy-$(C_{1-8})$alkyl, an unsubstituted heteroaryl group and an oxetanyl group, which oxetanyl group is optionally substituted by 1 or 2 substituents independently selected from the group, consisting of halogen, $(C_{1-8})$alkyl and halogen-$(C_{1-8})$-alkyl;

preferably a phenyl, isoxazolyl or pyrazolyl group, which phenyl, isoxazolyl or pyrazolyl group is optionally mono- or di-substituted by substituents independently selected from the group, consisting of (i) the univalent substituents halogen, hydroxy, $(C_{1-8})$alkyl, halogen-$(C_{1-8})$alkyl, hydroxy-$(C_{1-8})$alkyl, an unsubstituted pyrazolyl group and an oxetanyl group, which oxetanyl group is optionally substituted by 1 or 2 substituents independently selected from the group, consisting of $(C_{1-8})$alkyl, and (ii) the bivalent substituents $(C_{1-8})$alkylenoxa-$(C_{1-8})$alkylene, any such optional bivalent substituent being attached to two adjacent ring carbon atoms of the phenyl, isoxazolyl or pyrazolyl group;

preferably a phenyl, isoxazolyl or pyrazolyl group, which phenyl, isoxazolyl or pyrazolyl group is optionally substituted by 1 or 2 substituents independently selected from the group, consisting of halogen, hydroxy, $(C_{1-8})$alkyl, halogen-$(C_{1-8})$alkyl, hydroxy-$(C_{1-8})$alkyl, an unsubstituted pyrazolyl group and an oxetanyl group, which oxetanyl group is optionally substituted by 1 or 2 substituents independently selected from the group, consisting of $(C_{1-8})$alkyl; preferably a phenyl, isoxazolyl or pyrazolyl group, which phenyl, isoxazolyl or pyrazolyl group is mono- or di-substituted by substituents independently selected from the group, consisting of (i) the univalent substituents halogen, hydroxy, $(C_{1-8})$alkyl, halogen-$(C_{1-6})$alkyl, hydroxy-$(C_{1-6})$alkyl, an unsubstituted pyrazolyl group and an oxetanyl group, which oxetanyl group is substituted by 1 or 2 substituents independently selected from the group, consisting of $(C_{1-8})$alkyl, and (ii) the bivalent substituents $(C_{1-6})$alkylenoxa-$(C_{1-6})$alkylene, any such optional bivalent substituent being attached to two adjacent ring carbon atoms of the phenyl, isoxazolyl or pyrazolyl group;

preferably a phenyl, isoxazolyl or pyrazolyl group, which phenyl, isoxazolyl or pyrazolyl group is substituted by 1 or 2 substituents independently selected from the group, consisting of halogen, hydroxy, $(C_{1-8})$alkyl, halogen-$(C_{1-6})$alkyl, hydroxy-$(C_{1-6})$alkyl, an unsubstituted pyrazolyl group and an oxetanyl group, which oxetanyl group is substituted by 1 or 2 substituents independently selected from the group, consisting of $(C_{1-8})$alkyl;

(8) either
  $R_{11}$ is hydrogen; and
  $R_{12}$ is hydroxy;
  or
  $R_{11}$ and $R_{12}$ taken together are oxo;

(9) $R_1$ is hydrogen; halogen; or $(C_{1-8})$alkyl;
  $R_2$ is hydrogen; halogen; $(C_{1-8})$alkyl; halogen-$(C_{1-8})$alkyl; $(C_{1-8})$alkoxy; or halogen-$(C_{1-8})$alkoxy;
  either
  $R_3$ is hydrogen; and
  $R_4$ is hydrogen; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl;
  or
  $R_3$ is halogen-$(C_{1-8})$alkyl; hydroxy-$(C_{1-8})$alkyl; $(C_{1-8})$alkoxy-$(C_{1-8})$alkyl; formyl; $(C_{1-8})$-alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; $(C_{1-8})$alkoxycarbonyl; halogen-$(C_{1-8})$alkoxycarbonyl; or an aryl-$(C_{1-8})$alkyl group, which aryl-$(C_{1-8})$alkyl group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$-alkoxy; and $R_4$ is hydrogen; $(C_{1-8})$alkyl; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl;

$R_5$ is hydrogen; halogen; $(C_{1-8})$alkyl; halogen-$(C_{1-8})$alkyl; $(C_{2-8})$alkenyl; $(C_{3-8})$cycloalkyl-$(C_{2-8})$alkenyl; halogen-$(C_{2-8})$alkenyl; $(C_{1-8})$alkoxy; halogen-$(C_{1-8})$alkoxy; $(C_{1-8})$alkoxy-$(C_{1-8})$alkyl; halogen-$(C_{1-8})$alkoxy-$(C_{1-8})$alkyl; $(C_{1-8})$alkoxy-$(C_{1-8})$alkoxy-$(C_{1-8})$alkyl; halogen-$(C_{1-8})$alkoxy-$(C_{1-8})$alkoxy-$(C_{1-8})$alkyl; formyl; $(C_{1-8})$alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; $(C_{1-8})$alkoxycarbonyl; halogen-$(C_{1-8})$alkoxy-carbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$-cycloalkoxy, aryl, aryloxy, heteroaryl, heteroaryloxy, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy;

either $R_6$ is absent; and $R_7$ is absent;

or $R_6$ is oxo; and $R_7$ is absent;

or $R_6$ is oxo; and $R_7$ is oxo; imino; $(C_{1-8})$alkylimino; benzylimino; formylimino; or $(C_{1-8})$alkylcarbonyl-imino;

either $R_8$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl; and $R_9$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl;

or $R_8$ and $R_9$, taken together, complete, together with the carbon atom, to which they are attached, a $(C_{3-8})$cycloalkylidene moiety, in which $(C_{3-8})$cycloalkylidene moiety 1 of its —$CH_2$— ring members can be replaced with —O—; and $R_{10}$ is an aryl or heteroaryl group, which aryl or heteroaryl group is optionally substituted by 1 to 4 substituents independently selected from the group, consisting of halogen, hydroxy, $(C_{1-8})$alkyl, halogen-$(C_{1-8})$alkyl, hydroxy-$(C_{1-8})$alkyl, halogen-substituted hydroxy-$(C_{1-8})$alkyl, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —$CH_2$— ring members can be replaced with —O—, and which $(C_{3-8})$cycloalkyl group, in which 1 of its —$CH_2$— ring members is optionally replaced with —O—, is optionally substituted by 1 to 4 substituents independently selected from the group, consisting of halogen, $(C_{1-8})$alkyl and halogen-$(C_{1-8})$alkyl.

The preferred embodiments (1) to (9) are preferred independently, collectively or in any combination or sub-combination.

In especially preferred embodiments, the invention relates to one or more than one of the compounds of the formula I mentioned in the Examples hereinafter, in free form or in salt form.

In a further aspect, the invention relates to a process for the preparation of a compound of the formula I, in free form or in salt form, comprising the steps of a) for the preparation of a compound of the formula I, in free form or in salt form, in which $R_3$ is hydrogen and $R_4$ is hydrogen, treatment of a compound of the formula

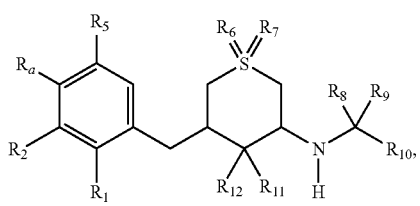

(II)

in which $R_a$ is azido or nitro and all of the other variables are as defined for the formula I, in free form or in salt form, with a reducing agent, in order to convert $R_a$ into amino, or b) for the preparation of a compound of the formula I, in free form or in salt form, in which $R_8$ is hydrogen, treatment of a compound of the formula

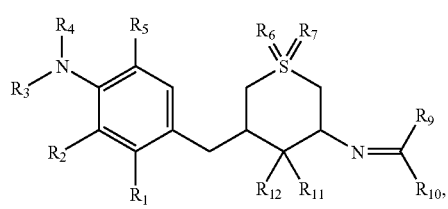

(III)

in which all of the variables are as defined for the formula I, in free form or in salt form, with a reducing agent, in order to convert the moiety —N=C($R_9$)$R_{10}$ into the moiety —N(H)—C(H)($R_9$)$R_{10}$, in each case optionally followed by reduction, oxidation or other functionalisation of the resulting compound and/or by cleavage of any protecting group(s) optionally present, and of recovering the so obtainable compound of the formula I in free form or in salt form.

The reactions can be effected according to conventional methods, for example as described in the Examples.

The working-up of the reaction mixtures and the purification of the compounds thus obtainable may be carried out in accordance with known procedures.

Salts may be prepared from free compounds in known manner, and vice-versa.

Compounds of the formula I can also be prepared by further conventional processes, which processes are further aspects of the invention, e.g. as described in the Examples.

The starting materials of the formulae II and III are known or may be prepared according to conventional procedures starting from known compounds, for example as described in the Examples.

Compounds of the formula I, in free form or in pharmaceutically acceptable salt form, herein-after often referred to as "agents of the invention", exhibit valuable pharmacological properties, when tested in vitro or in vivo, and are, therefore, useful in medicaments.

E.g., agents of the invention are inhibitors of aspartic proteases and can be used for the treatment or prevention of a condition, disease or disorder involving processing by such enzymes. Particularly, agents of the invention inhibit beta-secretase and, thus, the generation of beta-amyloid and the subsequent aggregation into oligomers and fibrils.

The inhibiting properties of an agent of the invention towards proteases can be evaluated, e.g., in a test as described hereinafter.

Test 1: Inhibition of Human BACE

Recombinant BACE (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic fluorescence-quenched peptide substrate, derived from the sequence of APP and containing a suitable fluorophore-quencher pair, is added to a final concentration of 1 to 5 µM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-activity as a function of the test compound concentration.

Test 2: Inhibition of Human BACE-2

Recombinant BACE-2 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic peptide substrate, derived from the sequence of APP and containing a suitable fluorophore-quencher pair, is added to a final concentration of 1 to 5 µM, and the increase in fluorescence is recorded at a suitable excitation/emission wave-length in a microplate spectro-fluorimeter for 5 to 30 minutes in 1-minute intervals. $IC_{50}$ values are calculated from percentage of inhibition of BACE-2-activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0 to 5.0. Synthetic peptide substrate Mca-Gly-Lys-Pro-Ile-Leu-Phe-Phe-Arg-Leu-Lys(DNP)-D-Arg-$NH_2$ is added to a final concentration of 1 to 5 µM, and the increase in fluorescence is recorded at excitation of 325 nm and emission at 400 nm in a microplate spectro-fluorimeter for 5 to 30 minutes in 1-minute intervals. $IC_{50}$ values are calculated from the percentage of inhibition of cathepsin D-activity as a function of the test compound concentration.

Test 4: Inhibition of Cellular Release of Amyloid Peptide 1-40

Chinese hamster ovary cells are transfected with the gene for amyloid precursor protein. The cells are plated at a density of 8000 cells/well into 96-well microtiter plates and cultivated for 24 hours in DMEM cell culture medium containing 10% FCS. The test compound is added to the cells at various concentrations, and the cells are cultivated for 24 hours in the presence of the test compound. The supernatants are collected, and the concentration of amyloid peptide 1-40 is determined using sandwich ELISA. The potency of the compound is calculated from the percentage of inhibition of amyloid peptide release as a function of the test compound concentration.

In at least one of the above-described tests, agents of the invention showed activity at concentrations below 50 µM. Specific activities of agents of the invention are described in Example 65.

Due to their inhibiting properties towards proteases, agents of the invention are useful, e.g., in the treatment or prevention of a variety of disabilitating psychiatric, psychotic, neurological or vascular states, e.g. of a condition, disease or disorder of the vascular system or of the nervous system, in which beta-amyloid generation or aggregation plays a role, or, based on the inhibition of BACE-2 (beta-site APP-cleaving enzyme 2) or cathepsin D, which are close homologues of the pepsin-type aspartyl proteases and beta-secretase, and the correlation of the BACE-2 or cathepsin D expression with a more tumorigenic or metastatic potential of tumor cells, as anti-cancer medicaments, e.g. in the suppression of the metastasis process associated with tumor cells. The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e.g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e.g. neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral hemorrhage with amyloidosis, Huntington's chorea, amyotrophic lateral sclerosis, multiple sclerosis or fragile X syndrome; scrapie; cerebral amyloid angiopathy; an encephalopathy, e.g. transmissible spongiform encephalopathy; stroke; an attention disorder, e.g. attention deficit hyperactivity disorder; Tourette's syndrome; a speech disorder, including stuttering; a disorder of the circadian rhythm, e.g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e.g. in paraplegic patients; a hearing disorder, e.g. tinnitus or age-related hearing impairment; urinary incontinence; glaucoma; inclusion-body myositis; or a substance-related disorder, including substance abuse or dependency, including a substance, such as alcohol, withdrawal disorder. Agents of the invention may also be useful in enhancing cognition, e.g. in a subject suffering from a dementing condition, such as Alzheimer's disease; as premedication prior to anaesthesia or a minor medical intervention, such as endoscopy, including gastric endoscopy; or as ligands, e.g. radioligands or positron emission tomography (PET) ligands.

For the above-mentioned indications, the appropriate dosage will vary depending on, e.g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e.g. in the form of a tablet or capsule, or parenterally, e.g. in the form of an injectable solution or suspension.

In accordance with the foregoing, in a further aspect, the invention relates to an agent of the invention for use as a medicament, e.g. for the treatment or prevention of a neurological or vascular condition, disease or disorder, in which beta-amyloid generation or aggregation plays a role, or for the suppression of the metastasis process associated with tumor cells.

In a further aspect, the invention relates to the use of an agent of the invention as active pharmaceutical ingredient in a medicament, e.g. for the treatment or prevention of a neurological or vascular condition, disease or disorder, in which beta-amyloid generation or aggregation plays a role, or for the suppression of the metastasis process associated with tumor cells.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e.g. grapefruit juice, ketoconazole or, preferably, ritonavir. Such a composition may be manufactured in conventional manner, e.g. by mixing its components. Unit dosage forms contain, e.g., from about 0.1 to about 1000, preferably from about 1 to about 500, mg of an agent of the invention.

An agent of the invention can be administered as sole active pharmaceutical ingredient or as a combination with at least one other active pharmaceutical ingredient effective, e.g., in the treatment or prevention of a neurological or vascular condition, disease or disorder, in which beta-amyloid generation or aggregation plays a role, or in the suppression of the metastasis process associated with tumor cells. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e.g. a pack or dispenser-device adapted for the concomitant or separate administration of the at least two active components, in which these active components are separately arranged. In a further aspect, the invention relates to such pharmaceutical combinations.

In a further aspect, the invention relates to the use of an agent of the invention for the manufacture of a medicament for the treatment or prevention of a neurological or vascular condition, disease or disorder, in which beta-amyloid generation or aggregation plays a role, or for the suppression of the metastasis process associated with tumor cells.

In a further aspect, the invention relates to a method for the treatment or prevention of a neurological or vascular condition, disease or disorder, in which beta-amyloid generation or aggregation plays a role, or for the suppression of the metastasis process associated with tumor cells, in a subject in need of such treatment, prevention or suppression, which method comprises administering to such subject an effective amount of an agent of the invention.

The following Examples illustrate the invention, but do not limit it.

EXAMPLES

| Abbreviations | |
|---|---|
| ACN | acetonitrile |
| AcOH | acetic acid |
| aq. | aqueous |
| nBuLi | n-butyl lithium |
| DBU | 1,8-diazabicyclo[5.4.0]undec-7-ene |
| DIBAL | diisobutylaluminiumhydride |
| DIPEA | diisopropylethylamine |
| DMAP | N,N-4-dimethylaminopyridine |
| DME | 1,2-dimethoxyethane |
| DMF | N,N-dimethylformamide |
| DMSO | dimethylsulfoxide |
| EDC | 1-(3-dimethylaminopropyl)-3-ethylcarbodiimide hydrochloride |
| ETA | ethanol-ammonia (conc.) 95:5 |
| EtOAc | ethylacetate |
| EtOH | ethanol |
| $Et_2O$ | diethylether |
| h | hour(s) |
| HOBT | hydroxy-benztriazole |
| iPrOH | iso-propanol |
| MeOH | methanol |
| min | minute(s) |
| NaHMDS | sodium hexamethyldisilazane |
| NaOAc | sodium acetate |
| $NEt_3$ | triethylamine |
| Oxone | potassium monopersulfate |
| $Pd(PPh_3)_4$ | tetrakis(triphenylphosphine)palladium(0) |
| $Pd_2(dba)_3$ | tris(dibenzylideneacetone)dipalladium |
| $PPh_3$ | triphenylphosphine |
| p-TsOH | para-toluenesulfonic acid |

| Abbreviations | |
|---|---|
| TBME | tert-butylmethyl-ether |
| TFA | trifluoroacetic acid |
| THF | tetrahydrofuran |
| TLC | thin layer chromatography |

General Chromatography Information

| HPLC method A ($Rt_A$): | |
|---|---|
| HPLC-column dimensions: | 4.6 × 50 mm |
| HPLC-column type: | Chromolith Speed ROD RP-18e, 2 μm |
| HPLC-eluent: | A) water + 0.1 Vol.-% TFA, B) ACN + 0.1 Vol.-% TFA |
| HPLC-gradient: | 10-100% B in 3 min, 100% B 1 min; flow = 4 ml/min |
| HPLC method B1 ($Rt_{B1}$): | |
| HPLC-column dimensions: | 4 × 125 mm |
| HPLC-column type: | MN Nucleodur C18 Pyramid, 5 μm |
| HPLC-eluent: | A) water + 0.1 Vol.-% TFA, B) ACN + 0.1 Vol.-% TFA |
| HPLC-gradient: | 5-100% B in 20 min; flow = 1 ml/min |
| HPLC method B2 ($Rt_{B2}$): | |
| HPLC-column dimensions: | 4 × 125 mm |
| HPLC-column type: | MN Nucleodur C18 Pyramid, 5 μm |
| HPLC-eluent: | A) water, B) ACN |
| HPLC-gradient: | 5-100% B in 20 min; flow = 1 ml/min |
| HPLC method C ($Rt_C$): | |
| HPLC-column dimensions: | 2.1 × 50 mm |
| HPLC-column type: | SunFire $C_{18}$, 5 μm |
| HPLC-eluent: | A) water + 0.1 Vol.-% TFA, B) ACN + 0.1 Vol.-% TFA |
| HPLC-gradient: | 20-95% B in 3.5 min, 95% B 0.5 min; flow = 0.8 ml/min |
| UPLC method D ($Rt_D$): | |
| HPLC-column dimensions: | 2.1 × 50 mm |
| HPLC-column type: | Acquity UPLC BEH C18, 1.7 μm |
| HPLC-eluent: | A) water + 0.1 Vol.-% TFA, B) ACN + 0.1 Vol.-% TFA |
| HPLC-gradient: | 5% B to 100% B in 2 min, flow = 0.6 ml/min |
| UPLC method E ($Rt_E$): | |
| HPLC-column dimensions: | 2.1 × 50 mm |
| HPLC-column type: | Acquity UPLC BEH C18, 1.7 μm |
| HPLC-eluent: | A) water + 0.1 Vol.-% TFA, B) ACN + 0.1 Vol.-% TFA |
| HPLC-gradient: | 2% B to 98% B in 1.15 min, flow = 1.0 ml/min |
| UPLC method F ($Rt_F$): | |
| HPLC-column dimensions: | 2.1 × 50 mm |
| HPLC-column type: | Acquity HSS T3 1.8 μm |
| HPLC-eluent: | A) water + 3 mM $NH_4OAc$, B) ACN + 0.05% formic acid |
| HPLC-gradient: | 2% B to 98% B in 5 min, flow 1 ml/min |
| HPLC method G1 ($Rt_{G1}$): | |
| HPLC-column dimensions: | 3.0 × 30 mm |
| HPLC-column type: | XBridge $C_{18}$, 2.5 μm |
| HPLC-eluent: | A) water + 5 Vol.-% ACN + 0.5 Vol.-% formic acid<br>B) ACN + 0.5 Vol.-% formic acid |
| HPLC-gradient: | 10-95% B in 1.7 min, 95% B for 0.7 min, flow = 1.4 ml/min |
| HPLC method G2 ($Rt_{G2}$): | |
| HPLC-column dimensions: | 3.0 × 30 mm |
| HPLC-column type: | XBridge $C_{18}$, 2.5 μm |
| HPLC-eluent: | A) water + 5 Vol.-% ACN + 0.5 Vol.-% formic acid<br>B) ACN + 0.5 Vol.-% formic acid |
| HPLC-gradient: | 10-95% B in 1.7 min, 95% B for 0.7 min, flow = 1.2 ml/min |
| HPLC method G3 ($Rt_{G3}$): | |
| HPLC-column dimensions: | 3.0 × 30 mm |
| HPLC-column type: | XBridge $C_{18}$, 2.5 μm |
| HPLC-eluent: | A) water + 5 Vol.-% ACN + 0.5 Vol.-% formic acid<br>B) ACN + 0.5 Vol.-% formic acid |
| HPLC-gradient: | 5-95% B in 3.7 min, 95% B for 0.7 min, flow = 1.2 ml/min |
| LCMS method H1 ($Rt_{H1}$): | |
| HPLC-column dimensions: | 3.0 × 30 mm |
| HPLC-column type: | Zorbax SB-C18, 1.8 μm |
| HPLC-eluent: | A) water + 0.05 Vol.-% TFA, B) ACN + 0.05 Vol.-% TFA |

| | |
|---|---|
| HPLC-gradient: | 30-100% B in 3.25 min, flow = 0.7 ml/min |
| | LCMS method H2 (Rt$_{H2}$): |
| HPLC-column dimensions: | 3.0 × 30 mm |
| HPLC-column type: | Zorbax SB-C8, 1.8 µm |
| HPLC-eluent: | A) water + 0.05 Vol.-% TFA, B) ACN + 0.05 Vol.-% TFA |
| HPLC-gradient: | 10-95% B in 3.25 min, flow = 0.7 ml/min |
| | LCMS method H3 (Rt$_{H3}$): |
| HPLC-column dimensions: | 3.0 × 30 mm |
| HPLC-column type: | Zorbax SB-C8, 1.8 µm |
| HPLC-eluent: | A) water + 0.05 Vol.-% TFA, B) ACN + 0.05 Vol.-% TFA |
| HPLC-gradient: | 40-100% B in 3.25 min, flow = 0.7 ml/min |
| | LCMS method I (Rt$_I$): |
| HPLC-column dimensions: | 3 × 30 mm |
| HPLC-column type: | XTERRA-C18, 2.5 µm |
| HPLC-eluent: | A) water + 0.2% formic acid, B) ACN + 0.2% formic acid |
| HPLC-gradient: | 10%-95% ACN in 1.5 min, 0.6 ml/min |

Example 1

(3S*,4S*,5R*)-3-[4-Amino-3-fluoro-5-((S)-3,3,3-trifluoro-2-hydroxy-propyl)-benzyl]-5-(3-tert-butyl-benzylamino)-1,1-dioxo-hexahydro-1lambda*6*-thiopyran-4-ol dihydrochloride a) 4-tert-Butoxycarbonylamino-3-oxo-5-tritylsulfanyl-pentanoic acid allyl ester To a solution of di-imidazol-1-yl-methanone (13.9 g, 84 mmol) in anhydrous THF (300 mL) was added dropwise a solution of (R*)-2-tert-butoxycarbonylamino-3-tritylsulfanyl-propionic acid (32.8 g, 70 mmol) and DMAP (0.26 g, 2.1 mmol) in THF (200 mL) at 25° C. over a period of 1 h. The reaction mixture was stirred for 2 h at ambient temperature before a solution of propanedioic acid mono-2-propenyl ester magnesium complex (13.6 g, 42 mmol) dissolved in THF (200 mL) was added. The reaction mixture was stirred for 16 h at 40-45° C. and then evaporated. The residue was re-dissolved in EtOAc and washed with cold 10% citric acid, water, saturated NaHCO$_3$ solution and brine, dried over MgSO$_4$ and evaporated. The title compound was obtained after flash-chromatography on silica gel (hexane-EtOAc 10:1 to 4:1) and crystallization from Et$_2$O-hexane as a white crystalline solid: TLC (hexane-EtOAc 1:1) Rf=0.64; HPLC Rt$_A$=2.64 min; ESIMS [M–H]$^-$=544; $^1$H NMR (400 MHz, CDCl$_3$): δ 7.2-7.5 (m, 15H), 5.84 (m, 1H), 5.16 (m, 2H), 5.02 (d, 1H), 4.57 (m, 2H), 4.08 (m, 1H), 3.36 (m, 2H), 2.72 (dd, 1H), 2.54 (dd, 1H), 1.42 (s, 9H).

b) 5-tert-Butoxycarbonylamino-4-oxo-tetrahydro-thiopyran-4-carboxylic acid allyl ester To a solution of 4-tert-butoxycarbonylamino-3-oxo-5-tritylsulfanyl-pentanoic acid allyl ester (24.0 g, 44 mmol) in AcOH (200 mL) was added piperidine (5.3 g, 61.6 mmol) and para-formaldehyde (1.46 g, 46 mmol) and the reaction mixture was stirred at 80° C. for 0.5 h. The reaction mixture was concentrated under reduced pressure and the residual solid was dissolved in EtOAc and washed with saturated NaHCO$_3$ solution and brine, dried over MgSO$_4$ and evaporated. The title compound was obtained after flash-chromatography on silica gel (toluene-EtOAc 40:1 to 10:1) and crystallization from diisopropylether as a white solid: TLC (toluene-EtOAc 10:1) Rf=0.32; HPLC Rt$_A$=1.91 min; ESIMS [M–H]$^-$=314; $^1$H NMR (400 MHz, CDCl$_3$): δ 5.94 (m, 1H), 5.68 (m, 1H), 5.35 (d, 1H), 5.27 (d, 1H), 4.62 (m, 3H), 3.87 (dd, 1H), 3.38 (dd, 1H), 3.22 (t, 1H), 3.04 (dt, 1H), 2.68 (m, 1H), 1.42 (s, 9H).

c) 5-tert-Butoxycarbonylamino-3-(3-fluoro-4-nitro-benzyl)-4-oxo-tetrahydro-thiopyran-3-carboxylic acid allyl ester To a solution of 5-tert-butoxycarbonylamino-4-oxo-tetrahydro-thiopyran-3-carboxylic acid allyl ester (2.55 g, 8.08 mmol) in acetone (150 mL) was added K$_2$CO$_3$ (3.38 g, 24.2 mmol) and 4-bromomethyl-2-fluoro-1-nitro-benzene (2.12 g, 8.9 mmol) and the reaction mixture was stirred at 25° C. for 16 h. After dilution with water the product is extracted with EtOAc. Combined extracts were washed with brine, dried over MgSO$_4$ and evaporated. The product obtained as a light yellow solid was suitable for use in the next step: TLC (hexane-EtOAc 1:3) Rf=0.26; HPLC Rt$_A$=2.31 min; ESIMS [M+NH$_4$]+=486.

d) [(3R*,5S*)-5-(3-Fluoro-4-nitro-benzyl)-4-oxo-tetrahydro-thiopyran-3-yl]-carbamic acid tert-butyl ester To a degassed solution of 5-tert-butoxycarbonylamino-3-(3-fluoro-4-nitro-benzyl)-4-oxo-tetra-hydro-thiopyran-3-carboxylic acid allyl ester (3.56 g, 7.6 mmol) and morpholine (1.4 mL, 15.2 mmol) in THF (50 mL) was added under argon Pd(PPh$_3$)$_4$ (0.092 g, 0.076 mmol) and the reaction mixture was stirred at 25° C. for 3 h. The reaction mixture was poured onto cold saturated NaHCO$_3$ solution and extracted with EtOAc. Combined extracts were washed with brine, dried over MgSO$_4$ and evaporated. The residue was re-dissolved in THF (10 mL) and kept at 25° C. for 3 h after addition of a catalytic amount of DBU. The title compound was obtained after evaporation and crystallization from diisopropylether as single diastereoisomer: TLC (hexane-EtOAc 1:2) Rf=0.38; HPLC Rt$_A$=2.17 min; ESIMS [M+NH$_4$]+=402; $^1$H NMR (400 MHz, CDCl$_3$): δ 8.0 (dd, 1H), 7.14 (m, 2H), 5.68 (m, 1H), 4.54 (m, 1H), 3.41 (m, 1H), 3.28 (dd, 1H), 3.14 (m, 1H), 2.84 (ddd, 1H), 2.69 (dd, 1H), 2.65 (m, 2H), 1.42 (s, 9H).

e) [(3R*,4R*,5S*)-5-(3-Fluoro-4-nitro-benzyl)-4-hydroxy-tetrahydro-thiopyran-3-yl]-carbamic acid tert-butyl ester To a solution of calcium borohydride bis-THF complex (1.14 g, 4.6 mmol) in anhydrous THF (100 mL) was added under argon a solution of [(3R*,5S*)-5-(3-fluoro-4-nitro-benzyl)-4-oxo-tetrahydro-thiopyran-3-yl]-carbamic acid tert-butyl ester (1.77 g, 4.6 mmol) in THF (50 mL) at −70° C. The reaction mixture was slowly warmed to −40° C. and stirred for 1 h at −40° C. The reaction mixture was poured onto a cold aq. $KHSO_4$ solution and the product was extracted with EtOAc. Combined extracts were washed with $NaHCO_3$ solution and brine, dried over $MgSO_4$ and evaporated. The mixture of diastereoisomers was separated by flash-chromatography on silica gel (toluene-EtOAc 6:1 to 3:1) to yield the undesired [(3R*,4S*,5S*)-diastereoisomer and the desired [(3R*,4R*,5S*)-diastereoisomer after crystallization from EtOH as a white crystalline solid: TLC (toluene-EtOAc 3:1) Rf=0.20; HPLC $Rt_A$=1.94 min; ESIMS [M+H-isobutylene]+=331; $^1$H NMR (600 MHz, DMSO-$d_6$): δ 8.09 (t, 1H), 7.41 (d, 1H), 7.27 (d, 1H), 6.67 (d, 1H), 4.94 (d, 1H), 3.42 (m, 1H), 3.27 (dd, 1H), 2.91 (m, 1H), 2.55 (m, 2H), 2.39 (dd, 1H), 2.24 (m, 2H), 1.93 (m, 1H), 1.37 (s, 9H).

f) [(3R*,4S*,5S*)-5-(3-Fluoro-4-nitro-benzyl)-4-hydroxy-1,1-dioxo-hexahydro-1lambda*6*-thiopyran-3-yl]-carbamic acid tert-butyl ester To a solution of [(3R*,4R*,5S*)-5-(3-fluoro-4-nitro-benzyl)-4-hydroxy-tetrahydro-thiopyran-3-yl]-carbamic acid tert-butyl ester (0.78 g, 2.0 mmol) in THF (15 mL) was added water (15 mL) and oxone (2.62 g, 4.2 mmol) and the reaction mixture was stirred for 2 h at 25° C. The excess oxone was destroyed after addition of 2 equivalents of NaOAc with sodium meta-bisulfite and the product was extracted with EtOAc. Combined extracts were washed with brine, dried over $MgSO_4$ and evaporated. The title compound was obtained as a light yellow solid suitable for use in the next step: TLC (toluene-EtOAc 1:1) Rf=0.18; HPLC $Rt_A$=1.67 min; ESIMS [M+$NH_4$]+=436; $^1$H NMR (600 MHz, DMSO-$d_6$): δ 8.11 (t, 1H), 7.41 (d, 1H), 7.27 (d, 1H), 6.71 (d, 1H), 5.22 (d, 1H), 3.72 (m, 1H), 3.0-3.2 (m, 5H), 2.82 (s, 1H), 2.71 (dd, 1H), 2.17 (dd, 1H), 1.38 (s, 9H).

g) (3R*,4S*,5S*)-3-Amino-5-(3-fluoro-4-nitro-benzyl)-1,1-dioxo-hexahydro-1lambda*6*-thiopyran-4-ol hydrochloride

[(3R*,4S*,5S*)-5-(3-Fluoro-4-nitro-benzyl)-4-hydroxy-1,1-dioxo-hexahydro-1lambda*6*-thio-pyran-3-yl]-carbamic acid tert-butyl ester (0.82 g, 1.94 mmol) in 4N HCl in dioxane (10 mL) was stirred for 1 h at 25° C. and 0.5 h at 40° C. The reaction mixture was evaporated and the product recrystallized from MeOH-$Et_2$O to yield the title compound as light yellow crystals: TLC ($CH_2Cl_2$-MeOH-AcOH-$H_2$O 180:20:2:1) Rf=0.19; ESIMS [M+H]+=319; $^1$H NMR (400 MHz, $CD_3$OD): δ 8.07 (t, 1H), 7.34 (d, 1H), 7.26 (d, 1H), 3.3-3.8 (m, 5H), 3.20 (dd, 1H), 2.91 (dt, 1H), 2.68 (dd, 1H), 2.42 (m, 1H).

h) (3R*,4S*,5S*)-3-(3-tert-Butyl-benzylamino)-5-(3-fluoro-4-nitro-benzyl)-1,1-dioxo-hexa-hydro-1lambda*6*-thiopyran-4-ol To a solution of (3R*,4S*,5S*)-3-amino-5-(3-fluoro-4-nitro-benzyl)-1,1-dioxo-hexahydro-1lambda*6*-thiopyran-4-ol hydrochloride (0.14 g, 0.39 mmol) in MeOH-$CH_2Cl_2$ 1:1 (3 mL) was added NaOAc (0.065 g, 0.78 mmol) and 3-tert-butyl-benzaldehyde (0.07 g, 0.43 mmol). The reaction mixture was stirred at 25° C. for 0.5 h before $NaBH_3CN$ (0.039 g, 0.59 mmol) was added followed by stirring for 16 h. The reaction mixture was acidified with 1N aq. HCl, stirred for 15 min, basified with $K_2CO_3$-solution and extracted with EtOAc. The combined organic layers were washed with brine, dried over $MgSO_4$ and evaporated. The title compound was obtained after purification by flash-chromatography on silica gel (hexane-$CH_2Cl_2$-MeOH 20:20:1 to 1:20:5) as a light yellow foam: TLC (EtOAc) Rf=0.45; HPLC $Rt_A$=1.78 min; ESIMS [M+H]+=465; $^1$H NMR (400 MHz, $CDCl_3$): δ 8.02 (t, 1H), 7.1-7.4 (m, 6H), 4.18 (s, 1H), 3.88 (d, 1H), 3.78 (d, 1H), 3.64 (m, 1H), 3.41 (ddd, 1H), 3.24 (ddd, 1H), 3.12 (dt, 1H), 3.00 (dd, 1H), 2.84, (m, 2H), 2.69 (m, 2H), 2.44 (m, 1H), 1.33 (s, 9H).

i) (3aR*,7S*,7aS*)-3-(3-tert-Butyl-benzyl)-7-(3-fluoro-4-nitro-benzyl)-5,5-dioxo-hexa-hydro-1-oxa-5lambda*6*-thia-3-aza-inden-2-one To a suspension of (3R*,4S*,5S*)-3-(3-tert-butyl-benzylamino)-5-(3-fluoro-4-nitro-benzyl)-1,1-dioxo-hexahydro-1lambda*6*-thiopyran-4-ol (4.4 g, 8.7 mmol) in ACN was added at 25° C. the DIPEA and the carbonyl-diimidazole. After addition of a catalytic amount of DMAP, the clear reaction mixture was kept at 25° C. for 16 h. The reaction mixture was poured onto ice-water and acidified with 4N aq. HCl. The precipitate was filtered off and washed with $H_2O$ and $Et_2O$, dried under reduced pressure for 6 h at 50° C. to yield the title product as light yellow crystals: TLC (toluene-THF 1:1) Rf=0.66; HPLC $Rt_A$=2.25 min; ESIMS [M+$NH_4$]+=508; $^1$H NMR (400 MHz, DMSO-$d_6$): δ 8.11 (dd, 1H), 7.48 (dd, 1H), 7.38 (s, 1H), 7.28 (m, 3H), 7.12 (d, 1H), 4.41 (d, 1H), 4.20 (m, 2H), 3.72 (m, 2H), 3.42 (dd, 1H), 3.14 (d, 2H), 3.04 (dd, 1H), 2.76 (dd, 1H), 2.64 (m, 1H), 1.25 (s, 9H).

j) (3aR*,7S*,7aS*)-7-(4-Amino-3-fluoro-benzyl)-3-(3-tert-butyl-benzyl)-5,5-dioxo-hexa-hydro-1 oxa-5lambda*6*-thia-3-aza-inden-2-one A solution of (3aR*,7S*,7aS*)-3-(3-tert-butyl-benzyl)-7-(3-fluoro-4-nitro-benzyl)-5,5-dioxo-hexahydro-1-oxa-5lambda*6*-thia-3-aza-inden-2-one (4.0 g, 8.1 mmol) in THF (150 mL) was hydrogenated over 10% Pd/C (300 mg) at 45° C. and 1 bar. After 16 h the catalyst was filtered off over Celite and the filtrate was evaporated. The residue was recrystallized from THF-hexane to yield the title compound as beige crystals: TLC (hexane-EtOAc 1:1) Rf=0.29; HPLC $Rt_A$=1.94 min; ESIMS [M+$NH_4$]+=478; $^1$H NMR (400 MHz, $CDCl_3$): δ 7.36 (d, 1H), 7.30 (d, 1H), 7.27 (s, 1H), 7.09 (d, 1H), 6.76 (dd, 1H), 6.7 (m, 2H), 4.52 (d, 1H), 4.31 (d, 1H), 3.85 (m, 1H), 3.74 (m, 1H), 3.05 (m, 3H), 2.80 (dd, 1H), 2.5-2.8 (m, 3H), 1.31 (s, 9H).

k) (3aR*,7S*,7aS*)-7-(4-Amino-3-fluoro-5-iodo-benzyl)-3-(3-tert-butyl-benzyl)-5,5-dioxo-hexahy-dro-1-oxa-5lambda*6*-thia-3-aza-inden-2-one To a suspension of (3aR*,7S*,7aS*)-7-(4-amino-3-fluoro-benzyl)-3-(3-tert-butyl-benzyl)-5,5-dioxo-hexahydro-1oxa-5lambda*6*-thia-3-aza-inden-2-one (3.0 g, 6.5 mmol) in $CH_2Cl_2$-MeOH 3:1 (180 mL) was added $CaCO_3$ (1.96 g, 19.4 mmol) and benzyltrimethylammonium dichloroiodide (3.47, 947 mmol) at 25° C. under Argon. The reaction mixture was heated at reflux for 16 h, diluted with $CH_2Cl_2$ and washed with ice-water, cold sodium thiosulfate solution and brine, dried over $MgSO_4$, filtered and evaporated. The residue was purified by flash-chromatography on silica gel (hexane-$CH_2Cl_2$-EtOAc 5:2:2 to 0:2:2) and crystallized from EtOAc-TBME-hexane to yield the title compound as light yellow crystals: TLC (hexane-EtOAc 1:1) Rf=0.39; HPLC $Rt_A$=2.31 min; ESIMS [M+NH$_4$]$^+$=604; $^1$H NMR (400 MHz, CDCl$_3$): δ 7.36 (d, 1H), 7.30 (d, 1H), 7.27 (m, 1H), 7.17 (s, 1H), 7.10 (d, 1H), 6.79 (dd, 1H), 4.53 (d, 1H), 4.32 (d, 1H), 4.15 (s, 2H), 3.85 (dt, 1H), 3.75 (t, 1H), 3.07 (m, 2H), 3.00 (d, 1H), 2.83 (t, 1H), 2.72 (dd, 1H), 2.55 (m, 2H), 1.31 (s, 9H).

l) N'-{4-[(3aR*,7S*,7aS*)-3-(3-tert-Butyl-benzyl)-2,5,5-trioxo-octahydro-1-oxa-5lambda*6*-thia-3-aza-inden-7-ylmethyl]-2-fluoro-6-iodo-phenyl}-N,N-dimethyl-form-amidine To a suspension of (3aR,7S,7aS)-7-(4-amino-3-fluoro-5-iodo-benzyl)-3-(3-tert-butyl-benzyl)-5,5-dioxo-hexahydro-1-oxa-5lambda*6*-thia-3-aza-inden-2-one (2.0 g, 3.2 mmol) in toluene (20 mL) was added N,N-dimethylformamid-dimethylacetal (1.18 g, 9.6 mmol) and the reaction mixture was heated in the microwave oven for 0.5 h at 150° C. After evaporation the residue was purified by chromatography (CombiFlash, 40 g silica gel, hexane-EtOAc 10:1 to EtOAc) to yield the title compound as beige crystals: TLC (hexane-EtOAc 1:1) Rf=0.39; HPLC Rt$_A$=1.92 min; ESIMS [M+H]$^+$ =641; $^1$H NMR (400 MHz, CDCl$_3$): δ 7.58 (d, 1H), 7.35 (m, 3H), 7.09 (d, 1H), 6.82 (dd, 1H), 4.54 (d, 1H), 4.33 (d, 1H), 3.83 (dt, 1H), 3.76 (t, 1H), 3.1 (m, 2H), 3.08 (s, 3H), 3.02 (s, 3H), 2.83 (t, 1H), 2.74 (dd, 1H), 2.58 (m, 2H), 1.31 (s, 9H).

m) N'-[4-[(3aR*,7S*,7aS*)-3-(3-tert-Butyl-benzyl)-2,5,5-trioxo-octahydro-1-oxa-5lambda*6*-thia-3-aza-inden-7-ylmethyl]-2-fluoro-6-((S)-3,3,3-trifluoro-2-hydroxy-propyl)-phenyl]-N,N-dimethyl-formamidine To a solution of N'-{4-[(3aR,7S,7aS)-3-(3-tert-butyl-benzyl)-2,5,5-trioxo-octahydro-1-oxa-5lambda*6*hia-3-aza-inden-7-ylmethyl]-2-fluoro-6-iodo-phenyl}-N,N-dimethyl-formam idine (0.2 g, 0.3 mmol) in anhydrous THF (4 mL) was added under argon 2 M iPrMgCl in THF (0.31 mL) at −40° C. After stirring for 20 min at −20° C., the reaction mixture was cooled to −50° C., CuI (0.03 g, 0.15 mmol) added and after stirring at −20° C. for 15 min, the (S)-2-rifluoro-methyl-oxirane (0.08 mL, 0.9 mmol) was added at −40° C. and the reaction mixture was stirred at −20° C. for 2 h. The reaction was quenched with cold 10% aq. NH$_4$Cl solution and the products were extracted with EtOAc. The combined organic layers were washed with brine, dried over MgSO$_4$, filtered and evaporated. The crude product was purified by chromatography (CombiFlash, 12 g silica gel, hexane-EtOAc 10:1 to EtOAc) to yield the title compound as a colorless oil: TLC (hexane-EtOAc 1:1) Rf=0.24; HPLC Rt$_A$=1.95 min; ESIMS [M+H]$^+$=628; $^1$H NMR (400 MHz, CDCl$_3$): δ 7.67 (d, 1H), 7.36 (d, 1H), 7.30 (d, 1H), 7.27 (s, 1H), 7.09 (d, 1H), 6.79 (dd, 1H), 6.74 (d, 1H), 4.52 (d, 1H), 4.33 (d, 1H), 4.12 (m, 1H), 3.84 (dt, 1H), 3.77 (t, 1H), 3.22 (dd, 1H), 3.09 (s, 3H), 3.02 (s, 3H), 2.9-3.1 (m, 4H), 2.83 (t, 1H), 2.74 (dd, 1H), 2.60 (m, 2H), 1.31 (s, 9H).

n) (3aR*,7S*,7aS*)-7-[4-Amino-3-fluoro-5-((S)-3,3,3-trifluoro-2-hydroxy-propyl)-benzyl]-3-(3-tert-butyl-benzyl)-5,5-dioxo-hexahydro-1-oxa-5lambda*6*-thia-3-aza-inden-2-one To a solution of N'-[4-[(3aR*,7S*,7aS*)-3-(3-tert-butyl-benzyl)-2,5,5-trioxo-octahydro-1-oxa-5lambda*6*-thia-3-aza-inden-7-ylmethyl]-2-fluoro-6-((S)-3,3,3-trifluoro-2-hydroxy-propyl)-phenyl]-N,N-dimethyl-formamidine (0.11 g, 0.17 mmol) in anhydrous EtOH (3 mL) was added ZnCl$_2$ (0.12 g, 0.86 mmol) and the reaction mixture was heated at reflux for 8 h. The reaction mixture was diluted with EtOAc and aq. K$_2$CO$_3$ solution. The product was extracted with EtOAc and the combined organic layers were washed with brine, dried over MgSO$_4$, filtered and evaporated. The crude product was purified by flash-chromatography on silica gel (hexane-EtOAc 2:1 to 1:2) to yield the title compound as a colorless foam: TLC (hexane-EtOAc 1:1) Rf=0.39; HPLC Rt$_A$=2.21 min; ESIMS [M+H]$^+$=573.

o) (3S*,4S*,5R*)-3-[4-Amino-3-fluoro-5-((S)-3,3,3-trifluoro-2-hydroxy-propyl)-benzyl]-5-(3-tert-butyl-benzylamino)-1,1-dioxo-hexahydro-1lambda*6*-thiopyran-4-ol To a solution of N'-[4-[(3aR*,7S*,7aS*)-3-(3-tert-butyl-benzyl)-2,5,5-trioxo-octahydro-1-oxa-5lambda*6*-thia-3-aza-inden-7-ylmethyl]-2-fluoro-6-((S)-3,3,3-trifluoro-2-hydroxy-propyl)-phenyl]-N,N-dimethyl-formamidine (0.1 g, 0.16 mmol) in anhydrous THF was added KOSi(CH$_3$)$_4$ (0.11 g, 0.8 mmol) and the reaction mixture was heated for 16 h at 60° C. The reaction mixture was added to cold 10% aq. K$_2$CO$_3$ solution and extracted with EtOAc. The combined organic layers were washed with 10% aq. K$_2$CO$_3$ solution and brine, dried over MgSO$_4$, filtered and evaporated. The residue was converted into the hydrochloride salt with 1N HCl in Et$_2$O and the precipitated salt was dried under reduced pressure to yield the title compound as a light yellow solid: TLC (CH$_2$Cl$_2$-MeOH-AcOH-H$_2$O 180:20:2:1) Rf=0.46; HPLC Rt$_A$=1.79 min; ESIMS [M+H]$^+$=547; HPLC Rt$_A$=1.22 min; ESIMS [M+H]$^+$=337; $^1$H NMR (400 MHz, CDCl$_3$+1% D$_2$O): δ 7.34 (m, 3H), 7.12 (d, 1H), 6.79 (dd, 1H), 6.66 (s, 1H), 4.14 (m, 1H), 3.87 (dd, 1H), 3.74 (dd, 1H), 3.38 (dt, 1H), 2.8-3.2 (m, 6H), 2.72 (dd, 1H), 2.63 (t, 1H), 2.55 (dd, 1H), 2.29 (m, 1H), 1.34 (s, 9H).

Example 2

(3S*,4S*,5R*)-3-[4-Amino-3-fluoro-5-((S)-3,3,3-trifluoro-2-methoxy-propyl)-benzyl]-5-(3-tert-butyl-benzylamino)-1,1-dioxo-hexahydro-1lambda*6*-thiopyran-4-ol trifluoroacetate a) N'-[4-[(3aR*,7S*,7aS*)-3-(3-tert-Butyl-benzyl)-2,5,5-trioxo-octahydro-1-oxa-5lambda*6*-thia-3-aza-inden-7-ylmethyl]-2-fluoro-6-((S)-3,3,3-trifluoro-2-methoxy-propyl)-phenyl]-N,N-dimethyl-formamidine To a solution of N'-[4-[(3aR*,7S*,7aS*)-3-(3-tert-butyl-benzyl)-2,5,5-trioxo-octahydro-1-oxa-5lambda*6*-thia-3-aza-inden-7-ylmethyl]-2-fluoro-6-((S)-3,3,3-trifluoro-2-hydroxy-propyl)-phenyl]-N,N-dimethyl-formamidine (0.095 g, 0.144 mmol) in anhydrous DMF was added under argon NaH (0.008 g, 0.34 mmol, 95%) and after 20 min stirring methyliodide (0.028 mL, 0.44 mmol). The reaction mixture was stirred for 2 h at 25° C. After addition of saturated aq. NaHCO$_3$ solution the title compound was extracted with EtOAc. The crude compound, a light yellow oil, was used as such in the next step: TLC (EtOAc) Rf=0.47; HPLC Rt$_A$=2.06 min; ESIMS [M+H]$^+$=642.

b) (3aR*,7S*,7aS*)-7-[4-Amino-3-fluoro-5-((S)-3,3,3-trifluoro-2-methoxy-propyl)-benzyl]-3-(3-tert-butyl-benzyl)-5,5-dioxo-hexahydro-1-oxa-5lambda*6*-thia-3-aza-inden-2-one The title compound was prepared in analogous manner as described for example 1n) from N'-[4-[(3aR*,7S*,7aS*)-3-

(3-tert-butyl-benzyl)-2,5,5-trioxo-octahydro-1-oxa-5lambda*6*-thia-3-aza-inden-7-ylmethyl]-2-fluoro-6-((S)-3,3,3-trifluoro-2-methoxy-propyl)-phenyl]-N,N-dimethyl-formamidine and ZnCl$_2$ to yield a yellow oil: TLC (hexane-EtOAc 2:1) Rf=0.22; HPLC Rt$_A$=2.40 min; ESIMS [M+H]$^+$=587.

c) (3S,4S,5R*)-3-[4-Amino-3-fluoro-5-((S)-3,3,3-trifluoro-2-methoxy-propyl)-benzyl]-5-(3-tert-butyl-benzylamino)-1,1-dioxo-hexahydro-1lambda*6*-thiopyran-4-ol trifluoro-acetate The title compound was prepared in analogous manner as described for example 1o) from (3aR*,7S*,7aS*)-7-[4-Amino-3-fluoro-5-((S)-3,3,3-trifluoro-2-methoxy-propyl)-benzyl]-3-(3-tert-butyl-benzyl)-5,5-dioxo-hexahydro-1-oxa-5lambda*6*-thia-3-aza-inden-2-one to yield an amorphous solid after purification by preparative HPLC (Sunfire C18 OBD 5 μm, 100×30, 5-100% ACN in water+ 0.1% TFA gradient, 25 min): TLC (CH$_2$Cl$_2$-MeOH 19:1) Rf=0.37; HPLC Rt$_A$=1.92 min; ESIMS [M+H]$^+$=561; $^1$H NMR (400 MHz, CDCl$_3$+1% D$_2$O): δ 7.34 (m, 3H), 7.09 (d, 1H), 6.77 (dd, 1H), 6.61 (s, 1H), 4.53 (d, 1H), 4.34 (d, 1H), 4.11 (m, 1H), 3.84 (dd, 1H), 3.74 (dd, 1H), 3.41 (s, 3H), 2.5-3.3 (m, 9H), 1.34 (s, 9H).

Example 3

(3S*,4S*,5R*)-3-(4-Amino-3-ethylaminomethyl-5-fluoro-benzyl)-5-(3-tert-butyl-benzylamino)-1,1-dioxo-hexahydro-1lambda*6*-thiopyran-4-ol hydrochloride a) (3aR*,7S*,7aS*)-7-(4-Amino-3-fluoro-5-vinyl-benzyl)-3-(3-tert-butyl-benzyl)-5,5-dioxo-hexahydro-1-oxa-5lambda*6*-thia-3-aza-inden-2-one To a degassed solution of (3aR*,7S*,7aS*)-7-(4-amino-3-fluoro-5-iodo-benzyl)-3-(3-tert-butyl-benzyl)-5,5-dioxo-hexahydro-1-oxa-5lambda*6*-thia-3-aza-inden-2-one (example 1k) (0.60 g, 1 mmol) in anhydrous dioxane (4 mL) was added under argon Cs$_2$CO$_3$ (0.665 g, 2.0 mmol), 2,4,6-trivinyl-cyclotriboroxane pyridine complex (0.365 g, 1.5 mmol) and tri-tert-butyl-phosphonium tetrafluoroborate (0.044 g, 0.15 mmol) in dioxane was added under argon the Pd$_2$(dba)$_3$ (0.028 g, 0.03 mmol) and the reaction mixture was heated at reflux for 2 h. The reaction mixture was diluted with EtOAc and the organic layer was washed with water and brine, dried over MgSO$_4$, filtered and evaporated. The title compound was obtained after flash-chromatography on silica gel (hexane-EtOAc 3:1 to 2:1) and crystallization from CH$_2$Cl$_2$-hexane as white crystals: HPLC Rt$_A$=2.22 min; ESIMS [M+NH$_4$]$^+$=504.

b) 2-Amino-5-[(3aR*,7S*,7aS*)-3-(3-tert-butyl-benzyl)-2,5,5-trioxo-octahydro-1-oxa-5lambda*6*-thia-3-aza-inden-7-ylmethyl]-3-fluoro-benzaldehyde A solution of (3aR*,7S*,7aS*)-7-(4-amino-3-fluoro-5-vinyl-benzyl)-3-(3-tert-butyl-benzyl)-5,5-dioxo-hexahydro-1-oxa-5lambda*6*-thia-3-aza-inden-2-one (0.215 g, 0.44 mmol) in CH$_2$Cl$_2$-MeOH 4:1 (10 mL) was ozonized at −78° C. until the educt disappeared. After addition of PPh$_3$ (0.139 g, 0.53 mmol) the reaction mixture was allowed to warm to 25° C. and the solvents were removed under reduced pressure. The title compound was obtained after flash-chromatography on silica gel (hexane-EtOAc 2:1) as white solid: ESIMS [M−H]$^−$=487.

c) (3aR*,7S*,7aS*)-7-(4-Amino-3-ethylaminomethyl-5-fluoro-benzyl)-3-tert-butyl-benzyl)-5,5-dioxo-hexahydro-1-oxa-5lambda*6*-thia-3-aza-inden-2-one To a solution of 2-amino-5-[(3aR*,7S*,7aS*)-3-(3-tert-butyl-benzyl)-2,5,5-trioxo-octahydro-1-oxa-5lambda*6*-thia-3-aza-inden-7-ylmethyl]-3-fluoro-benzaldehyde (0.12 g, 0.245 mmol) in CH$_2$Cl$_2$-MeOH 2:1 (3 mL) was added a 2M solution of ethylamine in MeOH (0.18 mL, 0.397 mmol). After stirring for 3 h at 25° C. the pH was adjusted to 4 with AcOH and the imine was reduced with NaBH$_3$CN (0.027 g 85%, 0.367 mmol). After 20 min the reaction mixture was basified with saturated K$_2$CO$_3$ solution and extracted with EtOAc. Combined organic layers were washed with water and brine, dried over MgSO$_4$, filtered and evaporated. The title compound was obtained after flash-chromatography on silica gel (CH$_2$Cl$_2$ to CH$_2$Cl$_2$-MeOH 20:1) as a beige solid: TLC (CH$_2$Cl$_2$-MeOH 19:1) Rf=0.39; ESIMS [M+H]$^+$=517.

d) (3S*,4S*,5R*)-3-(4-Amino-3-ethylaminomethyl-5-fluoro-benzyl)-5-(3-tert-butyl-benzylamino)-1,1-dioxo-hexahydro-1lambda*6*-thiopyran-4-ol hydrochloride The title compound was prepared in analogous manner as described for example 1o) from (3aR*,7S*,7aS*)-7-(4-amino-3-ethylaminomethyl-5-fluoro-benzyl)-3-(3-tert-butyl-benzyl)-5,5-dioxo-hexahydro-1-oxa-5lambda*6*-thia-3-aza-inden-2-one to yield the title compound as a beige solid: HPLC Rt$_A$=1.49 min; ESIMS [M+H]$^+$=492.

Example 4

1-{2-Amino-5-[(3S*,4S*,5R*)-5-(3-tert-butyl-benzylamino)-4-hydroxy-1,1-dioxo-hexahydro-1lambda*6*-thiopyran-3-ylmethyl]-3-fluoro-phenyl}-pyrrolidin-2-one di-trifluoroacetate a) (3aR*,7S*,7aS*)-7-[4-Amino-3-fluoro-5-(2-oxo-pyrrolidin-1-yl)-benzyl]-3-(3-tert-butyl-benzyl)-5,5-dioxo-hexahydro-1-oxa-5lambda*6*-thia-3-aza-inden-2-one To a solution of (3aR,7S,7aS)-7-(4-amino-3-fluoro-5-iodo-benzyl)-3-(3-tert-butyl-benzyl)-5,5-dioxo-hexahydro-1-oxa-5lambda*6*-thia-3-aza-inden-2-one (0.10 g, 0.17 mmol), 2-pyrrolidin-one (0.02 mL, 0.26 mmol) and N,N'-dimethylethylenediamine (0.002 mg, 0.017 mmol) in dioxane (10 mL) was added CuI (0.002 g, 0.009 mmol) and K$_3$PO$_4$ (0.077 g, 0.36 mmol) and the reaction mixture was heated at 115° C. for 4 h. The reaction mixture was filtered over Celite and concentrated. The crude product was purified on the flashmaster (10 g silicagel, cyclohexane-EtOAc 100:0 to 0:100) to yield the title compound as a yellow solid, which was directly used as such in the next step: HPLC Rt$_C$=4.728 min; ESIMS [M+H]+=544.

b) 1-{2-Amino-5-[(3S*,4S*,5R*)-5-(3-tert-butyl-benzylamino)-4-hydroxy-1,1-dioxo-hexahydro-1lambda*6*-thiopyran-3-ylmethyl]-3-fluoro-phenyl}-pyrrolidin-2-one di-trifluoroacetate To a solution of (3aR*,7S*,7aS*)-7-[4-amino-3-fluoro-5-(2-oxo-pyrrolidin-1-yl)-benzyl]-3-(3-tert-butyl-benzyl)-5,5- dioxo-hexahydro-1-oxa-5lambda*6*-thia-3-aza-inden-2-one (0.087 g, 0.16 mmol in THF (10 mL) was added KOSi(CH₃)₄ (0.126 g, 0.88 mmol) and the reaction mixture was stirred for 0.5 h at 80° C., then quenched with 1N HCl in Et₂O and evaporated. The residue was basified with saturated aq. NaHCO₃ solution and extracted with EtOAc. Combined layers were washed with brine, dried over Na₂SO₄, filtered and concentrated. The crude product was purified by preparative HPLC (Sunfire C18 OBD 5 μm, 100×30, 5-100% ACN in water+0.1% TFA gradient, 25 min) to yield to a white solid: HPLC Rt$_C$=3.329 min; ESIMS [M+H]⁺=518; NMR (400 MHz, CDCl₃+0.5% D₂O): δ 7.44 (m, 2H), 7.33 (t, 1H), 7.19 (d, 1H), 6.70 (m, 2H), 4.20 (m, 2H), 3.79 (m, 2H), 3.66 (dd, 1H), 3.51, (m, 1H), 3.18 (m, 2H), 2.89 (m, 1H), 2.78 (dd, 1H), 2.70 (m, 2H), 2.56 (m, 2H), 2.23 (m, 3H), 1.30 (s, 9H).

Example 5

1 {2-Amino-5-[(3S*,4S*,5R*)-5-(3-tert-butyl-benzylamino)-4-hydroxy-1,1-dioxo-hexahydro-1lambda*6*-thiopyran-3-ylmethyl]-3-fluoro-phenyl}-azetidin-2-one The title compound was prepared in analogous manner as described for example 4 from (3aR*,7S*,7aS*)-7-(4-amino-3-fluoro-5-iodo-benzyl)-3-(3-tert-butyl-benzyl)-5,5-dioxo-hexa-hydro-1-oxa-5lambda*6*-thia-3-aza-inden-2-one (example 1k) and azetidin-2-one: HPLC Rt$_C$=2.99 min; ESIMS [M+H]⁺=504; NMR (400 MHz, CDCl₃+0.5% D₂O): δ 7.65 (m, 2H), 7.56 (t, 1H), 7.47 (m, 3H), 6.30 (m, 2H), 4.20 (q, 2H), 3.80 (m, 2H), 3.59 (m, 2H), 3.35, (m, 2H), 3.18 (m, 2H), 2.95 (m, 1H), 2.85 (m, 1H), 2.75 (m, 2H), 1.30 (s, 9H).

Example 6

N-{4-[(3S*,4S*,5R*)-5-(3-tert-Butyl-benzylamino)-4-hydroxy-1,1-dioxo-hexa-hydro-1lambda*6*-thiopyran-3-ylmethyl]-2-fluoro-phenyl}-2-dimethylamino-acetamide a) N-{4-[(3aR,7S*,7aS*)-3-(3-tert-Butyl-benzyl)-2,5,5-trioxo-octahydro-1-oxa-5lambda*6*-thia-3-aza-inden-7-ylmethyl]-2-fluoro-phenyl}-2-dimethylamino-acetamide A mixture of (3aR*,7S*,7aS*)-7-(4-amino-3-fluoro-benzyl)-3-(3-tert-butyl-benzyl)-5,5-dioxo-hexahydro-1oxa-5lambda*6*-thia-3-aza-inden-2-one (example 1j), 1.06 g, 2.3 mmol), N-methylmorpholine (0.507 mL, 4.6 mmol), N,N-dimethylglycine (0.356 g, 3.45 mmol) and propylphosphoric acid anhydride (50% in DMF, 2.68 mL, 4.6 mmol) was stirred in DMF (9.2 mL) at 25° C. for 19 h. The reaction mixture was diluted with EtOAc and washed with saturated NaHCO₃ solution, water and brine. The organic layer was dried over Na₂SO₄, filtered and evaporated to leave the title compound as a colorless, amorphous powder: TLC (toluene-ETA 85:15) Rf=0.36; HPLC Rt$_A$=1.84 min; ESIMS [M+H]⁺=546; ¹H NMR (600 MHz, DMSO-d₆): δ 9.46 (s, 1H), 7.85 (t, 1H), 7.39 (s, 1H), 7.32 (d, 1H), 7.28 (t, 1H), 7.17-7.11 (m, 2H), 7.0 (d, 1H), 4.42 (d, 1H), 4.23 (d, 1H), 4.16 (t, 1H), 3.74-3.65 (m, 2H), 3.45 (t, 1H), 3.08 (m, 3H), 3.01 (m, 1H), 2.93 (m, 1H), 2.58 (m, 1H), 2.52 (m, 1H), 2.30 (s, 6H), 1.25 (s, 9H).

b) N-{4-[(3S*,4S*,5R*)-5-(3-tert-Butyl-benzylamino)-4-hydroxy-1,1-dioxo-hexahydro-1lambda*6*-thiopyran-3-ylmethyl]-2-fluoro-phenyl}-2-dimethylamino-acetamide The title compound was prepared in analogous manner as described for example 1o from N-{4-[(3aR*,7S*,7aS*)-3-(3-tert-butyl-benzyl)-2,5,5-trioxo-octahydro-1-oxa-5lambda*6*-thia-3-aza-inden-7-ylmethyl]-2-fluoro-phenyl}-2-dimethylamino-acetamide to yield an amorphous solid: TLC (toluene-ETA 85:15) Rf=0.34; HPLC Rt$_A$=1.47 min; ESIMS [M+H]⁺=520; ¹H NMR (600 MHz, DMSO-d₆): δ 9.46 (s, 1H), 7.86 (t, 1H), 7.35 (s, 1H), 7.23 (m, 2H), 7.13 (d, 1H), 7.10 (d, 1H), 6.98 (d, 1H), 5.22 (d, 1H), 3.79 (m, 1H), 3.63 (m, 1H), 3.38 (m, 1H), 3.16 (m, 1H), 3.08 (m, 3H), 2.98 (m, 2H), 2.79 (m, 1H), 2.64 (m, 1H), 2.51 (m, 1H), 2.41 (br, 1H), 2.27 (s, 6H), 2.04 (m, 1H), 1.25 (s, 9H).

Example 7

(3R*,4S*,5S*)-3-(3-tert-Butyl-benzylamino)-5-[4A2-dimethylamino-ethyl-amino]-3-fluoro-benzyl]-1,1-dioxo-hexahydro-1lambda*6*-thiopyran-4-ol a) (3aR*,7S*,7aS*)-3-(3-tert-Butyl-benzyl)-7-[4-(2-dimethylamino-ethylamino)-3-fluoro-benzyl]-5,5-dioxo-hexahydro-1-oxa-5lambda*6*-thia-3-aza-inden-2-one To a solution of N-{4-[(3aR*,7S*,7aS*)-3-(3-tert-butyl-benzyl)-2,5,5-trioxo-octahydro-1-oxa-5lambda*6*-thia-3-aza-inden-7-ylmethyl]-2-fluoro-phenyl}-2-dimethylamino-acetamide (example 6a), 0.055 g, 0.1 mmol) in THF (1.1 mL) was added borane THF-complex (1M in THF, 1 mL, 1 mmol) at 25° C. The mixture was stirred for 17 h at 25° C. and afterwards 3 h at reflux. The reaction mixture was evaporated and diluted with EtOAc; ice cold aq. H₂SO₄ was added carefully and the organic layer was washed with water, brine, dried over Na₂SO₄, filtered and evaporated to leave an amorphous powder which was dissolved in MeOH (3 mL). and 2N aq. HCl (2.5 mL) and the solution was kept at 80° C. for 17 h. The colorless solution was basified with aq. NaOH and extracted with EtOAc. Organic layers were washed with brine, dried over Na₂SO₄, filtered and concentrated to give the title compound as a slight brownish foam: TLC (toluene-ETA 85:15) Rf=0.30; HPLC Rt$_A$=1.91 min; ESIMS [M+H]⁺=532; ¹H NMR (600 MHz, DMSO-d₆): δ 7.39 (s, 1H), 7.33 (m, 1H), 7.28 (t, 1H), 7.13 (d, 1H), 6.9 (d, 1H), 6.82 (d, 1H), 6.72 (t, 1H), 5.51 (d, 1H), 4.40 (d, 1H), 4.22 (d, 1H), 4.11 (t, 1H), 3.67 m, 2H), 3.44 (m, 3H), 3.01 (m, 2H), 2.84 (m, 3H), 2.55 (s, 6H), 2.46 (m, 2H), 1.25 (s, 9H).

b) (3R*,4S*,5S*)-3-(3-tert-Butyl-benzylamino)-5-[4-(2-dimethylamino-ethylamino)-3fluoro-benzyl]-1,1-dioxo-hexahydro-1lambda*6*-thiopyran-4-ol The title compound was prepared in analogous manner as described for example 1o from (3aR*,7S*,7aS*)-3-(3-tert-butyl-benzyl)-7-[4-(2-dimethylamino-ethylamino)-3-fluoro-benzyl]-5,5-dioxo-hexahydro-1-oxa-5lambda*6*-thia-3-aza-inden-2-one to yield a sticky oil: TLC (toluene-ETA 85:15) Rf=0.20; HPLC Rt$_A$=1.51 min; ESIMS [M+H]⁺=506; ¹H-NMR (600 MHz, DMSO-d₆): δ 7.35 (s, 1H), 7.24 (m, 2H), 7.13 (d, 1H), 6.85 (d, 1H), 6.78 (d, 1H), 6.65 (t, 1H), 5.65 (d, 1H), 4.92 (m, 1H), 3.80 (d, 1H), 3.62 (d, 1H), 3.37 (m, 1H), 3.10 (m, 3H), 2.95 (m, 3H), 2.78 (m, 1H), 2.63 (m, 1H), 2.45 (t, 2H), 2.37 (m, 1H), 2.15 (s, 6H), 1.98 (m, 1H), 1.25 (s, 9H).

Example 8

N-{4-[(3S,4S,5R)-5-(3-tert-Butyl-benzylamino)-4-hydroxy-1,1-dioxo-hexahydro-1lambda*6*-thiopyran-3-ylmethyl]-2-ethyl-6-fluoro-phenyl}-2-ethylamino-acetamide dihydrochloride a) (2-Fluoro-4-hydroxymethyl-phenyl)-carbamic acid benzyl ester

To a mixture of 4-amino-3-fluorobenzylalcohol (20.7 g, 147 mmol) and pyridine (35.5 ml, 79 mmol) in THF (320 ml) and 2N NaOH (80 mL) was added benzyl chloroformate (24.8 mL, 170.6 mmol) at 0° C. over a period of 15 min. The reaction mixture was stirred for 20 min at 0° C. and for 2 h at room temperature. The reaction was quenched with water and diluted with EtOAc. The phases were separated and the organic phase was washed with 5% $NaHSO_4$, saturated aq. $NaHCO_3$ and brine, dried over $Na_2SO_4$, filtered and evaporated. The title compound was crystallized from EtOAc and cyclohexane: TLC (cyclohexane-EtOAc 3:1) Rf=0.45; HPLC $Rt_E$=1.02 min; ESIMS $[M+NH_4]^+$=293; ESIMS $[M-H]^-$=274; $^1$H NMR (360 MHz, $CDCl_3$): δ 8.00 (t, 1H), 7.40-7.25 (m, 5H), 7.10-7.00 (m, 2H), 6.82 (s broad, 1H), 5.15 (s, 2H), 4.55 (d, 2H).

b) (4-Bromomethyl-2-fluoro-phenyl)-carbamic acid benzyl ester

Phosphorous tribromide (20.9 mL, 218 mmol) was added to diethylether (700 mL) at 0° C. To the PBr3 solution was added dropwise (2-fluoro-4-hydroxymethyl-phenyl)-carbamic acid benzyl ester (36.5 g, 133 mmol) in $Et_2O$ (400 mL) at 0° C. over 1 h. The reaction mixture was stirred at room temperature for 45 min and was carefully quenched at 0° C. with MeOH (100 mL). The reaction mixture was diluted with aq. $NaHCO_3$ solution and extracted with EtOAc. The combined organic phases were washed with brine, dried over $Na_2SO_4$, filtered and evaporated to provide the title compound as a yellow foam: TLC (cyclohexane-EtOAc 1:1) Rf=0.88; HPLC $Rt_f$=1.16 min; $^1$H NMR (360 MHz, $CDCl_3$): δ 8.13 (t, 1H), 7.48-0.37 (m, 5H), 7.21-7.14 (m, 2H), 6.78 (s broad, 1H), 5.25 (s, 2H), 4.47 (s, 2H).

c) (R*)-3-(4-Benzyloxycarbonylamino-3-fluoro-benzyl)-5-tert-butoxycarbonylamino-4-oxo-tetrahydro-thiopyran-3-carboxylic acid allyl ester The title compound was prepared in analogous manner as described for example 1c from (4-bromomethyl-2-fluoro-phenyl)-carbamic acid benzyl ester (37 g, 109 mmol) and 5-tert-butoxycarbonylamino-4-oxo-tetrahydro-thiopyran-3-carboxylic acid allyl ester (33 g, 105 mmol, example 1b) to yield a diastereomeric mixture of a yellow solid: TLC (cyclohexane-EtOAc 1:1) Rf=0.77; ESIMS $[M+NH_4]^+$=590; LCMS $[M+NH_4]^+$=590, $Rt_f$=1.60 min.

d) [(3R*,5S*)-5-(4-Benzyloxycarbonylamino-3-fluoro-benzyl)-4-oxo-tetrahydro-thiopyran-3-yl]-carbamic acid tert-butyl ester The title compound was prepared in analogous manner as described for example 1d from (R*)-3-(4-benzyloxycarbonylamino-3-fluoro-benzyl)-5-tert-butoxycarbonylamino-4-oxo-tetra-hydro-thiopyran-3-carboxylic acid allyl ester (64.6 g, 113 mmol) to yield the racemic 1,3-cis diastereomer after isomerization as white crystals: HPLC $Rt_B$=17.92 min; ESIMS $[M+NH_4]^+$=506; $^1$H NMR (360 MHz, $CDCl_3$): δ 8.05 (t, 1H), 7.48-7.35 (m, 5H), 6.98-6.87 (m, 3H), 5.78 (d, 1H), 5.25 (s, 2H), 4.58 (m, 1H), 3.42 (m, 1H), 3.20 (dd, 1H), 3.10 (m, 1H), 2.85 (m, 1H), 2.70-2.61 (m, 2H), 2.55 (dd, 1H), 1.50 (s, 9H).

e) [(3R*,4S*,5S*)-5-(4-Benzyloxycarbonylamino-3-fluoro-benzyl)-4-hydroxy-tetrahydro-thiopyran-3-yl]-carbamic acid tert-butyl ester The title compound was prepared in analogous manner as described for example 24f) from [(3R*,5S*)-5-(4-benzyloxycarbonylamino-3-fluoro-benzyl)-4-oxo-tetrahydro-thiopyran-3-yl]-carbamic acid tert-butyl este (8.77 g, 17.9 mmol) to yield the racemic 1,3-cis diastereomer after crystallization from THF and diisopropylether: as white crystals: HPLC $Rt_f$=1.38 min; ESIMS $[M+NH_4]^+$=508; $^1$H NMR (360 MHz, $CDCl_3$): δ 7.91 (t, 1H), 7.38-7.28 (m, 5H), 6.90-6.80 (m, 2H), 6.78 (s, broad, 1H), 5.15 (s, 2H), 4.56 (m, 1H), 3.66 (m, 1H), 3.18 (dd, 1H), 2.96 (m, 1H), 2.78 (s, broad, 1H), 2.67 (m, 1H), 2.45-2.29 (m, 3H), 2.20 (t, 1H), 2.00 (m, 1H), 1.40 (s, 9H).

f) (3aR*,7S*,7aS*)-7-(4-Benzyloxycarbonylamino-3-fluoro-benzyl)-2,2-dimethyl-tetra-hydro-1-oxa-5-thia-3-aza-indene-3-carboxylic acid tert-butyl ester To a suspension of [(3R*,4S*,5S*)-5-(4-benzyloxycarbonylamino-3-fluoro-benzyl)-4-hydroxy-tetrahydro-thiopyran-3-yl]-carbamic acid tert-butyl ester (50.5 g, 102.9 mmol) and acetone dimethylketal (263 mL, 2.06 mol) in $CH_2Cl_2$ (500 mL) was added p-TsOH (200 mg, 1 mmol) at 0-5° C. and the reaction mixture was stirred for 4 h at 25° C. The reaction mixture was washed with saturated $NaHCO_3$ solution and water, dried over $MgSO_4$, filtered and evaporated to dryness. The title compound obtained as a yellow oil was used as such in the next step: TLC (toluene-EtOAc 3:1) Rf=0.40; HPLC $Rt_A$=2.80 min; ESIMS $[M-H]^-$=529; $^1$H NMR (400 MHz, $CDCl_3$): δ 7.99 (m, 1H), 7.38 (m, 5H), 6.92 (m, 2H), 6.84 (s, 1H), 5.21 (s, 2H), 3.3-3.6 (m, 2H), 3.03 (m, 2H), 2.52 (m, 2H), 2.38 (dt, 1H), 2.34 (t, 1H), 2.20 (m, 1H), 1.58 (s, 3H), 1.52 (s, 3H), 1.43 (s, 9H).

g) (3aR,5S,7S,7aS)-7-(4-Benzyloxycarbonylamino-3-fluoro-benzyl)-2,2-dimethyl-5-oxo-hexahydro-1-oxa-5lambda*4*-thia-3-aza-indene-3-carboxylic acid tert-butyl ester To a solution of (3aR*,7S*,7aS*)-7-(4-benzyloxycarbonylamino-3-fluoro-benzyl)-2,2-dimethyl-tetrahydro-1-oxa-5-thia-3-aza-indene-3-carboxylic acid tert-butyl ester (54.1 g, 102 mmol) in THF (500 mL) was added AcOH (200 mL) and $H_2O_2$ (27.8 g, 50% in $H_2O$, 408 mmol) at 0-5° C. and the reaction mixture was stirred for 16 h at 25° C. The reaction mixture was slowly added to a cold 25% aq. $Na_2S_2O_3$ solution, stirred for 3 h at 0-5° C. and extracted with EtOAc. Combined organic layers were washed with water, saturated $K_2CO_3$ solution and brine, dried over $MgSO_4$, filtered and evaporated. The crude product was filtered through a short plug of ammonia deactivated silicagel and the title compound was obtained as a 3:2 mixture of the (3aR*,5R*,7S*,7aS*)- and (3aR*,5S*,7S*,7aS*)-diastereoisomer after crystallization from $Et_2O$-hexane: TLC (EtOAc-MeOH 19:1) Rf=0.51; HPLC $Rt_A$=2.34 min and 2.38 min; ESIMS $[M+H]^+$=547. Separation of the racemic 3:2 mixture on Chiralpak IC (heptene-EtOH 85:15) and on Chiralpak AD-I (hexane-EtOH-$CHCl_3$ 80:10:10) provided the diastereoisomers (3aR,5R,7S, 7aS)-7-(4-benzyloxycarbonylamino-3-fluoro-benzyl)-2,2-dimethyl-5-oxo-hexa-hydro-1-oxa-5lambda*4*-thia-3-aza-indene-3-carboxylic acid tert-butyl ester (peak 1 on Chiralpak IC) in >98% ee: [α]$_D$−21.5° (c 1, CHCl$_3$); $^1$H NMR (600 MHz, DMSO-d$_6$): δ 9.43 (s, 1H), 7.56 (s, 1H), 7.40 (m, 4H), 7.33 (t, 1H), 7.08 (d, 1H), 6.99 (d, 1H), 5.14 (s, 2H), 3.6-3.8 (m, 2H), 3.40 (t, 1H), 2.92 (m, 2H), 2.6-2.8 (m, 3H), 2.37 (t, 1H), 1.55 (s, 3H), 1.50 (s, 3H), 1.41 (s, 9H) and (3aR,5S,7S,7aS)-7-(4-benzyloxycarbonylamino-3-fluoro-benzyl)-2,2-di-methyl-5-oxo-hexahydro-1-oxa-5lambda*4*-thia-3-aza-indene-3-carboxylic acid tert-butyl ester (peak 2 on Chiralpak IC): $^1$H NMR (600 MHz, DMSO-d$_6$): δ 9.44 (s, 1H), 7.57 (s, 1H), 7.40 (m, 4H), 7.35 (t, 1H), 7.08 (d, 1H), 6.99 (d, 1H), 5.14 (s, 2H), 3.9-4.2 (m, 1H), 3.65 (t, 1H), 2.5-3.5 (m, 6H), 2.25 (m, 1H), 1.51 (s, 6H), 1.42 (s, 9H) followed by the (3aS,5R,7R,7aR)- and (3aS,5S,7R,7aR)-diastereoisomers (peak 3 and peak 4).

h) [4-((1S,3S,4S,5R)-5-Amino-4-hydroxy-1-oxo-hexahydro-1lambda*4*-thiopyran-3-ylmethyl)-2-fluoro-phenyl]-carbamic acid benzyl ester To a solution of (3aR,5S,7S,7aS)-7-(4-benzyloxycarbonylamino-3-fluoro-benzyl)-2,2-dimethyl-5-oxo-hexahydro-1-oxa-5lambda*4*-thia-3-aza-indene-3-carboxylic acid tert-butyl ester (11.0 g, 20.1 mmol) in CH$_2$Cl$_2$ (80 mL) was slowly added under cooling TFA (15.5 mL, 201 mmol) and the reaction mixture was stirred for 3 h at 25° C. The reaction mixture was evaporated to dryness and the dried residue was titurated with diisopropylether. The title compound was obtained after filtration and drying as a light yellow solid: UPLC Rt$_D$=1.077 min; Rt$_E$=0.990 min; ESIMS [M+H]$^+$=407; $^1$H NMR (400 MHz, CD$_3$OD): δ 7.76 (m, 1H), 7.35 (m, 5H), 7.05 (m, 2H), 5.19 (s, 2H), 3.64 (dt, 1H), 3.41 (t, 1H), 3.34 (m, 1H), 3.25 (m, 2H), 2.82 (t, 1H), 2.57 (m, 2H), 2.01 (m, 1H).

i) {4-[(1S,3S,4S,5R)-5-(3-tert-Butyl-benzylamino)-4-hydroxy-1-oxo-hexahydro-1lambda*4*-thiopyran-3-ylmethyl]-2-fluoro-phenyl}-carbamic acid benzyl-ester The title compound was prepared in analogous manner as described for example 1h from [4-((1S,3S,4S,5R)-5-amino-4-hydroxy-1-oxo-hexahydro-1lambda*4*-thiopyran-3-ylmethyl)-2-fluoro-phenyl]-carbamic acid benzyl ester to yield the title compound as a colorless solid: TLC (EtOAc-MeOH 9:1) Rf=0.32; UPLC Rt$_D$=1.457 min; ESIMS [M+H]$^+$=553; $^1$H NMR (600 MHz, DMSO-d$_6$): δ 9.41 (s, 1H), 7.53 (m, 1H), 7.38 (m, 6H), 7.23 (m, 2H), 7.15 (d, 1H), 7.11 (d, 1H), 6.98 (d, 1H), 5.13 (s, 2H), 5.11 (d, 1H), 3.82 (d, 1H), 3.65 (d, 1H), 3.55 (d, 1H), 3.05 (m, 2H), 2.97 (d, 1H), 2.3-2.6 (m, 4H), 1.76 (m, 1H), 1.27 (s, 9H).

j) {4-[(3aR,7S,7aS)-3-(3-tert-Butyl-benzyl)-2,5-di-oxo-octahydro-1-oxa-5lambda*4*-thia-3-aza-inden-7-ylmethyl]-2-fluoro-phenyl}-carbamic acid benzyl ester The title compound was prepared in analogous manner as described for example 1l from {4-[(1S,3S,4S,5R)-5-(3-tert-butyl-benzylamino)-4-hydroxy-1-oxo-hexahydro-1lambda*4*-thio-pyran-3-ylmethyl]-2-fluoro-phenyl}-carbamic acid benzyl-ester to yield the title compound as a colorless solid: TLC (EtOAc-MeOH 9:1) Rf=0.63; UPLC Rt$_D$=1.849 min; ESIMS [M+NH$_4$]$^+$=596; $^1$H NMR (600 MHz, DMSO-d$_6$): δ 9.44 (s, 1H), 7.56 (m, 1H), 7.38 (m, 7H), 7.27 (t, 1H), 7.13 (d, 1H), 7.09 (d, 1H), 6.99 (d, 1H), 5.14 (s, 2H), 4.33 (m, 2H), 4.18 (t, 1H), 3.84 (d, 1H), 3.30 (m, 1H), 3.21 (d, 1H), 2.93 (d, 1H), 2.80 (t, 1H), 2.65 (t, 1H), 2.59 (dd, 1H), 2.48 (m, 1H), 1.27 (s, 9H).

k) {4-[(3aR,7S,7aS)-3-(3-tert-Butyl-benzyl)-2,5,5-trioxo-octahydro-1-oxa-5lambda*6*-thia-3-aza-inden-7-ylmethyl]-2-fluoro-phenyl}-carbamic acid benzyl ester The title compound was prepared in analogous manner as described for example 1f from {4-[(3aR,7S,7aS)-3-(3-tert-butyl-benzyl)-2,5-dioxo-octahydro-1-oxa-5lambda*4*-thia-3-aza-inden-7-ylmethyl]-2-fluoro-phenyl}-carbamic acid benzyl ester to yield the title compound as a colorless solid: UPLC Rt$_D$=1.974 min; ESIMS [M+NH$_4$]$^+$=612; $^1$H NMR (600 MHz, DMSO-d$_6$): δ 9.45 (s, 1H), 7.57 (m, 1H), 7.38 (m, 6H), 7.32 (d, 1H), 7.27 (t, 1H), 7.12 (d, 1H), 7.10 (d, 1H), 6.99 (d, 1H), 5.13 (s, 2H), 4.42 (d, 1H), 4.22 (d, 1H), 4.15 (t, 1H), 3.70 (m, 2H), 3.46 (t, 1H), 3.09 (dd, 1H), 3.02 (dt, 1H), 2.91 (dd, 1H), 2.60 (dd, 1H), 2.53 (m, 1H), 1.26 (s, 9H).

l) (3aR,7S,7aS)-7-(4-Amino-3-fluoro-benzyl)-3-(3-tert-butyl-benzyl)-5,5-dioxo-hexahydro-1-oxa-5lambda*6*-thia-3-aza-inden-2-one A solution of {4-[(3aR,7S,7aS)-3-(3-tert-butyl-benzyl)-2,5,5-trioxo-octahydro-1-oxa-5lambda*6*-thia-3-aza-inden-7-ylmethyl]-2-fluoro-phenyl}-carbamic acid benzyl ester (9.6 g, 15.8 mmol) in THF-MeOH 1:2 (150 mL) was hydrogenated over 10% Pd/C (0.7 g) for 4 h at 45° C. and 1 bar. The catalyst was filtered off over Celite and the filtrate is evaporated to provide the title compound as a colorless solid: TLC (toluene-EtOAc 3:1) Rf=0.26; UPLC Rt$_D$=1.596 min; ESIMS [M+NH$_4$]$^+$=478; $^1$H NMR (600 MHz, DMSO-d$_6$): δ 7.38 (s, 1H), 7.32 (d, 1H), 7.27 (t, 1H), 7.13 (d, 1H), 6.83 (d, 1H), 6.69 (m, 2H), 5.02 (s, 2H), 4.42 (d, 1H), 4.22 (d, 1H), 4.11 (t, 1H), 3.67 (m, 2H), 3.46 (t, 1H), 3.01 (m, 2H), 2.79 (dd, 1H), 2.44 (m, 2H), 1.26 (s, 9H).

m) (3aR,7S,7aS)-7-(4-Amino-3-fluoro-5-iodo-benzyl)-3-(3-tert-butyl-benzyl)-5,5-dioxo-hexahydro-1-oxa-5lambda*6*-thia-3-aza-inden-2-one To a suspension of (3aR,7S,7aS)-7-(4-amino-3-fluoro-benzyl)-3-(3-tert-butyl-benzyl)-5,5-di-oxo-hexahydro-1-oxa-5lambda*6*-thia-3-aza-inden-2-one (3.0 g, 6.4 mmol) in CH$_2$Cl$_2$-MeOH 3:1 (200 mL) was added CaCO$_3$ (1.96 g, 19.2 mmol) and benzyl-trimethylammonium di-chloroiodid (3.47 g, 9.6 mmol) at 25° C. and the reaction mixture was heated at reflux for 16 h. The reaction mixture was washed with H$_2$O, cold 5% aq. Na$_2$S$_2$O$_3$ solution and brine, dried over MgSO$_4$, filtered and evaporated. The title compound was obtained after purification by flash chromatography on silica gel (hexane-CH$_2$Cl$_2$-EtOAc 5:2:2 to 0:2:2) and crystallization from EtOAc-hexane as a light yellow solid: TLC (hexane-EtOAc 1:1) Rf=0.39; HPLC Rt$_A$=2.31 min; ESIMS [M+NH$_4$]$^+$=604; $^1$H NMR (400 MHz, CDCl$_3$): δ 7.36 (d, 1H), 7.29 (m, 2H). 7.17 (s, 1H), 7.10 (d, 1H), 6.79 (d, 1H), 4.53 (d, 1H), 4.33 (d, 1H), 4.15 (s, 2H), 3.85 (dt, 1H), 3.75 (t, 1H), 3.07 (m, 2H), 2.99 (d, 1H), 2.83 (t, 1H), 2.72 (dd, 1H), 2.56 (m, 2H), 1.31 (s, 9H).

n) (3aR,7S,7aS)-7-(4-Amino-3-fluoro-5-vinyl-benzyl)-3-(3-tert-butyl-benzyl)-5,5-dioxo-hexahydro-1-oxa-5lambda*6*-thia-3-aza-inden-2-one To a solution of (3aR,7S,7aS)-7-(4-amino-3-fluoro-5-iodo-benzyl)-3-(3-tert-butyl-benzyl)-5,5-dioxo-hexahydro- 1-oxa-5lambda*6*-thia-3-aza-inden-2-one (0.65 g, 1.1 mmol), NEt$_3$ (0.54 mL, 3.9 mmol) and potassium vinyltrifluoroborate (0.39 g, 2.7 mmol) in n-propanol (20 mL) was added after degassing with argon (1,1'-bis(diphenylphosphino)ferrocene)-dichloro-palladium (0.063 g, 0.078 mmol) and the reaction mixture was heated at 90° C. for 3.5 h. After dilution with saturated NaHCO$_3$ solution the product was extracted with EtOAc. Combined organic extracts were washed with brine, dried over MgSO$_4$, filtered and evaporated. The title compound was obtained after chromatographic purification (Combi Flash, 40 g, hexane-EtOAc 5:95 to 0:100) as a yellow solid: TLC (toluene-EtOAc 3:1) Rf=0.38; UPLC Rt$_D$=1.756 min; ESIMS [M+NH$_4$]$^+$=504; $^1$H NMR (400 MHz, CDCl$_3$): δ 7.38 (d, 1H), 7.30 (m, 2H). 7.09 (d, 1H), 6.80 (s, 1H), 6.72 (dd, 1H), 6.66 (d, 1H), 5.64 (d, 1H), 5.39 (d, 1H), 4.53 (d, 1H), 4.33 (d, 1H), 3.7-3.9 (m, 4H), 3.05 (m, 3H), 2.82 (dd, 1H), 2.72 (m, 1H), 2.60 (m, 2H), 1.31 (s, 9H).

o) (3aR,7S,7aS)-7-(4-Amino-3-ethyl-5-fluoro-benzyl)-3-(3-tert-butyl-benzyl)-5,5-dioxo-hexahydro-1-oxa-5lambda*6*-thia-3-aza-inden-2-one The title compound was prepared in analogous manner as described for example 81) from (3aR,7S,7aS)-7-(4-amino-3-fluoro-5-vinyl-benzyl)-3-(3-tert-butyl-benzyl)-5,5-dioxo-hexahydro-1-oxa-5lambda*6*-thia-3-aza-inden-2-one to yield the title compound as a light yellow solid: TLC (toluene-EtOAc 3:1) Rf=0.38; UPLC Rt$_D$=1.723 min; ESIMS [M+NH$_4$]$^+$=506; $^1$H NMR (600 MHz, DMSO-d$_6$): δ 7.38 (s, 1H), 7.32 (d, 1H), 7.27 (t, 1H), 7.13 (d, 1H), 6.71 (d, 1H), 6.61 (s, 1H), 4.75 (s, 2H), 4.42 (d, 1H), 4.21 (d, 1H), 4.11 (t, 1H), 3.67 (m, 2H), 3.46 (t, 1H), 3.04 (dd, 1H), 2.98 (m, 1H), 2.79 (d, 1H), 2.46 (m, 4H), 1.26 (s, 9H), 1.09 (t, 3H).

p) N-{4-[(3aR,7S,7aS)-3-(3-tert-Butyl-benzyl)-2,5,5-trioxo-octahydro-1-oxa-5lambda*6*-thia-3-aza-inden-7-ylmethyl]-2-ethyl-6-fluoro-phenyl}-2-chloro-acetamide To a solution of (3aR,7S,7aS)-7-(4-amino-3-ethyl-5-fluoro-benzyl)-3-(3-tert-butyl-benzyl)-5,5-dioxo-hexahydro-1-oxa-5lambda*6*-thia-3-aza-inden-2-one (0.245 g, 0.5 mmol) and DIPEA (0.52 mL, 3 mmol) in CH$_2$Cl$_2$ was slowly added a solution of 2-chloroacetylchloride (0.226 g, 2.0 mmol) dissolved in CH$_2$Cl$_2$ (2 mL) at 0-5° C. After stirring for 1 h at 0-5° C. the reaction mixture was poured onto cold saturated NaHCO$_3$ solution and extracted with CH$_2$Cl$_2$. Combined organic extracts were washed with brine, dried over MgSO$_4$, filtered and evaporated. The crude product was dissolved in MeOH, stirred for 0.5 h at 25° C., and evaporated again. The title compound was obtained after chromatographic purification (Combi Flash, 12 g silica gel, hexane-EtOAc) as a light yellow solid: TLC (toluene-EtOAc 1:1) Rf=0.44; UPLC Rt$_D$=1.799 min; ESIMS [M+NH$_4$]$^+$=582; $^1$H NMR (600 MHz, DMSO-d$_6$): δ 9.70 (s, 1H), 7.39 (s, 1H), 7.32 (d, 1H), 7.27 (t, 1H), 7.13 (d, 1H), 6.98 (d, 1H), 6.95 (s, 1H), 4.42 (d, 1H), 4.28 (s, 2H), 4.21 (d, 1H), 4.19 (t, 1H), 3.72 (m, 2H), 3.48 (t, 1H), 3.14 (dd, 1H), 2.98 (m, 2H), 2.55 (m, 4H), 1.26 (s, 9H), 1.08 (t, 3H).

q) N-{4-[(3aR,7S,7aS)-3-(3-tert-Butyl-benzyl)-2,5,5-trioxo-octahydro-1-oxa-5lambda*6*-thia-3-aza-inden-7-ylmethyl]-2-ethyl-6-fluoro-phenyl}-2-ethylamino-acetamide To a solution of N-{4-[(3aR,7S,7aS)-3-(3-tert-butyl-benzyl)-2,5,5-trioxo-octahydro-1-oxa-5lambda*6*-thia-3-aza-inden-7-ylmethyl]-2-ethyl-6-fluoro-phenyl}-2-chloro-acetamide 0.087 g, 0.15 mmol) in DMF (2 mL) was added a 4M solution of ethylamine in DMF (0.1 mL, 0.4 mmol) and the reaction mixture was kept for 2 days at 25° C. After evaporation, the product was dissolved in water and extracted with EtOAc. Combined organic extracts were washed with brine, dried over MgSO$_4$, filtered and evaporated to provide a yellow foam: TLC (EtOAc-MeOH 9:1) Rf=0.25; UPLC Rt$_D$=1.443 min; ESIMS [M+NH$_4$]$^+$=574.

r) N-{4-[(3S,4S,5R)-5-(3-tert-Butyl-benzylamino)-4-hydroxy-1,1-dioxo-hexahydro-1lambda*6*-thiopyran-3-ylmethyl]-2-ethyl-6-fluoro-phenyl}-2-ethylamino-acetamide The title compound was prepared in analogous manner as described for example 1o from N-{4-[(3aR,7S,7aS)-3-(3-tert-butyl-benzyl)-2,5,5-trioxo-octahydro-1-oxa-5lambda*6*-thia-3-aza-inden-7-ylmethyl]-2-ethyl-6-fluoro-phenyl}-2-ethylamino-acetamide to yield after preparative HPLC (Sunfire C18 OBD 5 μm, 100×30, 5-50% ACN in water+0.1% TFA gradient, 25 min) the title compound as a light yellow amorphous solid: UPLC Rt$_D$=1.084 min; ESIMS [M+H]$^+$=548; $^1$H NMR (600 MHz, DMSO-d$_6$+TFA): δ 9.96 (s, 1H), 9.70 (s, 1H), 9.0 (s, 1H), 8.90 (s, 1H), 7.63 (s, 1H), 7.44 (m, 1H), 7.37 (m, 1H), 6.98 (d, 1H), 6.95 (s, 1H), 4.26 (m, 2H), 4.02 (m, 2H), 3.84 (d, 1H), 3.66 (dd, 1H), 3.61 (dd, 1H), 3.1-3.3 (m 3H), 3.0 (m, 2H), 2.78 (d, 1H), 2.50 (m, 3H), 2.11 (m, 1H), 1.26 (s, 9H), 1.19 (t, 3H), 1.10 (t, 3H).

Example 9

N-{4-[(3S,4S,5R)-5-(3-tert-Butyl-benzylamino)-4-hydroxy-1,1-dioxo-hexa-hydro-1lambda*6*-thiopyran-3-ylmethyl]-2-ethyl-6-fluoro-phenyl}-2-dimethylamino-acetamide dihydrochloride The title compound was prepared in analogous manner as described for examples 8q) and 8r) from N-{4-[(3aR,7S,7aS)-3-(3-tert-butyl-benzyl)-2,5,5-trioxo-octahydro-1-oxa-5lambda*6*-thia-3-aza-inden-7-ylmethyl]-2-ethyl-6-fluoro-phenyl}-2-chloro-acetamide to yield after preparative HPLC purification (Sunfire C18 OBD 5 μm, 100×30, 5-50% ACN in water+0.1% TFA gradient, 25 min) the title compound as a light yellow amorphous solid: TLC (EtOAc-MeOH 9:1) Rf=0.36; UPLC Rt$_D$=1.136 min; ESIMS [M+H]$^+$=548; $^1$H NMR (600 MHz, DMSO-d$_6$): δ10.22 (s, 1H, 10.07 (s, 1H), 9.97 (s, 1H), 9.11 (s, 1H), 7.68 (s, 1H), 7.44 (dd, 1H), 7.37 (m, 2H), 7.01 (d, 1H), 6.97 (s, 1H), 6.29 (s, 1H), 4.24 (m, 4H), 3.89 (d, 1H), 3.70 (m, 2H), 3.26 (dd, 1H), 3.18 (m 2H), 2.85 (s, 6H), 2.76 (dd, 1H), 2.55 (m, 3H), 2.10 (m, 1H), 1.29 (s, 9H), 1.09 (t, 3H).

Example 10

N-{4-[(3S,4S,5R)-5-(3-tert-Butyl-benzylamino)-4-hydroxy-1,1-dioxo-hexa-hydro-1lambda*6*-thiopyran-3-ylmethyl]-2-ethyl-6-fluoro-phenyl}-2-methoxy-acetamide hydrochloride The title compound was prepared in analogous manner as described for example 8q and 8r from N-{4-[(3aR,7S,7aS)-3-(3-tert-butyl-benzyl)-2,5,5-trioxo-octahydro-1-oxa-5lambda*6*-thia-3-aza-inden-7-ylmethyl]-2-ethyl-6-fluoro-phenyl}-2-chloro-acetamide and methoxy-acetyl chloride to yield after preparative HPLC purification (Sunfire C18 OBD 5 μm, 100×30, 5-100% ACN in water+0.1% TFA gradient, 25 min) the title compound as a light yellow amorphous solid: TLC (EtOAc-MeOH 9:1) Rf=0.56; UPLC Rt$_D$=1.298 min; ESIMS [M+H]$^+$=535; $^1$H NMR (600 MHz, DMSO-d$_6$): δ 9.99 (s, 1H), 9.31 (s, 1H), 9.08 (s, 1H), 7.68 (s, 1H), 7.44 (dd, 1H), 7.39 (m, 3H), 6.96 (d, 1H), 6.92 (s, 1H), 6.23 (s, 1H), 4.23 (m, 4H), 4.01 (s, 2H), 3.91 (d, 1H), 3.66 (m, 2H), 3.38 (s, 3H), 3.26 (dd, 1H), 3.17 (m, 2H), 2.76 (dd, 1H), 2.52 (m, 3H), 2.10 (m, 1H), 1.29 (s, 9H), 1.08 (t, 3H).

Example 11

N-{4-[(3S,4S,5R)-5-(3-tert-Butyl-benzylamino)-4-hydroxy-1,1-dioxo-hexa-hydro-1lambda*6*-thiopyran-3-ylmethyl]-2-chloro-6-fluoro-phenyl}-2-dimethylamino-acetamide dihydrochloride a) (3aR,7S,7aS)-7-(4-Amino-3-chloro-5-fluoro-benzyl)-3-(3-tert-butyl-benzyl)-5,5-dioxo-hexahydro-1-oxa-5lambda*6*-thia-3-aza-inden-2-one A solution of (3aR,7S,7aS)-7-(4-amino-3-fluoro-benzyl)-3-(3-tert-butyl-benzyl)-5,5-dioxo-hexahydro-1-oxa-5lambda*6*-thia-3-aza-inden-2-one (4.0 g, 8.69 mmol, example 81) and N-chlorosuccinimide (1.276 g, 9.55 mmol) in ACN (130 mL) was heated at reflux for 2 h. The reaction mixture was evaporated and the residue was purified by chromatography (Combi Flash, 120 g silicagel, hexane-EtOAc) to provide the title compound as a colorless solid: TLC (toluene-EtOAc 3:1) Rf=0.42; UPLC Rt$_D$=1.887 min; [M+NH$_4$]$^+$=512, 514; $^1$H NMR (600 MHz, DMSO-d$_6$): δ 7.38 (s, 1H), 7.32 (d, 1H), 7.27 (t, 1H), 7.13 (d, 1H), 6.93 (s, 1H), 6.89 (d, 1H), 5.28 (s, 2H), 4.42 (d, 1H), 4.21 (d, 1H), 4.11 (t, 1H), 3.68 (m, 2H), 3.46 (t, 1H), 3.05 (m, 2H), 2.78 (d, 1H), 2.50 (m, 2H), 1.26 (s, 9H).

b) N-{4-[(3aR,7S,7aS)-3-(3-tert-Butyl-benzyl)-2,5,5-trioxo-octahydro-1-oxa-5lambda*6*-thia-3-aza-inden-7-ylmethyl]-2-ethyl-6-fluoro-phenyl}-2-chloro-acetamide The title compound was prepared in analogous manner as described in example 8p) from (3aR,7S,7aS)-7-(4-Amino-3-chloro-5-fluoro-benzyl)-3-(3-tert-butyl-benzyl)-5,5-dioxo-hexa-hydro-1-oxa-5lambda*6*-thia-3-aza-inden-2-one: TLC (toluene-EtOAc 1:1) Rf=0.41; UPLC Rt$_D$=1.729 min; ESIMS [M+NH$_4$]$^+$=588, 590; $^1$H NMR (600 MHz, DMSO-d$_6$): δ 10.06 (s, 1H), 7.39 (s, 1H), 7.32 (d, 1H), 7.29 (s, 1H), 7.28 (t, 1H), 7.21 (d, 1H), 7.13 (d, 1H), 4.43 (d, 1H), 4.33 (s, 2H), 4.22 (d, 1H), 4.19 (t, 1H), 3.75 (d, 1H), 3.70 (dd, 1H), 3.48 (t, 1H), 3.15 (dd, 1H), 2.98 (d, 1H), 2.95 (d, 1H), 2.60 (m, 2H), 1.27 (s, 9H).

c) N-{4-[(3aR,7S,7aS)-3-(3-tert-Butyl-benzyl)-2,5,5-trioxo-octahydro-1-oxa-5lambda*6*-thia-3-aza-inden-7-ylmethyl]-2-chloro-6-fluoro-phenyl}-2-dimethylamino-acetamide The title compound was prepared in analogous manner as described in example 8q) from N-{4-[(3aR,7S,7aS)-3-(3-tert-butyl-benzyl)-2,5,5-trioxo-octahydro-1-oxa-5lambda*6*-thia-3-aza-inden-7-ylmethyl]-2-ethyl-6-fluoro-phenyl}-2-chloro-acetamide: TLC (EtOAc-MeOH 9:1) Rf=0.57; UPLC Rt$_D$=1.487 min; ESIMS [M+H]$^+$=580, 582.

d) N-{4-[(3S,4S,5R)-5-(3-tert-Butyl-benzylamino)-4-hydroxy-1,1-dioxo-hexahydro-1lambda*6*-thiopyran-3-ylmethyl]-2-chloro-6-fluoro-phenyl}-2-dimethylamino-acetamide dihydrochloride The title compound was prepared in analogous manner as described in example 8r) from N-{4-[(3aR,7S,7aS)-3-(3-tert-butyl-benzyl)-2,5,5-trioxo-octahydro-1-oxa-5lambda*6*-thia-3-aza-inden-7-ylmethyl]-2-chloro-6-fluoro-phenyl}-2-dimethylamino-acetamide to provide after preparative HPLC purification (Sunfire C18 OBD 5 μm, 100×30, 5-40% ACN in water+0.1% TFA gradient, 25 min) the title compound as a colorless amorphous solid: TLC (EtOAc-MeOH 9:1) Rf=0.38; UPLC Rt$_D$=1.019 min; ESIMS [M+H]$^+$=554, 556; $^1$H NMR (600 MHz, DMSO-d$_6$): δ10.57 (s, 1H), 10.03 (s, 1H), 9.11 (s, 1H), 7.68 (s, 1H), 7.44 (dd, 1H), 7.39 (d, 1H), 7.36 (t, 1H), 7.32 (s, 1H), 7.25 (d, 1H), 6.28 (s, 1H), 4.25 (m, 4H), 3.89 (d, 1H), 3.66 (m, 2H), 3.27 (dd, 1H), 3.17 (m, 2H), 2.89 (m, 1H), 2.85 (s, 6H), 2.58 (dd, 1H), 2.15 (m, 1H), 1.29 (s, 9H).

Examples 12 to 16

The compounds listed in Table 1 were prepared by a procedure analogous to that used in example 8.

TABLE 1

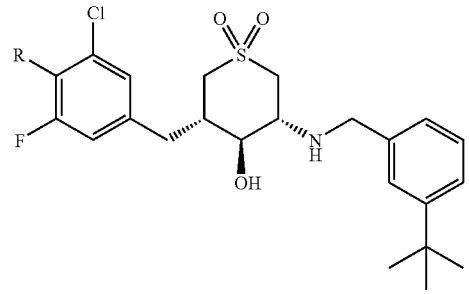

| Example | R | Chromatography Method | Chromatography Rt [min] | ESIMS [M + H]$^+$ |
|---------|---|------------------------|--------------------------|---------------------|
| 12 | | E | 1.075 | 554, 556 |

TABLE 1-continued

| Example | R | Chromatography Method | Chromatography Rt [min] | ESIMS [M + H]+ |
|---|---|---|---|---|
| 13 | (methylamino-acetamide group) | E | 1.012 | 540, 542 |
| 14 | (cyclopropylamino-acetamide group) | E | 1.036 | 566, 568 |
| 15 | (tert-butylamino-acetamide group) | E | 1.070 | 582, 584 |
| 16 | (piperidinyl-acetamide group) | E | 1.064 | 594, 596 |

Example 17

(3R,4S,5S)-3-(3-tert-Butyl-benzylamino)-5-[3-chloro-4-(2-cyclopropyl-amino-ethylamino)-5-fluoro-benzyl]-1,1-dioxo-hexahydro-1lambda*6*-thiopyran-4-ol hydrochloride To a solution of N-{4-[(3S,4S,5R)-5-(3-tert-butyl-benzylamino)-4-hydroxy-1,1-dioxo-hexa-hydro-1lambda*6*-thiopyran-3-ylmethyl]-2-chloro-6-fluoro-phenyl}-2-cyclopropylamino-acetamide (example 14) (0.17 g, 0.3 mmol) in THF (5 mL) was added borane methylsulfide-complex (0.6 mL, 6 mmol) at 25° C. The mixture was heated at 60° C. for 16 h. The reaction was carefully quenched with MeOH, added to 2N HCl and stirred for 16 h at 25° C. After basification with $K_2CO_3$ the aq. phase was extracted with EtOAc. Combined organic layers were washed with brine, dried over $Na_2SO_4$, filtered and concentrated. The product was purified by preparative HPLC (Sunfire C18 OBD 5 μm, 100×30, 5-40% ACN in water+0.1% TFA gradient, 25 min) and converted into the hydrochloride salt to provide the title compound as a colorless amorphous solid: TLC (EtOAc-MeOH 9:1) Rf=0.40; UPLC $Rt_D$=1.093 min; ESIMS [M+H]+=552, 554; $^1$H NMR (600 MHz, DMSO-$d_6$): δ 10.57 (s, 1H), 10.03 (s, 1H), 9.08 (s, 2H), 7.67 (s, 1H), 7.44 (dd, 1H), 7.37 (m, 2H), 7.05 (s, 1H), 7.00 (d, 1H), 6.20 (s, 1H), 4.23 (m, 2H), 3.89 (d, 1H), 3.5-3.7 (m, 4H), 3.17 (m, 4H), 3.02 (d, 1H), 2.83 (m, 1H), 2.74 (s, 1H), 2.42 (dd, 1H), 2.04 (m, 1H), 1.29 (s, 9H), 0.85 (m, 1H), 0.74 (m, 1H).

Example 18

2-Amino-N-butyl-5-[3S*,4S*,5R*)-5-(3-tert-butyl-benzylamino)-4-hydroxy-1,1-dioxo-hexahydro-1lambda*6*-thiopyran-3-ylmethyl]-benzamide a) 5-[(3S*,4S*,5R*)-5-(3-tert-Butyl-benzylamino)-4-hydroxy-1,1-dioxo-hexahydro-1lambda*6*-thiopyran-3-ylmethyl]-2-nitro-benzoic acid A mixture of 5-[(3S*,4S*,5R*)-5-(3-tert-butyl-benzylamino)-4-hydroxy-1,1-dioxo-hexahydro-1lambda*6*-thiopyran-3-ylmethyl]-2-nitro-benzoic acid methyl ester (434 mg, 0.86 mmol; prepared from methyl 5-(bromomethyl)-2-nitrobenzoate using a procedure analogous to that used in example 1) and NaOH (30% in $H_2O$, 1 mL, 7.4 mmol) in anhydrous THF (5 mL) was stirred at 80° C. for 1 h. The reaction mixture was diluted with EtOAc and quenched with 2N aq. HCl to pH 2. The phases were separated and the aqueous phase was extracted with EtOAc. The combined organic extracts were washed with brine, dried over $Na_2SO_4$, filtered and evaporated to yield the product as a yellow gum: ESIMS [M+H]+=491, LCMS $Rt_f$=0.97 min.

b) 2-Nitro-N-butyl-5-[(3S*,4S*,5R*)-5-(3-tert-butyl-benzylamino)-4-hydroxy-1,1-dioxo-hexahydro-1lambda*6*-thiopyran-3-ylmethyl]-benzamide Butylamine (0.0305 mL, 0.306 mmol) was added to a mixture of 5-[(3S*,4S*,5R*)-5-(3-tert-butyl-benzylamino)-

4-hydroxy-1,1-dioxo-hexahydro-1lambda*6*-thiopyran-3-ylmethyl]-2-nitro-benzoic acid (0.05 g, 0.101 mmol), HOBt (0.0165 g, 0.122 mmol), EDC (HCl salt, 0.024 g, 0.122 mmol) in DMF (1.5 mL) and was stirred at room temperature over night. The reaction mixture was quenched with saturated NaHCO₃ solution and diluted with EtOAc. The phases were separated and the aqueous phase was extracted with EtOAc. The combined organic extracts were washed with brine, dried over Na₂SO₄, filtered and evaporated to yield the product as a yellow gum. The title compound was obtained after flash-chromatography on silica gel (EtOAc-MeOH 10:1) as a colorless gum: ESIMS [M+H]⁺=546, LCMS Rt₁=1.09 min; ¹H NMR (360 MHz, CDCl₃): δ 7.91 (d, 1H), 7.3-7.2 (m, 5H), 7.05 (d, 1H), 5.90 (m, 1H), 4.10 (s broad, 1H), 3.82 (d, 1H), 3.68 (d, 1H), 3.40-3.28 (m, 3H), 3.15 (dd, 1H), 3.1-2.9 (m, 2H), 2.80 (m, 2H), 2.70-2.58 (m, 2H), 2.36 (m, 1H), 1.55 (m, 2H), 1.40-1.30 (m, 2H), 1.25 (s, 9H), 1.19 (m, 1H), 0.9 (t, 3H).

c) 2-Amino-N-butyl-5-[(3S*,4S*,5R*)-5-(3-tert-butyl-benzylamino)-4-hydroxy-1,1-dioxo-hexahydro-1lambda*6*-thiopyran-3-ylmethyl]-benzamide The title compound was prepared in analogous manner as described for example 1i from 2-nitro-N-butyl-5-[(3S*,4S*,5R*)-5-(3-tert-butyl-benzylamino)-4-hydroxy-1,1-dioxo-hexahydro-1lambda*6*-thiopyran-3-ylmethyl]-benzamide: HPLC Rt_{B2}=14.68 min; ESIMS [M+H]⁺=516; ¹H NMR (360 MHz, CDCl₃): δ 7.3-7.2 (m, 3H), 7.08-7.02 (m, 2H), 6.91 (dd, 1H), 6.55 (d, 1H), 5.95 (t, 1H), 5.32 (s, 2H), 4.00 (s, 1H, OH), 3.84 (d, 1H), 3.68 (d, 1H), 3.38-3.28 (m, 3H), 3.10-2.82 (m, 4H), 2.65-2.54 (m, 3H), 2.25 (m, 1H), 1.55-1.30 (m, 4H), 1.25 (s, 9H), 1.19 (m, 1H), 0.9 (t, 3H).

Examples 19 to 23

The compounds listed in Table 2 were prepared by a procedure analogous to that used in example 18.

TABLE 2

| Example | R | Chromatography Method | Chromatography Rt [min] | ESIMS [M + H]⁺ |
|---------|---|----------------------|------------------------|----------------|
| 19 | ⌇NH | B | 14.75 | 488 |
| 20 | ⌇NH | F | 6.17 | 502 |
| 21 | cyclopropyl-CH₂-NH | G | 3.38 | 514 |
| 22 | F-CH₂CH₂-NH | F | 6.10 | 506 |
| 23 | F₃C-CH₂-NH | F | 6.53 | 542 |

Example 24

(3S,4S,5R)-3-[4-Amino-3-fluoro-5-(2-methoxy-ethoxy)-benzyl]-5-(3-tert-butyl-benzylamino)-1,1-dioxo-hexahydro-1lambda*6*-thiopyran-4-ol dihydrochloride a) 3,5-Difluoro-4-nitro-benzoic acid methyl ester Thionylchloride (1.0 mol, 134 mL) was added to MeOH (400 mL) at −10° C. to −20° C. over a period of 0.5 h. To this solution was added 3,5-difluoro-4-nitro-benzonitrile (33.5 g, 180 mmol) and the reaction mixture was allowed to warm to 25° C. and stirred overnight at 25° C. Afterwards the temperature was slowly increased to 50° C. over 2 h and the evolving gas was trapped in a gas washer. Finally the reaction mixture was heated at reflux for 2 h. The cooled reaction mixture was filtered and concentrated. The crude product was dissolved in EtOAc and washed with cold aq. NaHCO₃ solution and brine, dried over MsSO₄, filtered and concentrated. The residue was crystallized from EtOAc-hexane to yield the title compound as an orange solid: TLC (hexane-EtOAc 3:1) Rf=0.38; HPLC Rt_A=1.74 min; ¹H NMR (400 MHz, CDCl₃): δ 7.76 (d, 2H), 3.98 (s, 3H).

b) (3,5-Difluoro-4-nitro-phenyl)-methanol

To a solution of 3,5-difluoro-4-nitro-benzoic acid methyl ester (10.95 g, 50 mmol) in THF (250 mL) was added at 0-5°

C. under argon a 1M DIBAL solution in hexane (165 mL, 165 mmol) within 1.5 h. The reaction mixture was stirred for 2.5 h at 0-5° C. before it was added to 200 mL cold 1M aq. potassium tartrate solution under ice-cooling. After stirring the reaction mixture for 0.5 h at 25° C. the aqueous phase was extracted with EtOAc. Combined organic extracts were washed with brine, dried over $MgSO_4$, filtered and evaporated to provide the title compound as a yellow solid: TLC (hexane-EtOAc 1.1) Rf=0.35; HPLC $Rt_A$=1.31 min; $^1$H NMR (400 MHz, $CDCl_3$): δ 7.12 (d, 2H), 4.77 (s, 2H).

c) 5-Bromomethyl-1,3-difluoro-2-nitro-benzene

To a solution of $PBr_3$ (7.04 mL, 73 mmol) in $Et_2O$ (200 mL) is added under argon at 0° C. a solution of (3,5-difluoro-4-nitro-phenyl)-methanol (9.3 g, 48.7 mmol) in $Et_2O$ (200 mL). The reaction mixture was allowed to warm to 25° C. and stirred for 24 h at 25° C. After the addition of MeOH (5 mL) at 0° C., the reaction mixture was poured onto cold aq. $NaHCO_3$ solution and the product was extracted with EtOAc. Combined organic extracts were washed with saturated $NaHCO_3$ solution and brine, dried over $MgSO_4$, filtered and concentrated to provide the title compound after filtration through a plug of silicagel with hexane-EtOAc 3:1 as a yellow solid: TLC (hexane-EtOAc 3:1) Rf=0.40; HPLC $Rt_A$=2.01 min; $^1$H NMR (400 MHz, $CDCl_3$): δ 7.14 (d, 2H), 4.40 (s, 2H).

d) 5-tert-Butoxycarbonylamino-3-(3,5-difluoro-4-nitro-benzyl)-4-oxo-tetrahydro-thio-pyran-3-carboxylic acid allyl ester To a solution of 5-bromomethyl-1,3-difluoro-2-nitro-benzene (11.88 g, 46 mmol) in acetone (400 mL) was added 5-tert-butoxycarbonylamino-4-oxo-4-tetrahydro-thiopyran-3-carboxylic acid allyl ester (14.02 g, 44 mmol, example 1b) and pulverized $K_2CO_3$ (18.4 g, 132 mmol). The reaction mixture was stirred for 2.5 h at 25-30° C., filtered and evaporated. The residual oil was taken up in EtOAc, washed with brine, dried over $MgSO_4$, decolorized with charcoal, filtered and evaporated to provide the title compound as a orange oil suitable for use in the next step: TLC (hexane-EtOAc 3:1) Rf=0.25; HPLC $Rt_A$=2.36 min; ESIMS $[M+NH_4]^+$=504.

e) [(3R*,5S*)-5-(3,5-Difluoro 4-nitro-benzyl)-4-oxo-tetrahydro-thiopyran-3-yl]-carbamic acid tert-butyl ester To a degassed solution of 5-tert-butoxycarbonylamino-3-(3,5-difluoro-4-nitro-benzyl)-4-oxo-tetrahydro-thiopyran-3-carboxylic acid allyl ester (30.4 g, 62.4 mmol) in THF (300 mL) was added under argon 5,5-dimethyl-cyclohexane-1,3-dione (11.6 g, 81.2 mmol) and $Pd(PPh_3)_4$ (0.76 g, 0.62 mmol) and the reaction mixture was stirred for 3 h at 25° C. The reaction mixture was poured into aq. $NaH_2PO_4$ solution, concentrated and extracted with EtOAc. Combined organic extracts were washed with brine, dried over $MgSO_4$, filtered and evaporated. The crystallized product containing the (3R*,5S*)-diastereoisomer was filtered off and dried. The mother liquor containing a larger amount of the (3S*,5S*)-diastereoisomer was dissolved in THF and equilibrated with a catalytic amount of DBU to the (3R*,5S*)-diastereoisomer for 16 h at 25° C. After removal of the THF the (3R*,5S*)-diastereoisomer was crystallized from $Et_2O$-hexane to provide more of the title compound as white crystals: TLC (hexane-EtOAc 3:1) Rf=0.23; HPLC $Rt_A$=2.23 min; ESIMS $[M+NH_4]^+$=420; $^1$H NMR (400 MHz, $CDCl_3$): δ 6.96 (d, 2H), 5.65 (d, 1H), 4.55 (m, 1H), 3.40 (m, 1H), 3.25 (dd, 1H), 3.14 (m, 1H), 2.86 (m, 1H), 2.6-2.75 (m, 3H), 1.44 (s, 9H).

f) [(3R,4S,5S)-5-(3,5-Difluoro-4-nitro-benzyl)-4-hydroxy-tetrahydro-thiopyran-3-yl]-carbamic acid tert-butyl ester To a suspension of $LiAlH_4$ (2.137 g, 53.5 mmol) in anhydrous THF (200 mL) was added under argon a solution of [(3R*,5S*)-5-(3,5-difluoro-4-nitro-benzyl)-4-oxo-tetrahydro-thiopyran-3-yl]-carbamic acid tert-butyl ester (19.56 g, 48.6 mmol) in anhydrous THF (300 mL) below −70° C. over a period of 2 h. After stirring for 5 h at −78° C. the reaction was quenched with 4.2 mL $H_2O$ at 0° C., 4.2 mL 4N aq. NaOH and after stirring for 30 min an additional 12.6 mL $H_2O$ were added. After addition of $MgSO_4$, the reaction mixture was filtered over Celite, and the colorless filtrate was evaporated. The title compound was obtained after two crystallizations from EtOH as a single diastereoisomer. The racemate [(3R*,4S*,5S*)-5-(3,5-difluoro-4-nitro-benzyl)-4-hydroxy-tetrahydro-thiopyran-3-yl]-carbamic acid tert-butyl ester was separated by preparative HPLC on Chiralpak AD-I (5×20 cm) with hexane-AcOEt-iPrOH 80:15:5 to yield the (3R,4S,5S)-diastereoisomer with >99% ee (peak 1) and the (3S,4R,5R)-diastereoisomer with >98% ee as light yellow crystalline solid: TLC (hexane-EtOAc 1:1) Rf=0.38; HPLC $Rt_A$=2.05 min; ESIMS [M+H-isobutylene]$^+$=349; $^1$H NMR (400 MHz, $CDCl_3$): δ 6.92 (d, 2H), 5.55 (d, 1H), 4.34 (m, 1H), 3.54 (m, 1H), 3.22 (dd, 1H), 2.91 (m, 1H), 2.75 (m, 1H), 2.46 (dd, 1H), 2.36 (dd, 1H), 2.26 (m, 2H), 2.03 (m, 1H), 1.36 (s, 9H).

g) [(3R,4S,5S)-5-(3,5-Difluoro-4-nitro-benzyl)-4-hydroxy-1,1-dioxo-hexahydro-1lambda*6*-thiopyran-3-yl]-carbamic acid tert-butyl ester To a solution of [(3R,4S,5S)-5-(3,5-difluoro-4-nitro-benzyl)-4-hydroxy-tetrahydro-thiopyran-3-yl]-carbamic acid tert-butyl ester (2.05 g, 4.9 mmol) in THF-water 1:1 (60 mL) was added oxone (6.52 g, 10.3 mmol). After stirring the reaction mixture for 2 h at 40° C., 2 g NaOAc and 2 g sodium metabisulfite were added. The reaction mixture was stirred for 0.5 h, basified with saturated aq. $K_2CO_3$ solution and the product was extracted with EtOAc. Combined organic extracts were washed with brine, dried over $MgSO_4$, filtered and concentrated to provide the title compound after crystallization from THF-hexane as yellow crystals: TLC (hexane-THF 1:1) Rf=0.23; HPLC $Rt_A$=1.76 min; ESIMS $[M+NH_4]^+$=454; $^1$H NMR (600 MHz, DMSO-$d_6$): δ 7.32 (d, 2H), 6.91 (d, 1H), 3.73 (m, 1H), 3.0-3.2 (m, 5H), 2.94 (m, 1H), 2.74 (dd, 1H), 2.18 (m, 1H), 1.38 (s, 9H).

h) (3R,4S,5S)-3-Amino-5-(3,5-difluoro-4-nitro-benzyl)-1,1-dioxo-hexahydro-1lambda*6*-thiopyran-4-ol hydrochloride To [(3R,4S,5S)-5-(3,5-difluoro-4-nitro-benzyl)-4-hydroxy-1,1-dioxo-hexahydro-1lambda*6*-thiopyran-3-yl]-carbamic acid tert-butyl ester (0.873 g, 2 mmol) was added 4N HCl in dioxane (5 mL) and the reaction mixture was stirred for 3 h at 40° C. After evaporation the residue was stirred with $Et_2O$, filtered and dried to provide the title compound as a beige solid: TLC ($CH_2Cl_2$-MeOH-AcOH-$H_2O$ 180:20:2:1) Rf=0.13; HPLC $Rt_A$=1.22 min; ESIMS $[M+H]^+$=337; $^1$H NMR (600 MHz, DMSO-$d_6$): δ 8.34 (s, 3H), 7.37 (d, 2H), 6.14 (d, 1H), 3.3-3.5 (m, 4H), 3.31 (d, 1H), 3.22 (d, 1H), 3.12 (m, 1H), 2.74 (dd, 1H), 2.26 (m, 1H).

i) (3R,4S,5S)-3-(3-tert-Butyl-benzylamino)-5-(3,5-difluoro-4-nitro-benzyl)-1-dioxo-hexahydro-1lambda*6*-thiopyran-4-ol The title compound was prepared in analogous manner as described for example 1h) from (3R,4S,5S)-3-amino-5-(3,5-difluoro-4-nitro-benzyl)-1,1-dioxo-hexahydro-1lambda*6*-thio-pyran-4-ol hydrochloride to yield the title compound as a white solid: TLC (EtOAc) Rf=0.27; HPLC $Rt_A$=1.90 min; ESIMS $[M+H]^+$=483; $^1$H NMR (400 MHz, $CD_3OD$): δ 7.41 (m, 1H), 7.1-7.35 (m, 5H), 3.88 (d, 1H), 3.72 (d, 1H), 3.42 (m, 1H), 3.26 (dd, 1H), 3.21 (d, 1H), 2.9-3.1 (m, 3H), 2.85 (m, 1H), 2.72 (dd, 1H), 2.31 (m, 1H), 1.34 (s, 9H).

j) (3R,4S,5S)-3-(3-tert-Butyl-benzylamino)-5-[3-fluoro-4-nitro-5-(2,2,2-trifluoro-ethoxy)-benzyl]-1,1-dioxo-hexahydro-1lambda*6*-thiopyran-4-ol To a suspension of (3R,4S,5S)-3-(3-tert-butyl-benzylamino)-5-(3,5-difluoro-4-nitro-benzyl)-1,1-dioxo-hexahydro-1lambda*6*-thiopyran-4-ol (0.08 g, 0.16 mmol) in 2-methoxyethanol (1 mL) was added pulverized KOH and (0.011 g, 0.18 mmol) and the resulting reaction mixture was heated in the microwave for 0.5 h at 100° C. The solvent was removed under reduced pressure and the title compound was obtained as a yellow foam suitable for use in the next step: TLC (EtOAc) Rf=0.32; HPLC $Rt_A$=1.93 min; ESIMS $[M+H]^+$=539.

k) (3S,4S,5R)-3-[4-Amino-3-fluoro-5-(2-methoxy-ethoxy)-benzyl]-5-(3-tert-butyl-benzylamino)-1,1-dioxo-hexahydro-1lambda*6*-thiopyran-4-ol dihydrochloride To a solution of (3R,4S,5S)-3-(3-tert-butyl-benzylamino)-5-[3-fluoro-4-nitro-5-(2,2,2-trifluoro-ethoxy)-benzyl]-1,1-dioxo-hexahydro-1lambda*6*-thiopyran-4-ol (0.082 g, 0.166 mol) in MeOH (5 mL) was added $NiCl_2-6H_2O$ (0.038 g, 0.155 mmol) and at 0° C. $NaBH_4$ (0.024 g, 0.62 mmol) in two portions. After stirring for 1 h at 0-5° C. the reaction was quenched by addition of 1N aq. HCl. The reaction mixture was stirred for 0.5 h at 25° C. and extracted with EtOAc. The combined organic extracts were washed with brine, dried over $MgSO_4$, filtered and concentrated. Chromatographic purification (Combi-Flash, 4 g, hexane-THF 90:10 to 10:90 containing 0.5% $NEt_3$) provided a pure yellow oil which was converted into the hydrochloride salt with 1N HCl in $Et_2O$ to yield the title compound as a white amorphous solid: TLC (hexane-THF 2:3) Rf=0.22; HPLC $Rt_A$=1.56 min; ESIMS $[M+NH_4]^+$=509; $^1$H NMR (600 MHz, DMSO-$d_6$): δ 9.89 (s, 1H), 9.08 (s, 1H), 7.67 (s, 1H), 7.43 (m, 1H), 7.38 (m, 2H), 6.62 (m, 2H), 6.18 (s, 1H), 4.24 (m, 2H), 4.14 (m, 2H), 3.82 (m, 1H), 3.3-3.7 (m, 5H), 3.29 (s, 3H), 3.24 (m, 2H), 3.03 (dd, 1H), 2.77 (m, 1H), 2.40 (dd, 1H), 2.04 (m, 1H), 1.35 (d, 9H).

Example 25

(3S,4S,5R)-3-[4-Amino-3-fluoro-5-(oxetan-3-yloxy)-benzyl]-5-(3-tert-butyl-benzylamino)-1,1-dioxo-hexahydro-1lambda*6*-thiopyran-4-ol The title compound was prepared in analogous manner as described for example 24 from (3R,4S,5S)-3-(3-tert-butyl-benzylamino)-5-(3,5-difluoro-4-nitro-benzyl)-1,1-dioxo-hexahydro-1lambda*6*-thiopyran-4-ol to provide the title compound after preparative HPLC (Sunfire C18 OBD 5 μm, 100×30, 5-100% ACN in water+0.1% TFA gradient, 25 min) as a colorless amorphous solid: HPLC $Rt_A$=1.61 min; ESIMS $[M+H]^+$=507; $^1$H NMR (600 MHz, DMSO-$d_6$): δ 7.35 (s, 1H), 7.24 (m, 2H), 7.14 (d, 1H), 6.54 (d, 1H), 6.11 (s, 1H), 5.22 (m, 1H), 5.15 (d, 1H), 4.87 (m, 2H), 4.65 (s, 2H), 4.57 (m, 2H), 3.80 (d, 1H), 3.62 (d, 1H), 3.38 (m, 1H), 3.12 (m, 1H), 2.97 (dd, 1H), 2.88 (m, 2H), 2.77 (m, 1H), 2.69 (m, 1H), 2.40 (m, 1H), 1.97 (m, 1H), 1.27 (s, 9H).

Example 26

N-[4-[(3S,4S,5R)-5-(3-tert-Butyl-benzylamino)-4-hydroxy-1,1-dioxo-hexahydro-1lambda*6*-thiopyran-3-ylmethyl]-2-fluoro-6-(2,2,2-trifluoro-ethoxy)-phenyl]-2-dimethylamino-acetamide dihydrochloride a) {(3R,4S,5S)-5-[4-Nitro-3-fluoro-5-(2,2,2-trifluoro-ethoxy)-benzyl]-4-hydroxy-tetrahydro-thiopyran-3-yl}-carbamic acid tert-butyl ester To a solution of [(3R,4S,5S)-5-(3,5-difluoro-4-nitro-benzyl)-4-hydroxy-tetrahydro-thiopyran-3-yl]-carbamic acid tert-butyl ester (5.0 g, 12.1 mmol, example 24f) and 2,2,2-trifluoroethanol (24.49 g, 242 mmol) was added pulverized KOH (0.694 g, 12.1 mmol) and the reaction mixture was heated at 70° C. for 3 h. The reaction mixture was evaporated and after addition of ice-water the product was extracted with EtOAc. Combined organic extracts were washed with brine, dried over $MgSO_4$, filtered and concentrated to provide the title compound after crystallization from $Et_2O$-hexane as light yellow crystals: TLC (toluene-EtOAc 3:1) Rf=0.17; HPLC $Rt_A$=2.28 min; ESIMS [M+H-isobutylene]$^+$=429; $^1$H NMR (600 MHz, DMSO-$d_6$): δ 7.13 (s, 1H), 7.10 (d, 1H), 6.76 (d, 1H), 5.10 (s, 1H), 5.01 (m, 2H), 3.37 (m, 1H), 3.19 (dd, 1H), 2.92 (dd, 1H), 2.55 (d, 1H), 2.48 (dd, 1H), 2.37 (dd, 1H), 2.31 (d, 1H), 2.25 (dd, 1H), 1.95 (m, 1H), 1.38 (s, 9H).

b) {(3R,4S,5S)-5-[4-Nitro-3-fluoro-5-(2,2,2-trifluoro-ethoxy)-benzyl]-4-hydroxy-1,1-dioxo-hexahydro-1lambda*6*-thiopyran-3-yl}-carbamic acid tert-butyl ester To a solution of {(3R,4S,5S)-5-[4-Nitro-3-fluoro-5-(2,2,2-trifluoro-ethoxy)-benzyl]-4-hydroxy-tetrahydro-thiopyran-3-yl}-carbamic acid tert-butyl ester (1.5 g, 3.1 mmol) in THF (20 mL) and water (12 mL) at 0° C. was added oxone (5.71 g, 9.3 mmol) in portions. After 2 h excess oxone was destroyed with sodiummetabisulfite. The reaction mixture was diluted with EtOAc (200 mL) and washed with aqueous saturated bicarbonate solution and brine. The organic phase was dried with $Na_2SO_4$, filtered and evaporated to provide a beige powder: TLC (cyclohexane-EtOAc 1:1) Rf=0.12; ESIMS $[M+NH_4]^+$=534; $^1$H NMR (600 MHz, DMSO-$d_6$): δ 7.10 (m, 2H), 6.89 (d, 1H), 5.25 (d, 1H), 5.01-4.94 (m, 2H), 3.70 (m, 1H), 3.20-3.00 (m, 5H), 2.93 (m, 1H), 2.68 (m, 1H), 2.17 (m, 1H), 1.38 (s, 9H).

c) (3R,4S,5S)-3-Amino-5-[4-nitro-3-fluoro-5-(2,2,2-trifluoro-ethoxy)-benzyl]-1,1-dioxo-hexahydro-1lambda*6*-thiopyran-4-ol hydrochloride salt The title compound was prepared in analogous manner as described for example 1g) from {(3R,4S,5S)-5-[4-Nitro-3-fluoro-5-(2,2,2-trifluoro-ethoxy)-benzyl]-4-hydroxy-1,1-dioxo-hexa-hydro-1lambda*6*-thiopyran-3-yl}-carbamic acid tert-butyl ester (1.6 g, 3.1 mmol) to yield the title compound as a white solid: $^1$H NMR (600 MHz, DMSO-d$_6$): δ 8.2 (s, 3H), 7.18 (s, 1H), 7.13 (d, 1H), 6.16 (d, 1H), 5.01 (q, 2H), 3.45-3.27 (m, 4H), 3.21 (t, 1H), 3.10 (dd, 1H), 3.03 (m, 1H), 2.68 (m, 1H), 2.23 (m, 1H).

d) (3R,4S,5S)-3-(3-tert-Butyl-benzylamino)-5-[3-fluoro-4-nitro-5-(2,2,2-trifluoro-ethoxy)-benzyl]-1,1-dioxo-hexahydro-1 lambda*6*-thiopyran-4-ol The title compound was prepared in analogous manner as described for example 1h) from (3R,4S,5S)-3-Amino-5-[4-nitro-3-fluoro-5-(2,2,2-trifluoro-ethoxy)-benzyl]-1,1-dioxo-hexahydro-1lambda*6*-thiopyran-4-ol hydrochloride salt (1.26 g, 2.78 mmol) and 3-tert-butyl benz-aldehyde (0.361 g, 2.26 mmol); ESIMS [M+H]$^+$=563, UPLC Rt$_D$=1.576 min, $^1$H NMR (600 MHz, DMSO-d$_6$): δ 7.35 (s, 1H), 7.27-7.21 (m, 2H), 7.15 (m, 2H), 7.10 (d, 1H), 5.32 (d, 1H), 5.01 (q, 2H), 3.81 (m, 1H), 3.63 (m, 1H), 3.38 (m, 1H), 3.20 (m, 1H), 3.10 (m, 1H), 3.05-2.98 (m, 2H), 2.80 (m, 2H), 2.63 (m, 1H), 2.41 (s, 1H), 2.14 (m, 1H), 1.25 (s, 9H).

e) (3aR,7S,7aS)-3-(3-tert-Butyl-benzyl)-7-[3-fluoro-4-nitro-5-(2,2,2-trifluoro-ethoxy)-benzyl]-5,5-dioxo-hexahydro-1-oxa-5lambda*6*-thia-3-aza-inden-2-one To a solution of (3R,4S,5S)-3-(3-tert-Butyl-benzylamino)-5-[3-fluoro-4-nitro-5-(2,2,2-trifluoro-ethoxy)-benzyl]-1,1-dioxo-hexahydro-1lambda*6*-thiopyran-4-ol (1.39 g, 2.47 mmol) in ACN (4 mL) and DMF (2 mL) was added carbonyl-diimidazole (0.8 g 4.94 mmol), DIPEA (4.8 g, 3.71 mmol) and DMAP (30 mg, 0.247 mmol). The reaction mixture was refluxed for 2 days and then concentrated in vacuo. The title compound was obtained after flash-chromatography on silica gel (toluene-EtOAc 1:1): ESIMS [M+NH$_4$]$^+$=606; UPLC Rt$_D$=1.913 min; $^1$H NMR (600 MHz, DMSO-d$_6$): δ 7.42 (s, 1H), 7.32 (d, 1H), 7.28 (t, 1H), 7.21 (s, 1H), 7.16 (d, 1H), 7.13 (d, 1H), 4.98 (q, 2H), 4.45 (d, 1H), 4.21 (m, 2H), 3.78 (m, 1H), 3.63 (m, 1H), 3.46 (t, 1H), 3.13 (m, 2H), 3.02 (m, 1H), 2.60 (m, 2H), 1.25 (s, 9H).

f) (3aR,7S,7aS)-7-[4-Amino-3-fluoro-5-(2,2,2-trifluoro-ethoxy)-benzyl]-3-(3-tert-butyl-benzyl)-5,5-dioxo-hexahydro-1-oxa-5lambda*6*-thia-3-aza-inden-2-one The title compound was prepared in analogous manner as described for example 1j) from (3aR,7S,7aS)-3-(3-tert-butyl-benzyl)-7-[3-fluoro-4-nitro-5-(2,2,2-trifluoro-ethoxy)-benzyl]-5,5-dioxo-hexahydro-1-oxa-5lambda*6*-thia-3-aza-inden-2-one (1.32 g, 2.24 mmol) to yield a white foam: TLC Rf=0.60 (toluene-ETA 85:15); ESIMS [M+NH$_4$]$^+$=576; LCMS Rt$_{H1}$=3.60 min API ESI pos. [M+H]$^+$=559; $^1$H NMR (600 MHz, DMSO-d$_6$): δ 7.39 (s, 1H), 7.32 (d, 1H), 7.28 (t, 1H), 7.10 (d, 1H), 6.66 (s, 1H), 6.65 (d, 1H), 4.70 (q, 2H), 4.60 (s, 2H), 4.41 (d, 1H), 4.20 (d, 1H), 4.14 (t, 1H), 3.73 (m, 1H), 3.63 (m, 1H), 3.45 (t, 1H), 3.05 (m, 1H), 2.97 (m, 1H), 2.80 (m, 1H), 2.41 (m, 2H), 1.25 (s, 9H).

g) N-[4-[(3aR,7S,7aS)-3-(3-tert-Butyl-benzyl)-2,5,5-trioxo-octahydro-1-oxa-5lambda*6*-thia-3-aza-inden-7-ylmethyl]-2-fluoro-6-(2,2,2-trifluoro-ethoxy)-phenyl]-2-chloro-acetamide The title compound was prepared in analogous manner as described for example 8p) from (3aR,7S,7aS)-7-[4-amino-3-fluoro-5-(2,2,2-trifluoro-ethoxy)-benzyl]-3-(3-tert-butyl-benzyl)-5,5-dioxohexahydro-1-oxa-5lambda*6*-thia-3-aza-inden-2-one (400 mg, 0.716 mmol) and chloroacetylchloride (324 mg, 2.86 mmol) to yield a white foam: TLC Rf=0.40 (toluene-ETA 85:15); ESIMS [M+NH$_4$]$^+$=652, 654, [M−H]$^-$=633, 635; UPLC Rt$_D$=1.861 min; $^1$H NMR (600 MHz, DMSO-d$_6$): δ 9.64 (s, 1H, NH), 7.41 (s, 1H), 7.33 (d, 1H), 7.28 (t, 1H), 7.13 (d, 1H), 6.91 (s, 1H), 6.88 (d, 1H), 4.74 (q, 2H), 4.43 (d, 1H), 4.25-4.18 (m, 4H), 3.78 (d, 1H), 3.65 (t, 1H), 3.50 (t, 1H), 3.17 (t, 1H), 2.99 (m, 2H), 2.56 (m, 2H), 1.25 (s, 9H).

h) N-[4-[(3aR,7S,7aS)-3-(3-tert-Butyl-benzyl)-2,5,5-trioxo-octahydro-1-oxa-5lambda*6*-thia-3-aza-inden-7-ylmethyl]-2-fluoro-6-(2,2,2-trifluoro-ethoxy)-phenyl]-2-dimethyl-amino-acetamide The title compound was prepared in analogous manner as described for example 8q) from N-[4-[(3aR,7S,7aS)-3-(3-tert-butyl-benzyl)-2,5,5-trioxo-octahydro-1-oxa-5lambda*6*-thia-3-aza-inden-7-ylmethyl]-2-fluoro-6-(2,2,2-trifluoro-ethoxy)-phenyl]-2-chloro-acetamide (100 mg, 0.157 mmol) and dimethylamine (64.5 mg, 0.472 mmol) to yield a brown foam: TLC Rf=0.32 (toluene-EtOAc-MeOH 5:5:1); ESIMS [M+H]$^+$=644; UPLC Rt$_D$=1.515 min; $^1$H NMR (600 MHz, DMSO-d$_6$): δ 9.02 (s, 1H, NH), 7.41 (s, 1H), 7.33 (d, 1H), 7.28 (t, 1H), 7.13 (d, 1H), 6.88 (s, 1H), 6.84 (d, 1H), 4.74 (q, 2H), 4.43 (d, 1H), 4.23 (m, 2H), 3.77 (m, 1H), 3.66 (t, 1H), 3.50 (t, 2H), 3.18 (m, 1H), 3.02 (s, 2H), 2.97 (m, 2H), 2.53 (m, 1H), 2.26 (s, 6H), 1.25 (s, 9H).

i) N-[4-[(3S,4S,5R)-5-(3-tert-Butyl-benzylamino)-4-hydroxy-1,1-dioxo-hexahydro-1lambda*6*-thiopyran-3-ylmethyl]-2-fluoro-6-(2,2,2-trifluoro-ethoxy)-phenyl]-2-di-methylamino-acetamide dihydrochloride The title compound was prepared in analogous manner as described for example 1o from N-[4-[(3aR,7S,7aS)-3-(3-tert-butyl-benzyl)-2,5,5-trioxo-octahydro-1-oxa-5lambda*6*-thia-3-aza-inden-7-ylmethyl]-2-fluoro-6-(2,2,2-trifluoro-ethoxy)-phenyl]-2-dimethylamino-acetamide (58 mg, 0.09 mmol) to yield the dihydrochloride as a beige solid: TLC Rf=0.20 (toluene-ETA 85:15); ESIMS [M+H]$^+$=618; UPLC Rt$_E$=0.964 min; $^1$H NMR (600 MHz, DMSO-d$_6$+TFA): δ 10.11 (s, 1H), 9.92 (s br, 1H), 9.80 (s br, 1H), 9.02 (s br, 1H), 7.63 (s, 1H), 7.44 (d, 1H), (m, 2H), 6.91 (s, 1H), 6.88 (d, 1H), 4.74 (q, 2H), 4.25 (m, 2H), 4.18 (s, 2H), 3.85 (m, 1H), 3.69 (t, 1H), 3.61 (t, 1H), 3.28-3.15 (m, 3H), 2.89 (m, 1H), 2.82 (s, 6H), 2.49 (m, 1H), 2.13 m, 1H), 1.25 (s, 9H).

Examples 27 to 29

The compounds listed in Table 3 were prepared by a procedure analogous to that used in example 26.

TABLE 3

| Example | R | Chromatography Method | Chromatography Rt [min] | ESIMS [M + H]+ |
|---|---|---|---|---|
| 27 | (ethylamino-acetamido group) | E | 0.964 | 618 |
| 28 | (azetidin-1-yl-acetamido group) | E | 0.975 | 630 |
| 29 | (piperidin-1-yl-acetamido group) | E | 0.985 | 658 |

Example 30

(3S,4S,5R)-3-[4-Amino-3-fluoro-5-(2,2,2-trifluoro-1-rifluoromethyl-ethoxy)-benzyl]-5-[(3,3-dimethyl-1,3-dihydro-isobenzofuran-5-ylmethyl)-amino]-1,1-dioxo-hexa-hydro-1lambda*6*-thiopyran-4-ol dihydrochloride a) {(3R,4S,5S)-5-[3-Fluoro-4-nitro-5-(2,2,2-trifluoro-1-trifluoromethyl-ethoxy)-benzyl]-4-hydroxy-tetrahydro-thiopyran-3-yl}-carbamic acid tert-butyl ester The title compound was prepared in analogous manner as described for example 26 from [(3R,4S,5S)-5-(3,5-difluoro-4-nitro-benzyl)-4-hydroxy-tetrahydro-thiopyran-3-yl]-carbamic acid tert-butyl ester ester (example 24f) and 1,1,1,3,3,3-hexafluoro-propan-2-ol to yield an amorphous solid: TLC (hexane-EtOAc 1:1) Rf=0.42; HPLC Rt$_A$=2.43 min; ESIMS [M+H-isobutylene]+=497; $^1$H NMR (400 MHz, CDCl$_3$): δ 6.94 (d, 1H), 6.82 (s, 1H), 4.97 (m, 1H), 4.59 (m, 1H), 3.74 (m, 1H), 3.40 (m, 1H), 3.29 (dd, 1H), 3.03 (dd, 1H), 2.74 (m, 1H), 2.61 (dd, 1H), 2.52 (dd, 1H), 2.35 (m, 1H), 2.12 (m, 1H), 1.42 (s, 9H).

b) {(3R,4S,5S)-5-[3-Fluoro-4-nitro-5-(2,2,2-trifluoro-1-trifluoromethyl-ethoxy)-benzyl]-4-hydroxy-1,1-dioxo-hexahydro-1lambda*6*-thiopyran-3-yl}-carbamic acid tert-butyl ester To a solution of {(3R,4S,5S)-5-[3-fluoro-4-nitro-5-(2,2,2-trifluoro-1-trifluoromethyl-ethoxy)-benzyl]-4-hydroxy-tetrahydro-thiopyran-3-yl}-carbamic acid tert-butyl ester (3.31 g, 6.0 mmol) in THF-H$_2$O 1:1 (150 mL) was added oxone (7.6 g, 12.0 mmol). After stirring the reaction mixture for 2 h at 25° C., 2.5 g NaOAc and 3 g sodium metabisulfite were added. The reaction mixture was stirred for 0.5 h, basified with saturated aq. K$_2$CO$_3$-solution and the product was extracted with EtOAc. Combined organic extracts were washed with brine, dried over MgSO$_4$, filtered and concentrated to provide the title compound after chromatographic purification (Combi-Flash, 40 g silicagel, hexane-EtOAc 95:5 to EtOAc) as a colorless amorphous solid: TLC (toluene-THF 1:1) Rf=0.45; HPLC Rt$_A$=2.21 min; ESIMS [M+NH$_4$]+=602; $^1$H NMR (400 MHz, CDCl$_3$): δ 6.92 (d, 1H), 6.85 (s, 1H), 5.05 (m, 1H), 4.92 (d, 1H), 4.02 (m, 1H), 3.45 (m, 1H), 3.34 (m, 2H), 3.22 (dd, 1H), 3.18 (m, 1H), 2.94 (m, 1H), 2.82 (dd, 1H), 2.74 (dd, 1H), 2.52 (m, 1H), 1.43 (s, 9H).

c) (3R,4S,5S)-3-Amino-5-[3-fluoro-4-nitro-5-(2,2,2-trifluoro-1-trifluoromethyl-ethoxy)-benzyl]-1,1-dioxo-hexahydro-1lambda*6*-thiopyran-4-ol hydrochloride To a solution of {(3R,4S,5S)-5-[3-fluoro-4-nitro-5-(2,2,2-trifluoro-1-trifluoromethyl-ethoxy)-benzyl]-4-hydroxy-1,1-dioxo-hexahydro-1lambda*6*-thiopyran-3-yl}-carbamic acid tert-butyl ester (3.42 g, 5.85 mmol) in THF (5 mL) was added 4N HCl in dioxane (20 mL) and the reaction mixture was stirred for 2 h at 25° C. After evaporation the residue was stirred with Et$_2$O, filtered and dried to provide the title compound as a beige solid: TLC (EtOAc-MeOH 9:1) Rf=0.12; HPLC Rt$_A$=1.76 min; ESIMS [M+H]$^+$=485; $^1$H NMR (400 MHz, CD$_3$OD): δ 7.24 (s, 1H), 7.18 (d, 1H), 6.29 (m, 1H), 3.3-3.7 (m, 5H), 3.21 (dd, 1H), 2.97 (m, 1H), 2.70 (dd, 1H), 2.42 (m, 1H).

d) (3R,4S,5S)-3-[(3,3-Dimethyl-1,3-dihydro-isobenzofuran-5-ylmethyl)-amino]-5-[3-fluoro-4-nitro-5-(2,2,2-trifluoro-1-trifluoromethyl-ethoxy)-benzyl]-1,1-dioxo-hexahydro-1lambda*6*-thiopyran-4-ol The title compound was prepared in analogous manner as described for example 1h from (3R,4S,5S)-3-amino-5-[3-fluoro-4-nitro-5-(2,2,2-trifluoro-1-trifluoromethyl-ethoxy)-benzyl]-1,1-dioxo-hexahydro-1lambda*6*-thiopyran-4-ol hydrochloride to yield the title compound as a light yellow solid: TLC (EtOAc-MeOH 19:1) Rf=0.45; HPLC Rt$_A$=2.00 min; ESIMS [M+H]$^+$=645.

e) (3S,4S,5R)-3-[4-Amino-3-fluoro-5-(2,2,2-trifluoro-1-trifluoromethyl-ethoxy)-benzyl]-5-[(3,3-dimethyl-1,3-dihydro-isobenzofuran-5-ylmethyl)-amino]-1,1-dioxo-hexahydro-1lambda*6*-thiopyran-4-ol dihydrochloride The title compound was prepared in analogous manner as described for example 24k from (3R,4S,5S)-3-[(3,3-dimethyl-1,3-dihydro-isobenzofuran-5-ylmethyl)-amino]-5-[3-fluoro-4-nitro-5-(2,2,2-trifluoro-1-trifluoromethyl-ethoxy)-benzyl]-1,1-dioxo-hexahydro-1lambda*6*-thiopyran-4-ol and 3,3-dimethyl-1,3-dihydro-isobenzofuran-5-carbaldehyde (example 30f to yield the title compound after preparative HPLC (Sunfire C18 OBD 5 µm, 100×30, 5-100% ACN in water+0.1% TFA gradient, 25 min) as a colorless amorphous solid: HPLC Rt$_A$=1.79 min; ESIMS [M+H]$^+$=615; $^1$H NMR (600 MHz, DMSO-d$_6$): δ 9.89 (s, 1H), 9.08 (s, 1H), 7.48 (s, 1H), 7.47 (d, 1H), 7.34 (d, 1H), 6.85 (s, 1H), 6.76 (d, 1H), 6.46 (m, 1H), 6.25 (s, 1H), 4.96 (s, 2H), 4.30 (m, 1H), 4.24 (m, 1H), 3.6-3.9 (m, 3H), 3.18 (m, 2H), 3.04 (dd, 1H), 2.81 (m, 1H), 2.40 (dd, 1H), 2.03 (m, 1H), 1.41 (d, 6H).

f) 3,3-Dimethyl-1,3-dihydro-isobenzofuran-5-carbaldehyde

To a solution of 6-bromo-1,1-dimethyl-1,3-dihydro-isobenzofuran (1.41 g, 6.3 mmol) in anhydrous THF (10 mL) was added under Argon at −78° C. 2.5 M nBuLi in hexane (2.7 mL, 6.6 mmol) and after stirring for 0.5 h at −78° C. DMF (0.98 mL, 12.5 mmol) was added. After stirring for 2 h at −78° C. the reaction mixture was added to 0.5 N cold aq. HCl and extracted with Et$_2$O. Combined organic layers were washed with brine, dried over MgSO$_4$, filtered and evaporated. The title compound was obtained after chromatographic purification (Combi-Flash, 40 g silicagel, hexane-EtOAc 95:5 to 50:50) as a light yellow oil: TLC (hexane-EtOAc 1:1) Rf=0.50; HPLC Rt$_A$=1.43 min; $^1$H NMR (400 MHz, CDCl$_3$): δ 10.02 (s, 1H), 7.78 (d, 1H), 7.65 (s, 1H), 7.36 (d, 1H), 5.11 (s, 2H), 1.53 (s, 6H).

Example 31

(3S,4S,5R)-3-[4-Amino-3-fluoro-5-(2,2,2-trifluoro-1-trifluoromethyl-ethoxy)-benzyl]-1,1-dioxo-5-(3-trimethylsilanyl-benzylamino)-hexahydro-1lambda*6*-thiopyran-4-ol The title compound was prepared in analogous manner as described for example 30 from (3R,4S,5S)-3-amino-5-[3-fluoro-4-nitro-5-(2,2,2-trifluoro-1-trifluoromethyl-ethoxy)-benzyl]-1,1-dioxo-hexahydro-1lambda*6*-thiopyran-4-ol hydrochloride (example 30c) and 3-trimethyl-silanyl-benzaldehyde to yield the title compound after purification by preparative HPLC (Sunfire C18, 5 µm, 30×100 mm, 40-60% ACN in water+0.1% TFA gradient, 50 ml/min, 16 min) as a colorless amorphous solid: TLC (CH$_2$Cl$_2$-MeOH-NH$_3$ 95:4.5:0.5) Rf=0.58; HPLC Rt$_{G1}$=1.15 min; ESIMS [M+H]$^+$=617; $^1$H-NMR (400 MHz, DMSO-d$_6$): δ 7.46 (s, 1H), 7.38-7.28 (m, 3H), 6.81 (s, 1H), 6.72 (d, 1H), 6.40 (m, 1H), 5.18 (d, 1H), 4.64 (s, 2H), 3.83 (d, 1H), 3.66 (d, 1H), 3.39 (m, 1H), 3.19 (m, 1H), 3.07-2.94 (m, 3H), 2.81 (m, 1H), 2.66 (m, 1H), 2.35 (dd, 1H), 2.02 (m, 1H), 0.25 (s, 9H).

Example 32

(3S,4S,5R)-3-[4-Amino-3-fluoro-5-((R)-2,2,2-trifluoro-1-methoxymethyl-ethoxy)-benzyl]-5-(3-tert-butyl-benzylamino)-1,1-dioxo-hexahydro-1lambda*6*-thio-pyran-4-ol a) (3R,4S,5S)-3-(3-tert-Butyl-benzylamino)-5-[3-fluoro-4-nitro-5-((R)-2,2,2-trifluoro-1-methoxymethyl-ethoxy)-benzyl]-1,1-dioxo-hexahydro-1lambda*6*-thiopyran-4-ol The title compound was prepared in analogous manner as described for example 24j) from (3R,4S,5S)-3-(3-tert-butyl-benzylamino)-5-(3,5-difluoro-4-nitro-benzyl)-1,1-dioxo-hexahydro-1lambda*6*-thiopyran-4-ol (example 24i) and (R)-1,1,1-trifluoro-3-methoxy-propan-2-ol to yield the title compound as a colorless foam: TLC (EtOAc-MeOH 19:1) Rf=0.47; HPLC Rt$_A$=2.13 min; ESIMS [M+H]$^+$=607; $^1$H NMR (600 MHz, DMSO-d$_6$): δ 7.34 (s, 1H), 7.28 (s, 1H), 7.24 (m, 2H), 7.143 (d, 1H), 7.10 (d, 1H), 5.59 (m, 1H), 5.30 (d, 1H), 3.80 (m, 2H), 3.70 (dd, 1H), 3.64 (d, 1H), 3.40 (dt, 1H), 3.29 (s, 3H), 3.21 (m, 1H), 3.12 (dd, 1H), 3.03 (m, 2H), 2.81 (m, 1H), 2.62 (dd, 1H), 2.42 (m, 1H), 2.14 (m, 1H), 1.27 (s, 9H).

b) (3S,4S,5R)-3-[4-Amino-3-fluoro-5-((R)-2,2,2-trifluoro-1-methoxymethyl-ethoxy)-benzyl]-5-(3-tert-butyl-benzylamino)-1,1-dioxo-hexahydro-1lambda*6*-thiopyran-4-ol The title compound was prepared in analogous manner as described for example 24k) from (3R,4S,5S)-3-(3-tert-Butyl-benzylamino)-5-[3-fluoro-4-nitro-5-((R)-2,2,2-trifluoro-1-methoxy-methyl-ethoxy)-benzyl]-1,1-dioxo-hexahydro-1lambda*6*-thiopyran-4-ol (example 32a) to yield the title compound after purification by preparative HPLC: HPLC Rt$_{B1}$=13.76 min; ESIMS [M+H]$^+$=577; $^1$H NMR (500 MHz, DMSO-d$_6$): δ 7.35 (s, 1H), 7.28 (m, 2H), 7.14 (d, 1H), 6.72 (s, 1H), 6.63 (d, 1H), (d, 1H), 5.17 (d, 1H), 5.12 (m, 1H), 4.62 (s, 2H, NH2), 3.80 (dd, 1H), 3.74 (m, 2H), 3.64 (dd, 1H), 3.38 (dt, 1H), 3.32 (s, 3H), 3.15 (m, 1H), 3.05-2.93 (m, 3H), 2.79 (m, 1H), 2.66 (m, 1H), 2.42 (m, 1H), 2.34 (dd, 1H), 2.02-1.94 (m 1H), 1.27 (s, 9H).

c) (R)-1,1,1-Trifluoro-3-methoxy-propan-2-ol

A solution of R-(+)-3,3,3-Trifluoro-1,1-epoxypropane (71 g, 0.634 mol) and concentrated sulfuric acid (2.32 mL) in MeOH (320 mL) was heated at 85° C. in a closed 500 mL glass reactor for 16 h. The cold reaction mixture was diluted with diethyl ether and neutralized with concentrated aqueous potassium carbonate solution. The organic phase was repeatedly washed with cold brine, dried over $MgSO_4$, filtered and evaporated (40° C., 100 mbar). The resulting liquid was distilled using a 10 cm vigreux column with dry ice cooling of the receiver flask: bp 44-47° C. (33 mbar); $[\alpha]^{Na}=9.8°$ (c=1, MeOH); ESIMS $[M+NH_4]^+=162$; $^1H$ NMR (400 MHz, $CDCl_3$): δ 4.15-4.05 (m, 1H), 3.68-3.58 (m, 2H), 3.44 (s, 3H), 2.89 (d, 1H).

Examples 33 to 37

The compounds listed in Table 4 were prepared by a procedure analogous to that used in example 32.

TABLE 4

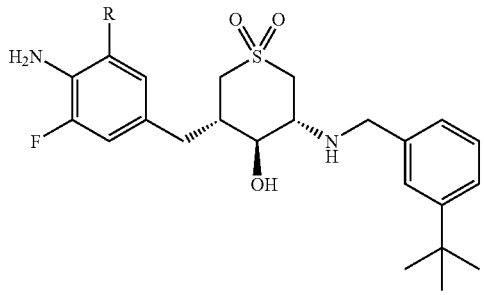

| Example | R | Chromatography Method | Chromatography Rt [min] | ESIMS [M + H]+ |
|---|---|---|---|---|
| 33 | | B | 12.55 | 591 |
| 34 | | B | 9.50 | 591 |
| 35 | | B | 12.87 | 605 |
| 36 | | A | 1.93 | 621 |

TABLE 4-continued

| Example | R | Chromatography Method | Chromatography Rt [min] | ESIMS [M + H]+ |
|---|---|---|---|---|
| 37 | (azetidinyl-CH2-CH(OtBu)-CF3 group) | B | 10.02 | 602 |

(R)-3-Ethoxy-1,1,1-trifluoro-propan-2-ol, (S)-3-ethoxy-1,1,1-trifluoro-propan-2-ol, (R)-1,1,1-trifluoro-3-isopropoxy-propan-2-ol and (R)-1,1,1-trifluoro-3-(2-methoxy-ethoxy)-propan-2-ol were prepared in analogous manner as described for example 32c) from the corresponding alcohols and (R)- or (S)-epoxides.

(R)-3-Azetidin-1-yl-1,1,1-trifluoro-propan-2-ol was prepared following a procedure described in *J. Org. Chem.* 1995, 60, 41, starting from (R)-2-trifluoromethyl-oxirane.

Example 38

(3S,4S,5R)-3-[4-Amino-3-fluoro-5-((R)-2,2,2-trifluoro-1-hydroxymethyl-ethoxy)-benzyl]-5-(3-tert-butyl-benzylamino)-1,1-dioxo-hexahydro-1lambda*6*-thio-pyran-4-ol a) (R)-1,1,1-Trifluoro-3-(4-methoxybenzyloxy)-propan-2-ol To a suspension of NaH (390 mg, 8.9 mmol, 55% in mineral oil) in THF (10 mL) at 0° C. was added 4-methoxybenzylalcohol (1.27 g, 8.92 mmol) in THF (5 mL). After 1 h stirring at 0° C. R-(+)-3,3,3-trifluoro-1,2-epoxypropane (500 mg, 4.46 mmol) was added to a 20 mL microwave vial via syringe. The closed vial was heated at 100° C. for 18 h. The reaction mixture was diluted with water and extracted twice with Et$_2$O. The organic phase was washed with brine, dried over MgSO$_4$, filtered and evaporated. Chromatography over silica (cyclohexane-EtOAc 95:5 to cyclohexane-EtOAc 75:25) afforded the title compound: ESIMS [M+NH$_4$]$^+$=268; $^1$H NMR (360 MHz, CDCl$_3$): δ 7.29 (d, 2H), 6.94 (d, 2H), 4.56 (s, 2H), 4.15 (m, 1H), 3.87 (s, 3H), 3.74 (dd, 1H), 3.66 (dd, 1H), 2.88 (d, 1H).

b) (3R,4S,5S)-3-(3-tert-Butyl-benzylamino)-5-{3-fluoro-4-nitro-5-[(R)-2,2,2-trifluoro-1-(4-methoxy-benzyloxymethyl)-ethoxy]-benzyl}-1,1-dioxo-hexahydro-1lambda*6*-thio-pyran-4-ol To solution of (3R,4S,5S)-3-(3-tert-butyl-benzylamino)-5-(3,5-difluoro-4-nitro-benzyl)-1,1-dioxo-hexahydro-1lambda*6*-thiopyran-4-ol (80 mg, 0.166 mmol, example 24i) and (R)-1,1,1-trifluoro-3-(4-methoxybenzyloxy)-propan-2-ol (415 mg, 1.66 mmol, example 38a) in THF (3 mL) was added NaHMDS 1M in THF (0.35 mL, 0.35 mmol) at room temperature. After 1.5 h at room temperature the solution was poured onto an aqueous solution of KH$_2$PO$_4$ and was extracted with EtOAc. The organic phase was washed with water and brine, dried over Na$_2$SO$_4$ and evaporated. Chromatography over silica (5 g, cyclohexane-EtOAc 80:20 to 100% EtOAc) afforded the title compound: LCMS Rt$_t$=2.44 min; ESIMS [M+H]$^+$=713.

c) (3S,4S,5R)-3-{4-Amino-3-fluoro-5-[(R)-2,2,2-trifluoro-1-(4-methoxy-benzyloxymethyl)-ethoxy]-benzyl}-5-(3-tert-butyl-benzylamino)-1,1-dioxo-hexahydro-1lambda*6*-thiopyran-4-ol The title compound was prepared in analogous manner as described for example 24k) from (3R,4S,5S)-3-(3-tert-butyl-benzylamino)-5-{3-fluoro-4-nitro-5-[(R)-2,2,2-trifluoro-1-(4-methoxy-benzyloxymethyl)-ethoxy]-benzyl}-1,1-dioxo-hexahydro-1lambda*6*-thiopyran-4-ol (104 mg, 0.146 mmol, example 38b): LCMS Rt$_t$=2.26 min; ESIMS [M+H]$^+$=683.

d) (3S,4S,5R)-3-[4-Amino-3-fluoro-5-[(R)-2,2,2-trifluoro-1-hydroxymethyl-ethoxy-benzyl]-5-(3-tert-butyl-benzylamino)-1,1-dioxo-hexahydro-1lambda*6*-thiopyran-4-ol To a solution of (3S,4S,5R)-3-{4-amino-3-fluoro-5-[(R)-2,2,2-trifluoro-1-(4-methoxy-benzyl-oxymethyl)-ethoxy]-benzyl}-5-(3-tert-butyl-benzylamino)-1,1-dioxo-hexahydro-1lambda*6*-thiopyran-4-ol (69 mg, 0.1 mmol) in CH$_2$Cl$_2$ (4.5 mL) was added TFA (0.5 mL) at room temperature. The reaction mixture was poured onto aq. NaHCO$_3$ solution and extracted with CH$_2$Cl$_2$. The organic phase was washed with water and brine, dried over Na$_2$SO$_4$, filtered and evaporated. Preparative HPLC purification afforded the title compound: LCMS Rt$_t$=1.70 min; ESIMS [M+H]$^+$=563.

Example 39

(3S,4S,5R)-3-[4-Amino-3-((R)-1-aminomethyl-2,2,2-trifluoro-ethoxy)-5-fluoro-benzyl]-5-(3-tert-butyl-benzylamino)-1,1-dioxo-hexahydro-1lambda*6*-thiopyran-4-ol a) (3S,4S,5R)-3-[3-((R)-1-Azidomethyl-2,2,2-trifluoro-ethoxy)-5-fluoro-4-nitro-benzyl]-5-(3-tert-butyl-benzylamino)-1,1-dioxo-hexahydro-1lambda*6*-thiopyran-4-ol The title compound was prepared in analogous manner as described for example 38b from (3R,4S,5S)-3-(3-tert-butyl-benzylamino)-5-{3-fluoro-4-nitro-5-[(R)-2,2,2-trifluoro-1-(4-methoxy-benzyloxymethyl)-ethoxy]-benzyl}-1,1-dioxo-hexahydro-1lambda*6*-thiopyran-4-ol (example 38b) and (R)-3-azetidin-1-yl-1,1,1-trifluoro-propan-2-ol: LCMS $Rt_1$=2.73 min; ESIMS [M+H]$^+$=618.

b) (3S,4S,5R)-3-[4-Amino-3-((R)-1-aminomethyl-2,2,2-trifluoro-ethoxy)-5-fluoro-benzyl]-5-(3-tert-butyl-benzylamino)-1,1-dioxo-hexahydro-1lambda*6*-thiopyran-4-ol The title compound was prepared in analogous manner as described for example 24k from (3S,4S,5R)-3-[3-((R)-1-azidomethyl-2,2,2-trifluoro-ethoxy)-5-fluoro-4-nitro-benzyl]-5-(3-tert-butyl-benzylamino)-1,1-dioxo-hexahydro-1lambda*6*-thiopyran-4-ol: HPLC $Rt_F$=2.38 min; ESIMS [M+H]$^+$=562; $^1$H NMR (400 MHz, DMSO-d6): δ 7.36 (s, 1H), 7.24 (m, 2H), 7.15 (m, 1H), 6.67 (s, 1H), 6.64 (d, 1H), 5.17 (d, 1H), 5.07 (s, 2H), 4.66 (m, 1H), 3.82 (d, 1H), 3.64 (d, 1H), 3.37 (dt, 1H), 3.17 (m, 1H), 3.05-2.88 (m, 5H), 2.8 (m, 1H), 2.65 (dt, 1H), 2.40 (s, 1H), 2.32 (dd, 1H), 1.96 (m, 3H), 1.28 (s, 9H).

Example 40

(3S,4S,5R)-3-[4-Amino-3-fluoro-5-((R)-2,2,2-trifluoro-1-methoxymethyl-ethoxy)-benzyl]-5-(3-tert-butyl-benzylamino)-tetrahydro-thiopyran-4-ol hydrochloride a) {(3R,4S,5S)-5-[3-Fluoro-4-nitro-5-((R)-2,2,2-trifluoro-1-methoxymethyl-ethoxy)-benzyl]-4-hydroxy-tetrahydro-thiopyran-3-yl}-carbamic acid tert-butyl ester To a solution of [(3R,4S,5S)-5-(3,5-difluoro-4-nitro-benzyl)-4-hydroxy-tetrahydro-thiopyran-3-yl]-carbamic acid tert-butyl ester (1 g, 2.47 mmol) and (R)-1,1,1-trifluoro-3-methoxy-propan-2-ol (392 mg, 2.72 mmol) in THF (13 mL) was added tert-BuOK (277 mg, 2.47 mmol) in small portions at 0° C. over a period of 30 min. After 1 h the cooling bath was removed and the orange solution was stirred at room temperature for 5 h. The reaction mixture was diluted with EtOAc (500 mL) and washed with ice cooled $K_2CO_3$ solution and cold brine. The organic phase was dried over $Na_2SO_4$, filtered and evaporated to yield a brown-yellowish foam: TLC Rf=0.50 (toluene-ETA 85:15); HPLC $Rt_E$=1.157 min; ESIMS [M+H-Boc]$^+$=429; $^1$H NMR (600 MHz, DMSO-d$_6$): δ 7.28 (s, 1H), 7.10 (d, 1H), 6.71 (d, 1H), 5.65 (broad, 1H), 4.95 (d, 1H), 3.83 (dd, 1H), 3.73 (dd, 1H), 3.42 (m, 1H), 3.31 (s, 3H), 3.25 (dd, 1H), 2.93 (m, 1H), 2.54 (d, 1H), 2.48-2.35 (m, 2H), 2.32-2.20 (m, 2H), 1.94 (m, 1H), 1.37 (s, 9H).

b) (3R,4S,5S)-3-Amino-5-[3-fluoro-4-nitro-5-((R)-2,2,2-trifluoro-1-methoxymethyl-ethoxy)-benzyl]-tetrahydro-thiopyran-4-ol hydrochloride The title compound was prepared in analogous manner as described for example 1g from {(3R,4S,5S)-5-[3-fluoro-4-nitro-5-((R)-2,2,2-trifluoro-1-methoxymethyl-ethoxy)-benzyl]-4-hydroxy-tetrahydro-thiopyran-3-yl}-carbamic acid tert-butyl ester (2.18 g, 4.12 mmol) to yield the title compound as light yellow solid: HPLC $Rt_F$=1.83 min; ESIMS [M+H]$^+$=429; $^1$H NMR (600 MHz, DMSO-d$_6$): δ 8.09 (s broad, NH$_3$), 7.34 (s, 1H), 7.15 (d, 1H), 5.91 (d, 1H), 5.65 (broad, 1H), 3.78 (dd, 1H), 3.70 (dd, 1H), 3.31 (s, 3H), 3.25 (dd, 1H), 3.15-3.02 (m, 2H), 2.78 (d, 1H), 2.68 (t, 1H), 2.48-2.32 (m, 3H), 2.00 (m, 1H).

c) (3R,4S,5S)-3-(3-tert-Butyl-benzylamino)-5-[3-fluoro-4-nitro-5-((R)-2,2,2-trifluoro-1-methoxymethyl-ethoxy)-benzyl]-tetrahydro-thiopyran-4-ol To a solution of (3R,4S,5S)-3-amino-5-[3-fluoro-4-nitro-5-((R)-2,2,2-trifluoro-1-methoxy-methyl-ethoxy)-benzyl]-tetrahydro-thiopyran-4-ol hydrochloride (1.217 g, 2.52 mmol) in MeOH-CH$_2$Cl$_2$ 1:2 (28 mL) was added NaOAc (0.517 g, 6.3 mmol), powdered molecular sieves (4A) and 3-tert-butyl-benzaldehyde (CAS registry 23039-28-3) (0.413 g, 2.55 mmol). The reaction mixture was stirred at 25° C. for 16 h, acetic acid (0.5 mL) was added followed by NaBH$_3$CN (0.396 g, 6.3 mmol). The reaction mixture was stirred at room temperature for 3 h and was quenched by adding 2N aq. HCl solution. EtOAc was added and the solution was washed with 2N $K_2CO_3$ solution and with brine. The organic phase was dried over $Na_2SO_4$, filtered and evaporated. The title compound was obtained after purification by flash-chromatography on NH4OH deactivated silica gel (90 g, toluene-EtOAc 1:1) as a light yellow oil: TLC (toluene-ETA 85:15) Rf=0.52; HPLC $Rt_A$=2.178 min; ESIMS [M+H]$^+$=575; $^1$H NMR (600 MHz, CDCl$_3$): δ 7.33 (s, 1H), 7.28 (s, 1H), 7.26 (m, 2H), 7.18-7.08 (m, 2H), 5.7 (broad, 1H), 5.06 (d, 1H), 3.9-3.78 (m, 2H), 3.71-3.62 (m, 2H), 3.31 (s, 3H), 3.22 (d, 1H), 2.90 (m, 1H), 2.82 (d, 1H), 2.55 (m, 1H), 2.48 (s broad, 1H), 2.41 (m, 1H), 2.35-2.20 (m, 3H), 1.93 (m, 1H), 1.25 (s, 9H).

d) (3S,4S,5R)-3-[4-Amino-3-fluoro-5-((R)-2,2,2-trifluoro-1-methoxymethyl-ethoxy)-benzyl]-5-(3-tert-butyl-benzylamino)-tetrahydro-thiopyran-4-ol dihydrochloride The title compound was prepared in analogous manner as described for example 24k from (3R,4S,5S)-3-(3-tert-butyl-benzylamino)-5-[3-fluoro-4-nitro-5-((R)-2,2,2-trifluoro-1-methoxy-methyl-ethoxy)-benzyl]-tetrahydro-thiopyran-4-ol (100 mg, 0.174 mmol) to yield the title compound as a colorless solid: TLC (toluene-ETA 85:15) Rf=0.69; HPLC $Rt_A$=2.03 min; ESIMS [M+H]$^+$=545; $^1$H NMR (600 MHz, CDCl$_3$): HCl-salt: δ 9.65 (s, broad, 1H, NH), 8.88 (s, broad, 1H, NH), 7.67 (s, 1H), 7.43-7.32 (m, 3H), 6.80 (s, 1H), 6.69 (d, 1H), 5.68 (broad, 1H), 5.6-4.70 (very broad, 3H), 4.3-4.15 (m, 2H), 3.75 (d, 2H), 3.33 (m, 4H), 3.15-3.05 (m, 2H), 2.90 (m, 1H), 2.80 (t, 1H), 2.30-2.22 (m, 2H), 2.18 (m, 1H), 1.77 (m, 1H), 1.25 (s, 9H).

Example 41

(1R,3S,4S,5R)-3-[4-Amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-ol (cis-sulfoxide)

a) {(1R,3R,4S,5S)-5-[3-Fluoro-4-nitro-5-((R)-2,2,2-trifluoro-1-methoxymethyl-ethoxy)-benzyl]-4-hydroxy-1-oxotetrahydro-thiopyran-3-yl}-carbamic acid tert-butyl ester and {(1S,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester To a solution of {(3R,4S,5S)-5-[3-fluoro-4-nitro-5-((R)-2,2,2-trifluoro-1-methoxymethyl-ethoxy)-benzyl]-4-hydroxy-tetrahydro-thiopyran-3-yl}-carbamic acid tert-butyl ester (529 mg 1 mmol, example 40a)) and gold(III)chloride×4H$_2$O (8.24 mg, 0.02 mmol) in MeOH (5.3 mL) at room temperature was added 30% H$_2$O$_2$ (153 µl, 1.5 mmol). Stirring was continued for 7 h. The reaction mixture was diluted with EtOAc (150 mL) and was washed with 1N aq. K$_2$CO$_3$ solution, water, 10% aq. Na$_2$S$_2$O$_3$ solution, water and brine. The organic phase was dried over Na$_2$SO$_4$, filtered and evaporated. The title compounds were obtained after purification by flash-chromatography on silica (16 g, EtOAc to EtOAc-ETA 97:3) as light yellow foams: (1R,3R,4S,5S)-5-[3-Fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester: TLC (EtOAc-ETA 95:5) Rf=0.28; HPLC Rt$_F$=2.35 min; ESIMS [M+H]$^+$=545; [M+NH$_4$]$^+$=562; $^1$H NMR (600 MHz, DMSO-d$_6$): δ 7.28 (s, 1H), 7.12 (d, 1H), 6.825 (d, 1H), 5.65 (broad, 1H), 5.10 (d, 1H), 4.00 (m, 1H), 3.83 (dd, 1H), 3.72 (dd, 1H), 3.31 (s, 3H), 3.15-3.05 (m, 2H), 2.90 (d, 1H), 2.78 (d, 1H), 2.72 (dd, 1H), 2.55-2.49 (m, 2H), 2.35 (t, 1H), 1.39 (s, 9H). (1S,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester: TLC (EtOAc-ETA 95:5) Rf=0.22; HPLC Rt$_F$=2.35 min; ESIMS [M+H]$^+$=545; [M+NH$_4$]$^+$=562; $^1$H NMR (600 MHz, DMSO-d$_6$): δ 7.28 (s, 1H), 7.12 (d, 1H), 6.88 (d, 1H), 5.68 (s, 1H), 5.15 (d, 1H), 3.82 (dd, 1H), 3.73 (dd, 1H), 3.44 (m, 1H), 3.31-3.25 (m, 4H), 3.19-3.02 (m, 3H), 2.62-2.55 (m, 2H), 2.35 (t, 1H), 1.88 (m, 1H), 1.39 (s, 9H).

b) (1R,3R,4S,5S)-3-Amino-5-[3-fluoro-4-nitro-5-((R)-2,2,2-trifluoro-1-methoxymethyl-ethoxy)-benzyl]-1-oxo-tetrahydro-thiopyran-4-ol hydrochloride To a solution of (1R,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl (5.1 g, 9.37 mmol) in MeOH (15 mL) was added 3N HCl in MeOH (15 mL), and the solution was stirred at room temperature for 22 h. Evaporation of the solvent and repeated trituration with MeOH and toluene afforded the title compound as beige, crystalline powder: HPLC Rt$_F$=1.41 min; ESIMS [M+H]$^+$=445; $^1$H NMR (600 MHz, DMSO-d$_6$): δ 8.13 (s, 3H, NH$_3$), 7.35 (s, 1H), 7.15 (d, 1H), 6.01 (d, 1H), 5.70-5.62 (m, 1H), 3.76 (dd, 1H), 3.68 (dd, 1H), 3.52 (m, 1H), 3.33-3.25 (m, 4H), 3.16 (m, 2H), 2.85 (d, 1H), 2.80 (t, 1H), 2.68 (m, 1H), 2.54 (m, 2H).

c) (1R,3R,4S,5S)-3-(3-tert-Butyl-benzylamino)-5-[3-fluoro-4-nitro-5-((R)-2,2,2-trifluoro-1-methoxymethyl-ethoxy)-benzyl]-1-oxo-tetrahydro-thiopyran-4-ol The title compound was prepared in an analogous manner as described for example 1h), starting from (1R,3R,4S,5S)-3-amino-5-[3-fluoro-4-nitro-5-((R)-2,2,2-trifluoro-1-methoxy-methyl-ethoxy)-benzyl]-1-oxo-tetrahydro-thiopyran-4-ol hydrochloride (3.45 g, 7.17 mmol) and 3-tert-butyl-benzaldehyde, and was obtained after purification by flash-chromatography (hexane-EtOAc-MeOH 50:50:3 to 0:20:1) as a light yellow foam: HPLC Rt$_F$=2.18 min; ESIMS [M+H]$^+$=591; $^1$H NMR (600 MHz, CDCl$_3$): δ 7.33 (s, 1H), 7.29 (s, 1H), 7.25-7.20 (m, 2H), 7.13 (d, 1H), 7.10 (d, 1H), 5.65 (m, 1H), 5.12 (d, 1H), 3.81 (m, 2H), 3.70 (dd, 1H), 3.62 (d, 1H), 3.30 (s, 3H), 3.23-3.10 (m, 4H), 2.75 (m, 1H), 2.69 (m, 1H), 2.48-2.33 (m, 3H), 1.25 (s, 9H).

d) (1R,3S,4S,5R)-3-[4-Amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-ol (cis-sulfoxide)

A solution of (1R,3R,4S,5S)-3-(3-tert-butyl-benzylamino)-5-[3-fluoro-4-nitro-5-((R)-2,2,2-tri-fluoro-1-methoxymethyl-ethoxy)-benzyl]-1-oxo-tetrahydro-thiopyran-4-ol (1.34 g, 2.27 mmol) in EtOH (27 mL) was hydrogenated at 1 bar over Ra—Ni at 40° C. for 7 h. Filtration over Celite and charcoal afforded the title compound after evaporation as an amorphous solid: TLC (toluene-ETA 95:5) Rf=0.28; HPLC Rt$_{H1}$=0.86 min; ESIMS [M+H]$^+$=561; $^1$H NMR (600 MHz, CDCl$_3$): δ 7.34 (s, 1H), 7.24 (m, 2H), 7.12 (m, 1H), 6.72 (s, 1H), 6.63 (d, 1H), 5.08 (s, 1H), 5.00 (s, 1H), 4.57 (s, 2H), 3.80-3.67 (m, 3H), 3.57 (m, 1H), 3.30 (s, 3H), 3.18-3.05 (m, 3H), 2.98 (m, 1H), 2.70 (m, 1H), 2.49-2.23 (m, 5H), 1.25 (s, 9H).

Example 42

(1S,3S,4S,5R)-3-[4-Amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-ol (trans-sulfoxide)

a) (1S,3R,4S,5S)-3-Amino-5-[3-fluoro-4-nitro-5-((R)-2,2,2-trifluoro-1-methoxymethyl-ethoxy)-benzyl]-1-oxo-tetrahydro-thiopyran-4-ol trifluoroacetate salt The title compound was prepared in analogous manner as described for example 8h) from (1S,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl (3.079 g, 5.65 mmol) to yield the TFA salt as a light yellow foam: HPLC Rt$_F$=1.37 min; ESIMS [M+H]$^+$=445; $^1$H NMR (600 MHz, DMSO-d$_6$): δ 8.26 (s, 3H), 7.33 (s, 1H), 7.15 (d, 1H), 6.01 (s, 1H), 5.70-5.62 (m, 1H), 3.80 (dd, 1H), 3.71 (m, 1H), 3.51 (d, 1H), 3.35 (t, 1H), 3.31 (s, 3H), 3.20-3.10 (m, 3H), 2.80 (t, 1H), 2.60-2.51 (m, 2H), 1.96 (m, 1H).

b) (1S,3R,4S,5S)-3-(3-tert-Butyl-benzylamino)-5-[3-fluoro-4-nitro-5-((R)-2,2,2-trifluoro-1-methoxymethyl-ethoxy)-benzyl]-1-oxo-tetrahydro-thiopyran-4-ol The title compound was prepared in an analogous manner as described for example 1h, starting from (1S,3R,4S,5S)-3-amino-5-[3-fluoro-4-nitro-5-((R)-2,2,2-trifluoro-1-methoxy-methyl-ethoxy)-benzyl]-1-oxo-tetrahydro-thiopyran-4-ol TFA salt (310 mg, 0.7 mmol) and 3-tert-butyl-benzaldehyde and was obtained after purification by flash-chromatography (hexane-(EtOAc-MeOH 9:1) gradient) as a light yellow foam: TLC (EtOAc-MeOH 9:1) Rf=0.38; HPLC Rt$_{H1}$=1.05 min; ESIMS [M+H]+=591; $^1$H NMR (600 MHz, CDCl$_3$): δ 7.36 (s, 1H), 7.28 (s, 1H), 7.23 (m, 2H), 7.13 (d, 1H), 7.11 (d, 1H), 5.66 (m, 1H), 5.16 (d, 1H), 3.83-3.79 (m, 2H), 3.69 (dd, 1H), 3.63 (d, 1H), 3.55 (m, 1H), 3.30 (s, 3H), 3.14 (m, 2H), 3.00 (d, 1H), 2.55 (m, 1H), 2.5-2.4 (m, 3H), 1.95 (m, 1H), 1.25 (s, 9H).

c) (1S,3S,4S,5R)-3-[4-Amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-ol (trans-sulfoxide)

The title compound was prepared in an analogous manner as described for example 41d) from (1S,3R,4S,5S)-3-(3-tert-butyl-benzylamino)-5-[3-fluoro-4-nitro-5-((R)-2,2,2-trifluoro-1-methoxymethyl-ethoxy)-benzyl]-1-oxo-tetrahydro-thiopyran-4-ol as an amorphous solid: TLC (EtOAc-MeOH 9:1) Rf=0.48; HPLC Rt$_{H1}$=0.91 min; ESIMS [M+H]$^+$=561; $^1$H NMR (600 MHz, CDCl$_3$): δ 7.36 (s, 1H), 7.24 (m, 2H), 7.13 (d, 1H), 6.74 (s, 1H), 6.65 (d, 1H), 5.15 (s, 1H), 5.06 (s, 1H), 4.58 (s, 2H), 3.83-3.79 (m, 2H), 3.73 (m, 2H), 3.63 (dd, 1H), 3.53 (d, 1H), 3.30 (s, 3H), 3.03 (m, 1H), 2.97 (m, 2H), 2.49-2.32 (m, 4H), 1.70-2.62 (m, 1H), 1.25 (s, 9H).

Example 43

(3S,4S,5R)-3-[4-Amino-3-fluoro-5-((R)-2,2,2-trifluoro-1-methoxymethyl-ethoxy)-benzyl]-5-[3-(1-methyl-cyclopropyl)-benzylamino]-1-oxo-hexahydro-1lambda*4*-thiopyran-4-ol hydrochloride a) 3-(1-Methyl-cyclopropyl)benzaldehyde The title compound was prepared following a procedure described in *J. Am. Chem. Soc.* 2007, 127, 12440-12441, starting from 2-(3-isopropenyl-phenyl)-[1,3]dioxolane and was obtained as a light yellow oil: TLC (cyclohexane-EtOAc 80:20) Rf=0.52; HPLC Rt$_{G2}$=1.35 min; $^1$H NMR (400 MHz, DMSO-d$_6$): δ 9.98 (s, 1H), 7.74 (s, 1H), 7.68 (d, 1H), 7.51 (m, 2H), 1.40 (s, 3H), 0.89 (t, 2H), 0.81 (m, 2H).

b) (1R,3S,4S,5R)-3-[4-Amino-3-fluoro-5-((R)-2,2,2-trifluoro-1-methoxymethyl-ethoxy)-benzyl]-5-[3-(1-methyl-cyclopropyl)-benzylamino]-1-oxo-tetrahydro-thiopyran-4-ol The title compound can be prepared in an analogous manner as described for example 41 steps c) and d) from (1R,3R,4S,5S)-3-amino-5-[3-fluoro-4-nitro-5-((R)-2,2,2-trifluoro-1-methoxymethyl-ethoxy)-benzyl]-1-oxo-tetrahydro-thiopyran-4-ol hydrochloride and 3-(1-methyl-cyclopropyl)benzaldehyde to yield the title compound as a yellowish foam: TLC (CH$_2$Cl$_2$-MeOH 9:1) Rf=0.48; HPLC Rt$_{G3}$=1.70 min; ESIMS [M+H]$^+$=559.3; $^1$H NMR (400 MHz, DMSO-d$_6$): δ 7.22-7.18 (m, 2H), 7.11 (d, 1H), 7.07 (d, 1H), 6.72 (s, 1H), 6.64 (d, 1H), 5.09 (m, 1H), 4.99 (d, 1H), 4.58 (s, 2H), 3.75 (m, 3H), 3.59 (d, 1H), 3.32 (s, 3H), 3.19-3.09 (m, 3H), 2.98 (m, 1H), 2.69 (m, 1H), 2.45-2.25 (m, 4H), 1.36 (s, 3H), 0.83 (m, 2H), 0.72 (m, 2H).

Example 44

(1R,3S,4S,5R)-3-[4-Amino-3-fluoro-5-((R)-2,2,2-trifluoro-1-methoxymethyl-ethoxy)-benzyl]-1-oxo-5-[3-(2,2,2-trifluoro-1,1-dimethyl-ethyl)-benzylamino]-tetrahydro-thiopyran-4-ol a) 2-hydroxy-5-(2,2,2-trifluoro-1,1-dimethyl)benzaldehyde To a mixture of 2-methoxy-5-(2,2,2-trifluoro-1,1-dimethyl)benzaldehyde (6.7 g, 27.2 mmol) was added dropwise an 1M CH$_2$Cl$_2$ solution of boron tribromide (130 mL, 130 mmol) keeping the temperature below 30° C. The mixture was stirred at room temperature for 21 h. The reaction was quenched with ice water and extracted with EtOAc. The combined organic phases were washed with water and brine, dried over Na$_2$SO$_4$, filtered and concentrated. The crude product was purified by column chromatography on silica gel (hexane-EtOAc 19:1) to furnish the title compound as a colorless oil: HPLC Rt$_D$=7.43 min; ESIMS [M+H]$^+$=231; $^1$H NMR (400 MHz, CDCl$_3$): δ10.99 (s, 1H), 9.91 (s, 1H), 7.66 (dd, 2H), 7.0 (d, 1H), 1.59 (m, 6H), $^{19}$F-NMR (400 MHz, CDCl$_3$): δ −77.04.

b) 2-trifluoromethanesulfonyl-5-(2,2,2-trifluoro-1,1-dimethyl)benzaldehyde

To an ice cold solution of 2-hydroxy-5-(2,2,2-trifluoro-1,1-dimethyl)benzaldehyde (7.07 g, 30.4 mmol) and pyridine (4.9 mL, 61 mmol) in CH$_2$Cl$_2$ (50 mL) was added dropwise triflic anhydride (7.084 mL, 45.7 mmol) keeping the temperature below 10° C. and the mixture was stirred at 0° C. for 45 min. The reaction mixture was quenched with aq. NaHCO$_3$ solution and ice and the organic layer was separated. The aqueous layer was extracted with Et$_2$O and the combined organic layers were washed with water, brine, dried over Na$_2$SO$_4$, filtered and concentrated to give the title compound after purification by column chromatography on silica gel (hexane-acetone 19:1) as a white solid: HPLC Rt$_D$=7.75 min; ESIMS [M+H]$^+$=365; $^1$H NMR (400 MHz, CDCl$_3$): δ 10.28 (s, 1H), 8.10 (d, 1H), 7.85 (dd, 1H), 7.42 (d, 1H), 1.63 (m, 6H), $^{19}$F-NMR (400 MHz, CDCl$_3$): δ −73.20, −76.59.

c) 3-(2,2,2-trifluoro-1,1-dimethyl)benzaldehyde

A mixture of 2-trifluoromethanesulfonyl-5-(2,2,2-trifluoro-1,1-dimethyl)benzaldehyde (8.24 g, 22.6 mmol), 10% Pd/C (0.82 g) and diethylamine (2.8 mL, 27.1 mmol) in MeOH (50 mL) was stirred at room temperature under hydrogen pressure from 10 to 3.7 bar within 25 min. The reaction mixture was filtered over Celite and the filtrate is concentrated. The crude product was purified by column chromatography on silica gel (hexane-EtOAc 95:5) to provide the title compound as a light yellow oil: HPLC Rt$_D$=7.39 min, $^1$H NMR (400 MHz, CDCl$_3$): δ 10.04 (s, 1H), 8.01 (s, 1H), 7.85 (dd, 1H), 7.83 (dd, 1H), 7.55 (t, 1H) 1.63 (m, 6H), $^{19}$F-NMR (400 MHz, CDCl$_3$): δ −76.6.

d) (1R,3S,4S,5R)-3-[3-Fluoro-4-nitro-5-((R)-2,2,2-trifluoro-1-methoxymethyl-ethoxy)-benzyl]-1-oxo-5-[3-(2,2,2-trifluoro-1,1-dimethyl-ethyl)-benzylamino]-tetrahydro-thio-pyran-4-ol The title compound was prepared in an analogous manner as described for example 1h, starting from (1R,3R,4S,5S)-3-amino-5-[3-fluoro-4-nitro-5-((R)-2,2,2)-trifluoro-1-methoxy-methyl-ethoxy)-benzyl]-1-oxo-tetrahydro-thiopyran-4-ol hydrochloride (279 mg, 0.5 mmol) and 3-(2,2,2-trifluoro-1,1-dimethyl)benzaldehyde (108 mg, 0.5 mmol): TLC (toluene-ETA 85:15) Rf=0.30; ESIMS [M+H]$^+$=645.

e) (1R,3S,4S,5R)-3-[4-Amino-3-fluoro-5-((R)-2,2,2-trifluoro-1-methoxymethyl-ethoxy)-benzyl]-1-oxo-5-[3A2,2,2-trifluoro-1,1-dimethyl-ethyl)-benzylamino]-tetrahydro-thiopyran-4-ol hydrochloride The title compound was prepared in an analogous manner as described for example 1j, starting from (1R,3S,4S,5R)-3-[3-fluoro-4-nitro-5-((R)-2,2,2-trifluoro-1-methoxymethyl-ethoxy)-benzyl]-1-oxo-5-[3-(2,2,2-trifluoro-1,1-dimethylethyl)-benzylamino]-tetrahydro-thiopyran-4-ol. Purification of the free base over silica gel (EtOAc to EtOAc-MeOH 95:5) and subsequent transformation into the hydrochloride salt with 1N HCl in Et$_2$O afforded the title compound as a white solid: TLC (toluene-ETA 85:15) Rf=0.42, HPLC Rt$_F$=2.05 min; ESIMS [M+H]$^+$=615; $^1$H NMR (free base, 600 MHz, DMSO-d$_6$): δ 7.50 (s, 1H), 7.39 (d, 1H), 7.36-7.30 (m, 2H), 6.72 (s, 1H), 6.63 (d, 1H), 5.05 (m, 1H), 5.01 (d, 1H), 4.60 (s, 2H), 3.82 (d, 1H), 3.75-3.68 (m, 2H), 3.65 (d, 1H), 3.31 (s, 3H), 3.18-3.03 (m, 3H), 2.96 (dd, 1H), 2.68 (dd, 1H), 2.48-2.26 (m, 4H), 1.55 (s, 6H).

Example 45

(1R,3S,4S,5R)-3-[4-Amino-3-fluoro-5-((R)-2,2,2-trifluoro-1-methoxymethyl-ethoxy)-benzyl]-5-{[5-(2,2-dimethyl-propyl)-isoxazol-3-ylmethyl]-amino}-1-oxo-tetra-hydro-thiopyran-4-ol dihydrochloride a) 5-(2,2-Dimethyl-propyl)-isoxazole-3-carbaldehyde To a solution of 5-(2,2-dimethyl-propyl)-isoxazole-3-carbonitrile (821 mg, 5 mmol) in Et$_2$O (15 mL) and n-hexane (50 mL) was added dropwise at −78° C. an 1.7M toluene solution of DIBAL (11.8 mL, 20 mmol) keeping the temperature below −70° C. The mixture was stirred at −78° C. for 1 h. The reaction was quenched with EtOAc (7.5 mL), allowed to warm to 0° C., then sat. NH$_4$Cl solution (25 mL) and 1M HCl (50 mL) were added and the mixture stirred at room temperature for 2 h. The layers were separated and the aqueous phase was extracted with EtOAc. The combined organic phases were dried over Na$_2$SO$_4$, filtered and concentrated. The crude product was purified by column chromatography on silica gel (cyclohexane to cyclohexane-EtOAc 80:20) to furnish title compound as a colorless oil: TLC (cyclohexane-EtOAc 80:20) Rf=0.44; ESIMS [M+H]$^+$=168; $^1$H NMR (400 MHz, DMSO-d$_6$): δ 10.06 (s, 1H), 6.66 (s, 1H), 2.74 (s, 2H), 0.92 (s, 9H).

b) (1R,3S,4S,5R)-3-[4-Amino-3-fluoro-5-((R)-2,2,2-trifluoro-1-methoxymethyl-ethoxy)-benzyl]-5-{[5-(2,2-dim ethyl-propyl)-isoxazol-3-ylmethyl]amino}-1-oxo-tetra-hydro-thiopyran-4-ol dihydrochloride The title compound can be prepared in an analogous manner as described for example 41 steps c) and d) from (1R,3R,4S,5S)-3-amino-5-[3-fluoro-4-nitro-5-((R)-2,2,2-trifluoro-1-methoxymethyl-ethoxy)-benzyl]-1-oxo-tetrahydro-thiopyran-4-ol hydrochloride and 5-(2,2-dimethyl-propyl)-isoxazole-3-carbaldehyde and subsequent transformation into the hydrochloride salt with 5N HCl in Et$_2$O to afford the title compound as a beige foam: TLC (CH$_2$Cl$_2$-MeOH 9:1) Rf=0.53; HPLC Rt$_{G3}$=1.77 min; ESIMS [M+H]$^+$=566; $^1$H NMR (400 MHz, DMSO-d$_6$): δ 6.73 (s, 1H), 6.64 (d, 1H), 6.25 (s, 1H), 5.12-5.06 (m, 1H), 4.99 (d, 1H), 4.59 (s, 2H), 3.83-3.68 (m, 4H), 3.33 (s, 3H), 3.17-3.06 (m, 3H), 3.00-2.97 (m, 1H), 2.72-2.68 (m, 1H), 2.63 (s, 2H), 2.45-2.27 (m, 4H), 0.93 (s, 9H).

Example 46

(1R,3S,4S,5R)-3-[4-Amino-3-fluoro-5-((R)-2,2,2-trifluoro-1-methoxymethyl-ethoxy)-benzyl]-5-{[1-(2,2-dimethyl-propyl)-1H-pyrazol-4-ylmethyl]-amino}-1-oxo-tetra-hydro-thiopyran-4-ol dihydrochloride a) 1-(2,2-Dimethyl-propyl)-1H-pyrazole-4-carbaldehyde A flask charged with anhydrous DMF (400 mL) was cooled to 0° C., to which phosphorous oxychloride (114 g, 0.74 mol) was added dropwise, and the temperature was kept below 10° C. The stirring was continued for 1 h and it was allowed to rise to room temperature. Then it was cooled to 0° C. again, and a solution of 1-(2,2-dimethyl-propyl)-1H-pyrazole (51.1 g, 0.37 mol, CAS registry 725746-83-8) in DMF (100 mL) was added dropwise. Then it was heated to 100° C. overnight. After cooling, the reaction was quenched by slow addition of cold water, and it was neutralized with aqueous NaHCO$_3$ solution and extracted with EtOAc. The combined organic layers were washed with brine, dried over MgSO$_4$ and concentrated. The resulting residue was purified by column chromatograph on silicagel (petroleum ether-EtOAc 10:1) to give the title compound as light yellow oil: ESIMS [M+H]$^+$=167; $^1$H NMR (400 MHz, DMSO-d$_6$): δ 9.80 (s, 1H), 8.42 (s, 1H), 7.98 (s, 1H), 3.99 (s, 2H), 0.90 (s, 9H).

b) (1R,3S,4S,5R)-3-[4-Amino-3-fluoro-5-((R)-2,2,2-trifluoro-1-methoxymethyl-ethoxy)-benzyl]-5-{[1-(2,2-dimethyl-propyl)-1H-pyrazol-4-ylmethyl]-amino}-1-oxo-tetra-hydro-thiopyran-4-ol dihydrochloride The title compound can be prepared in an analogous manner as described for example 41 steps c) and d) from (1R,3R,4S,5S)-3-amino-5-[3-fluoro-4-nitro-5-((R)-2,2,2-trifluoro-1-methoxymethyl-ethoxy)-benzyl]-1-oxo-tetrahydro-thiopyran-4-ol hydrochloride and 1-(2,2-dimethyl-propyl)-1H-pyrazole-4-carbaldehyde and subsequent transformation into the hydrochloride salt with 5N HCl in Et$_2$O to afford the title compound as a beige foam: TLC (CH$_2$Cl$_2$-MeOH 9:1) Rf=0.35; HPLC Rt$_{G3}$=1.51 min; ESIMS [M+H]$^+$=565; $^1$H NMR (400 MHz, DMSO-d$_6$): δ 7.53 (s, 1H), 7.34 (s, 1H), 6.72 (s, 1H), 6.64 (d, 1H), 5.12-5.06 (m, 1H), 4.96 (d, 1H), 4.59 (s, 2H), 3.84 (s, 2H), 3.77-3.64 (m, 3H), 3.48 (d, 1H), 3.33 (s, 3H), 3.18-3.05 (m, 3H), 2.98 (dd, 1H), 2.71 (d, 1H), 2.46-2.26 (m, 5H), 0.88 (s, 9H).

Example 47

(1R,3S,4S,5R)-3-[4-Amino-3-fluoro-5-(R)-2,2,2-trifluoro-1-methoxymethyl-ethoxy)-benzyl]-5-(5-tert-butyl-2-fluoro-benzylamino)-1-oxo-tetrahydro-thiopyran-4-ol a) 5-tert-Butyl-2-fluoro-benzaldehyde A solution of 1-tert-butyl-4-fluoro-benzene (4.54 g, 30 mmol) in THF (100 mL) cooled at −78° C. was treated dropwise with a 2.5M solution of nBuLi in hexane (24 mL, 59 mmol). The reaction mixture was stirred for 5 h at −45° C. then DMF (3.5 mL, 44 mmol) was added at −75° C. and the reaction mixture was stirred for 0.5 h at −75° C. The reaction mixture was poured onto 1N aq. HCl and extracted with Et$_2$O. Combined organic layers were washed with brine, dried over Na₂SO₄, filtered and evaporated. The title compound was obtained after chromatographic purification (Combi Flash, 40 g silica gel, hexane to hexane-EtOAc 10:1) as a light yellow oil: TLC (hexane-EtOAc 10:1) R$_f$=0.48, HPLC Rt$_A$=2.10 min; ¹H NMR (400 MHz, CDCl₃): δ10.36 (s, 1H), 7.85 (dd, 1H), 7.62 (m, 1H), 7.08 (dd, 1H), 1.32 (s, 9H).

b) (1R,3S,4S,5R)-3-[4-Amino-3-fluoro-5-((R)-2,2,2-trifluoro-1-methoxymethyl-ethoxy)-benzyl]-5-(5-tert-butyl-2-fluoro-benzylamino)-1-oxo-tetrahydro-thiopyran-4-ol The title compound can be prepared in an analogous manner as described for example 41 steps c) and d) from (1R,3R,4S,5S)-3-(5-tert-butyl-2-fluoro-benzylamino)-5-[3-fluoro-4-nitro-5-((R)-2,2,2-trifluoro-1-methoxymethyl-ethoxy)-benzyl]-1-oxo-tetrahydro-thiopyran-4-ol and 5-tert-butyl-2-fluoro-benzaldehyde and was obtained after purification by column chromatography on silica gel (EtOAc/5% MeOH) 70-0% hexane as a colorless foam: HPLC Rt$_{H1}$=2.52 min; ESIMS [M+H]⁺=579; ¹H NMR (600 MHz, DMSO-d₆): δ 7.74 (m, 1H), 7.47 (m, 1H), 7.19 (t, 1H), 6.77 (s, 1H), 6.70 (d, 1H), 6.67 (d, 3H), 5.13 (m, 1H), 4.31-4.20 (m, 2H), 3.75-3.70 (m, 2H), 3.64-3.60 (m, 2H), 3.47 (d, 1H), 3.30 (s, 3H), 3.09-2.98 (m, 2H), 2.79 (m, 1H), 2.48-2.39 (m, 3H), 1.28 (s, 9H).

Example 48

(1R,3S,4S,5R)-3-[4-Amino-3-fluoro-5-((R)-2,2,2-trifluoro-1-methoxymethyl-ethoxy)-benzyl]-5-(3-isopropyl-5-methoxy-benzylamino)-1-oxo-tetrahydro-thiopyran-4-ol a) 1-Bromo-3-isopropyl-5-methoxy-benzene To a solution of 1,3-dibromo-5-methoxy-benzene (20.7 g, 78 mmol) in dry THF (100 mL) was added under nitrogen a 1.6 M solution of nBuLi in hexane (48.7 mL, 78 mmol) at such a rate that the reaction temperature did not rise above −50° C. After the addition the mixture was cooled to −70° C. and acetone (6.86 mL, 78 mmol) was added over a 5 min period. After 2 min the reaction was quenched with saturated NH₄Cl solution and stirred for 10 min. The mixture was diluted with water and extracted with TBME. The organic layer was dried with MgSO₄, filtered and evaporated. Chromatographic purification over silica gel (hexane-EtOAc 95:5 to 85:15) provided impure 2-(3-bromo-5-methoxy-phenyl)-propan-2-ol as a yellow oil: TLC (hexane-AcOEt 6:1) Rf=0.22; HPLC Rt$_{H1}$=2.35 min; ESIMS [M−OH]⁻=227,229; ¹H NMR (400 MHz, CDCl₃): δ 7.27 (t, 1H), 7.02 (dd, 1H), 6.97 (dd, 1H), 3.83 (s, 3H), 1.59 (s, 6H). This material was treated with (±) camphor sulfonic acid (70 mg) in refluxing hexane with the azeotropical removal of water. After 1 h the cooled reaction mixture is diluted with TBME, washed with 5% aq. NaHCO₃, dried with MgSO₄, filtered and evaporated. Chromatographic purification over silica gel (hexane-toluene 0-10%) gave impure 1-bromo-3-iso-propenyl-5-methoxy-benzene as a slightly yellow oil: ¹H NMR (400 MHz, CDCl₃): δ 7.27 (t, 1H), 7.07 (s, 1H), 6.99 (s, 1H), 5.48 (s, 1H), 5.16 (s, 1H), 3.75 (s, 3H), 2.07 (s, 3H). This material was stirred in the presence of Ra—Ni catalyst (5 g) in EtOH (15 mL) under a hydrogen atmosphere for 18 h. The mixture was filtered over a bed of Celite and evaporated to obtain a yellow oil that contained still some starting material. It was taken up in CH₂Cl₂ (10 mL) and treated with meta-chlorperbenzoic acid (250 mg). The mixture was washed with sodium sulfite solution, followed by water and evaporated. Chromatography over silica gel (hexane-CH₂Cl₂ 100:1 to 9:1) gave the title compound as a colorless oil: TLC (hexane-EtOAc 9:1) Rf=0.50; HPLC Rt$_{H1}$=3.79 min; ¹H NMR (400 MHz, CDCl₃): δ 6.97 (t, 1H), 6.86 (t, 1H), 6.69 (t, 1H), 3.78 (s, 3H), 2.84 (heptet, 1H), 1.22 (d, 6H).

b) 3-Isopropyl-5-methoxy-benzaldehyde

A solution of 1-bromo-3-isopropyl-5-methoxy-benzene (1.06 g, 4.63 mmol) in dry THF (10 mL) was cooled to −78° C. under nitrogen atmosphere. A 1.6 M solution of nBuLi in hexane (2.9 mL, 4.63 mmol) was added at once, followed within 1 min by DMF (0.356 mL, 4.63 mmol). After 1 min the mixture was poured onto 10 mL 1N aq. HCl, stirred for 5 min and extracted with TBME. The organic phase was washed with brine, dried with MgSO₄ and evaporated to give the title compound sufficiently pure for further use: TLC (AcOEt-hexane 1:9) Rf=0.40; HPLC Rt$_{H1}$=2.97 min; ESIMS [M+H]⁺=179; ¹H NMR (400 MHz, CDCl₃): δ 9.95 (s, 1H), 7.36 (s, 1H), 7.22 (s, 1H), 7.05 (s, 1H), 3.85 (s, 3H), 2.96 (heptet, 1H), 1.29 (d, 6H).

c) {(1R,3R,4S,5S)-5-[4-Amino-3-fluoro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester The title compound was prepared in an analogous manner as described for example 1j, starting from {(1R,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester (example 41a): TLC (EtOAc) Rf=0.30; HPLC Rt$_F$=1.99 min; ESIMS [M+H]⁺=515; [M+H-isobutylene]⁺=459.

d) (1R,3R,4S,5S)-3-Amino-5-[4-amino-3-fluoro-5-((R)-2,2,2-trifluoro-1-methoxymethyl-ethoxy)-benzyl]-1-oxo-tetrahydro-thiopyran-4-ol trifluoroacetate salt The title compound was prepared in analogous manner as described for example 8h from {(1R,3R,4S,5S)-5-[4-amino-3-fluoro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester (2.05 g, 3.98 mmol) to yield the TFA salt as a colorless foam: HPLC Rt$_F$=1.13 min; ESIMS [M+H]⁺=415; ¹H NMR (600 MHz, DMSO-d₆): δ 8.05 (s broad, 3H), 6.74 (s, 1H), 6.68 (d, 1H), 5.85 (s broad, 2H), 5.05 (d, 1H), 3.75 (m, 2H), 3.52 (s broad, 1H), 3.31 (s, 3H), 3.25 (t, 1H), 3.15 (d, 1H), 3.00 (d, 1H), 2.77 (d, 1H), 2.70 (t, 1H), 2.48-2.37 (m, 3H).

e) (1R,3S,4S,5R)-3-[4-Amino-3-fluoro-5-((R)-2,2,2-trifluoro-1-methoxy-me-thyl-ethoxy)-benzyl]-5-(3-isopropyl-5-methoxy-benzylamino)-1-oxo-tetrahy-dro-thiopy-ran-4-ol A solution of (1R,3R,4S,5S)-3-amino-5-[4-amino-3-fluoro-5-((R)-2,2,2-trifluoro-1-methoxy-methyl-ethoxy)-benzyl]-1-oxo-tetrahydro-thiopyran-4-ol trifluoroacetate salt (0.25 g, 0.473 mmol, example 48d), 3-isopropyl-5-methoxy-benzaldehyde (0.084 g, 0.473 mmol) and NaOAc (0.078 g, 0.946 mmol) were stirred in CH₂Cl₂-MeOH 1:1 (2 mL) in the presence of 4A mol sieves for 16 h. NaBH₃CN (0.060 g, 0.946 mmol) and AcOH (0.1 mL) were added and stirred for 1 h. The reaction was quenched with 2N aq. HCl followed by MeOH after 30 min. The mixture was filtered over Celite, diluted with 10% aq. Na$_2$CO$_3$ solution and was extracted with EtOAc. The combined organic layers were dried over Na$_2$SO$_4$, filtered and evaporated. Purification by preparative HPLC (Sunfire C18 OBD 5 µm, 100×30, 20-40% ACN in water+0.1% TFA gradient, 25 min) gave the title compound as a light yellow foam: TLC (AcOEt-MeOH 19:1) Rf=0.48; HPLC Rt$_{H1}$=2.37 min; ESIMS [M+H]$^+$=577; $^1$H NMR (400 MHz, CD$_3$OD): δ 6.87 (s, 1H), 6.80-6.68 (m, 3H), 6.70 (s, 1H), 4.96-4.82 (m, 2H), 3.89-3.67 (m, 4H), 3.82 (s, 3H), 3.45 (s, 3H), 3.4-3.18 (m, 3H), 2.90 (m, 2H), 2.64-2.39 (m, 4H), 1.28 (d, 6H).

Example 49

(1R,3S,4S,5R)-3-[4-Amino-3-fluoro-5-((R)-2,2,2-trifluoro-1-methoxymethyl-ethoxy)-benzyl]-5-(3-tert-butyl-5-methoxy-benzylamino)-1-oxo-tetrahydro-thiopyran-4-ol dihydrochloride a) Trifluoro-methanesulfonic acid 3-tert-butyl-5-methoxy-phenyl ester To an ice cooled solution of 3-tert-butyl-5-methoxy-phenol (35.58 g, 197 mmol) and NEt$_3$ (41.3 mL, 296 mmol) in CH$_2$Cl$_2$ (150 mL) is added dropwise triflic anhydride (36.7 mL, 217 mmol) while keeping the temperature below 15° C. After 10 min the mixture was poured onto ice-water and extracted with TBME. The organic layers were washed with water, 1N aq. HCl and brine, dried over Na$_2$SO$_4$, evaporated and chromatographed on silica gel with hexane-TBME (100:1 to 95:5) to yield the title compound as a slightly colored oil: TLC (hexane) Rf=0.25; LCMS Rt$_{H2}$=3.00 min; ESIMS [M+H]$^+$=313; $^1$H NMR (400 MHz, CDCl$_3$): δ 6.94 (s, 1H), 6.84 (s, 1H), 6.60 (s, 1H), 3.83 (s, 3H), 1.30 (s, 9H).

b) 3-tert-Butyl-5-methoxy-benzonitrile

A mixture of trifluoro-methanesulfonic acid 3-tert-butyl-5-methoxy-phenyl ester (60.67 g, 194 mmol), Zn(CN)$_2$ (15.97 g, 136 mmol), PPh$_3$ (8.15 g, 31.1 mmol) and Pd(OAc)$_2$ (1.745 g, 7.77 mmol) in dimethyl acetamide (174 mL) was heated at 150° C. for 16 h. The cold reaction mixture was poured onto water and TBME. The mixture was filtered over Celite, separated and the organic phase was washed with 1M H$_2$SO$_4$, water and brine. The product was dried over MgSO$_4$, evaporated and distilled at ~5 mbar, bp 94-100° C. to provide the title compound as a colorless oil: TLC (AcOEt-hexane 1:9) Rf=0.35; LCMS Rt$_{H2}$=2.73 min; ESIMS [M+H]$^+$=190; $^1$H NMR (400 MHz, CDCl$_3$): δ 7.27 (s, 1H), 7.13 (s, 1H), 6.93 (s, 1H), 3.82 (s, 3H), 1.30 (s, 9H).

c) tert-Butyl-5-methoxy-benzoic acid

A mixture of 3-tert-butyl-5-methoxy-benzonitrile (10 g, 52.8 mmol) and KOH (44.5 g, 85%) in diethylene glycol mono methyl ether (168 mL) was stirred at 100° C. for 16 h. The cold reaction mixture was poured onto ice-water and washed with TBME. The aqueous phase was acidified with conc. HCl and extracted with TBME. The organic phase was washed with brine and dried with MgSO$_4$. The title compound was obtained after crystallization from hexane as colorless crystals: LCMS Rt$_{H2}$=2.44 min; ESIMS [M+H]$^+$=209; $^1$H NMR (400 MHz, CDCl$_3$): δ 7.78 (s, 1H), 7.43 (s, 1H), 7.19 (s, 1H), 3.86 (s, 3H), 1.34 (s, 9H).

d) 3-tert-Butyl-5-methoxy-phenyl)-methanol

To a solution of tert-butyl-5-methoxy-benzoic acid (0.883 g, 4.24 mmol) in THF (5 mL) was added dropwise borane dimethylsulfide complex (0.58 mL, 5.51 mmol). The mixture was heated at reflux for 0.5 h. After cooling down the reaction was quenched carefully with 1.2 mL methanol, diluted with TBME and acidified with 1N aq. HCl. The mixture was washed with water, 1N NaOH and brine. The crude product was purified by column chromatography on silica gel (EtOAc-hexane 1:3) to give the title compound as a colorless oil: TLC (AcOEt-hexane 1:3) Rf=0.23; LCMS Rt$_{H2}$=2.38 min; ESIMS [M+H]$^+$=195; $^1$H NMR (400 MHz, CDCl$_3$): δ 6.97 (s, 1H), 6.89 (s, 1H), 6.73 (s, 1H), 4.68 (s, 2H), 3.80 (s, 3H), 1.30 (s, 9H).

e) 3-tert-butyl-5-methoxy-benzaldehyde

A mixture of 3-tert-butyl-5-methoxy-phenyl)-methanol (0.055 g, 0.283 mmol) and activated manganese(IV) oxide (0.246 g, 2.83 mmol) in EtOAc (1 mL) was stirred at room temperature for 1 h followed by heating at 50° C. for 1.5 h. The reaction mixture was diluted with EtOAc and filtered over Celite. The solvent was evaporated to yield the title compound as a colorless oil: TLC (AcOEt-hexane 1:3) Rf=0.46; LCMS Rt$_{H2}$=2.67 min; ESIMS [M+H]$^+$=193; $^1$H NMR (400 MHz, CDCl$_3$): δ 9.95 8 s, 1H), 7.50 (s, 1H), 7.20 (s, 2H), 3.88 (s, 3H), 1.34 (s, 9H).

f) (1R,3S,4S,5R)-3-[4-Amino-3-fluoro-5-((R)-2,2,2-trifluoro-1-methoxy-methyl-ethoxy)-benzyl]-5-(3-tert-butyl-5-methoxy-benzylamino)-1-oxo-tetrahydro-thiopyran-4-ol The title compound was prepared in an analogous manner as described for example 48g starting from (1R,3R,4S,5S)-3-amino-5-[4-amino-3-fluoro-5-((R)-2,2,2-trifluoro-1-methoxy-methyl-ethoxy)-benzyl]-1-oxo-tetrahydro-thiopyran-4-ol (example 48f) and 3-tert-butyl-5-methoxy-benzaldehyde and was obtained after purification by column chromatography on silica gel with (EtOAc/5% MeOH) 70-0% hexane as a colorless foam: TLC (AcOEt-MeOH 19:1) Rf=0.43; HPLC Rt$_{H1}$=2.55 min; ESIMS [M+H]$^+$=591; $^1$H NMR (600 MHz, DMSO-d$_6$): δ 6.92 (s, 1H), 6.75 (s, 2H), 6.72 (s, 1H), 6.67 (d, 3H), 5.01 (br s, 1H), 4.60 (br s, 2H), 3.77-3.68 (m, 3H), 3.73 (s, 3H), 3.61 (d, 1H), 3.30 (s 3H), 3.15 (m, 1H), 3.10 (m, 2H), 2.96 (m, 1H), 2.70 (m, 1H), 2.50-2.25 (m, 5H), 1.24 (s, 9H).

Example 50

(1R,3S,4S,5R)-3-[4-Amino-3-fluoro-5-((R)-2,2,2-trifluoro-1-methoxymethyl-ethoxy)-benzyl]-5-[(2,2-dimethyl-2,3-dihydro-benzofuran-6-ylmethyl)-amino]-1-oxo-tetrahydro-thiopyran-4-ol dihydrochloride a) (1R,3R,4S,5S)-3-[(2,2-Dimethyl-2,3-dihydro-benzofuran-6-ylmethyl)-amino]-5-[3-fluoro-4-nitro-5-((R)-2,2,2-trifluoro-1-methoxymethyl-ethoxy)-benzyl]-1-oxo-tetrahydro-thiopyran-4-ol The title compound was prepared in an analogous manner as described for example 1h, starting from (1R,3R,4S,5S)-3-amino-5-[3-fluoro-4-nitro-5-((R)-2,2,2-trifluoro-1-methoxy-methyl-ethoxy)-benzyl]-1-oxo-tetrahydro-thiopyran-4-ol hydrochloride salt (120 mg, 0.24 mmol) and 2,2-dimethyl-2,3-dihydro-benzofuran-6-carbaldehyde (52.8 mg, 0.264 mmol) and was obtained as a light yellow foam: ESIMS [M+H]$^+$=605, LCMS Rt$_f$=1.13 min. The product was directly used in the next step.

b) (1R,3S,4S,5R)-3-[4-Amino-3-fluoro-5-((R)-2,2,2-trifluoro-1-methoxymethyl-ethoxy)-benzyl]-5-[(2,2-dimethyl-2,3-dihydro-benzofuran-6-ylmethyl)-amino]-1-oxo-tetrahydro-thiopyran-4-ol dihydrochloride The title compound was prepared in an analogous manner as described for example 1j, starting from (1R,3R,4S,5S)-3-[(2,2-dimethyl-2,3-dihydro-benzofuran-6-ylmethyl)-amino]-5-[3-fluoro-4-nitro-5-((R)-2,2,2-trifluoro-1-methoxymethyl-ethoxy)-benzyl]-1-oxo-tetrahydro-thio-pyran-4-ol and subsequent transformation into the hydrochloride salt with 1N HCl in Et$_2$O afforded the title compound as off-white solid: ESIMS [M+H]$^+$=575, UPLC Rt$_F$=2.02 min; $^1$H NMR (500 MHz, DMSO-d6): δ 9.68-8.84 (m, 1H, NH), 7.22 (m, 1H), 6.99-6.95 (m, 2H), 6.78 (s, 1H), 6.70 (m, 1H), 6.37-5.71 (br, 3H, OH, NH$_2$), 5.17 (d, 1H), 5.14 (m, 1H), 4.21-4.06 (m, 2H), 3.76 (d, 2H), 3.57-3.45 (m, 3H), 3.33 (s, 3H), 3.06 (m, 1H), 3.01 (s, 2H), 2.90 (m, 1H), 2.78 (m, 1H), 2.46-2.34 (m, 3H), 1.43-1.39 (m, 6H).

Example 51

(1R,3S,4S,5R)-3-[4-Amino-3-fluoro-5-((R)-2,2,2-trifluoro-1-methoxymethyl-ethoxy)-benzyl]-5-[(R)-1-(3-tert-butyl-phenyl)-ethylamino]-1-oxo-tetrahydro-thiopyran-4-ol dihydrochloride a) (3R,4S,5S)-3-[(R)-1-(3-tert-Butyl-phenyl)-ethylamino]-5-[3-fluoro-4-nitro-5-((R)-2,2,2-trifluoro-1-methoxymethyl-ethoxy)-benzyl]-tetrahydro-thiopyran-4-ol and (3R,4S,5S)-3-[(S)-1-(3-tert-Butyl-phenyl)-ethylamino]-5-[3-fluoro-4-nitro-5-((R)-2,2,2-trifluoro-1-methoxymethyl-ethoxy)-benzyl]-tetrahydro-thiopyran-4-ol A solution of (3R,4S,5S)-3-amino-5-[3-fluoro-4-nitro-5-((R)-2,2,2-trifluoro-1-methoxymethyl-ethoxy)-benzyl]-tetrahydro-thiopyran-4-ol (0.535 g, 1.249 mmol, example 40b) and 1-(3-tert-butyl-phenyl)-ethanone (0.330 g, 1.873 mmol) in 3-methyl-1-butanol (10 mL) was refluxed for 3 h. More 1-(3-tert-butyl-phenyl)-ethanone (110 mg, 0.62 mmol) was added and reflux was continued for 9 h. The solvent was evaporated and the residual oil was taken up in MeOH (4 mL) and AcOH (0.1 mL) and NaBH$_3$CN (0.118 g, 1.873 mmol) were added and the mixture was stirred for 4 h. After quenching with 1 N aq. HCl the mixture was stirred for 45 min, basified with saturated K$_2$CO$_3$ solution and extracted with EtOAc. The organic layers were washed with brine, dried with Na$_2$SO$_4$ and evaporated. The mixture of diastereoisomers was separated by column chromatography on silica gel (hexane-EtOAc 35-100%) to provide the undesired less polar (3R,4S,5)-3-[(S)-1-(3-tert-butyl-phenyl)-ethylamino]-5-[3-fluoro-4-nitro-5-((R)-2,2,2-trifluoro-1-methoxymethyl-ethoxy)-benzyl]-tetrahydro-thiopyran-4-ol as a yellow resin: LCMS Rt$_{H3}$=3.00 min; ESIMS [M+H]$^+$=589; $^1$H NMR (400 MHz, DMSO-d$_6$): δ 7.33-7.23 (m, 3H), 7.12 (d, 1H), 6.87 (d, 1H), 6.80 (d, 1H), 4.78-4.69 (m, 1H), 3.92-3.80 (m, 2H), 3.71 (m, 1H), 3.40 (s, 3H), 3.25 (m, 1H), 2.87-2.50 (m, 4H), 2.32-2.11 (m, 4H), 1.38 (d, 3H), 1.30 (s, 9H) and the more polar (3R,4S,5S)-3-[(R)-1-(3-tert-butyl-phenyl)-ethylamino]-5-[3-fluoro-4-nitro-5-((R)-2,2,2-trifluoro-1-methoxymethyl-ethoxy)-benzyl]-tetrahydro-thiopyran-4-ol as a yellow resin: LCMS Rt$_{H3}$=3.02 min; ESIMS [M+H]$^+$=589; $^1$H NMR (400 MHz, DMSO-d$_6$): δ 7.32-7.26 (m, 3H), 7.11 (d, 1H), 6.81 (d, 1H), 6.75 (d, 1H), 4.72 (m, 1H), 4.08-3.95 (m, 2H), 3.82 (m, 1H), 3.71 (t, 1H), 3.38 (s, 3H), 3.16 (m, 1H), 2.77 (q, 1H), 2.52-2.44 (m, 2H), 2.31-2.20 (m, 3H), 1.90 (m, 1H), 1.36 (d, 3H), 1.33 (s, 9H).

b) (1R,3S,4S,5R)-3-[4-Amino-3-fluoro-5-((R)-2,2,2-trifluoro-1-methoxy-methyl-ethoxy)-benzyl]-5-[(R)-1-(3-tert-butyl-phenyl)-ethylamino]-1-oxo-tetrahydro-thio-pyran-4-ol A solution of (3R,4S,5S)-3-[(R)-1-(3-tert-butyl-phenyl)-ethylamino]-5-[3-fluoro-4-nitro-5-((R)-2,2,2-trifluoro-1-methoxymethyl-ethoxy)-benzyl]-tetrahydro-thiopyran-4-ol (0.249 g, 0.423 mmol) in THF (2 mL) and AcOH (1 mL) was treated with 0.22 mL 30% H$_2$O$_2$ and stirred for 18 h at 25° C. The mixture was diluted with EtOAc and washed with aq. Na$_2$S$_2$O$_3$, and brine. The organic layer was dried over Na$_2$SO$_4$ and evaporated to give (3R,4S,5S)-3-[(R)-1-(3-tert-butyl-phenyl)-ethylamino]-5-[3-fluoro-4-nitro-5-((R)-2,2,2-trifluoro-1-methoxymethyl-ethoxy)-benzyl]-1-oxo-hexahydro-1lambda*4*-thiopyran-4-ol as a mixture of sulfoxide diastereomers (HPLC Rt$_{H1}$=2.30, 2.39 min; ESIMS [M+H]$^+$=605), pure enough for further transformation. This product was dissolved in THF-MeOH 4:1 (5 mL) and stirred in the presence of 10% Pd—C (0.1 g) under an atmosphere of hydrogen at 45° C. for 1.5 h. The mixture was filtered over Celite, evaporated and dissolved in 5 mL 3N HCl in MeOH. After 3 d the reaction mixture was concentrated and taken up in 10% aq. Na$_2$CO$_3$ solution and extracted with EtOAc. The organic phase was washed with brine, dried over Na$_2$SO$_4$, filtered and evaporated. The title compound was obtained after purification by column chromatography on silica gel (EtOAc/5% MeOH) 70-0% hexane as a colorless foam: HPLC Rt$_{H1}$=2.535 min; ESIMS [M+H]$^+$=575; [α]$_D$=−9.8° (c=0.4, CH$_2$Cl$_2$); $^1$H NMR (600 MHz, DMSO-d$_6$): δ 7.37 (s, 1H), 7.23-7.20 (m, 2H), 7.13 (m, 1H), 6.69 (s, 1H), 6.61 (d, 1H), 5.10 (m, 1H), 4.82 (s, OH), 4.59-4.55 (NH$_2$), 3.80 (m, 1H), 3.70 (m, 2H), 3.30 (s, 3H), 3.23 (d, 1H), 3.02 (m, 1H), 2.92 (m, 1H), 2.80 (m, 1H), 2.62 (m, 1H), 2.39 (m, 1H), 2.25-2.18 (m, 3H), 1.25 (s, 9H), 1.20 (d, 3H).

Example 52

(1R,3S,4S,5R)-3-[4-Amino-3-fluoro-5-((S)-2,2,2-trifluoro-1-methyl-ethoxy)-benzyl]-5-[(3,3-dimethyl-1,3-dihydro-isobenzofuran-5-ylmethyl)-amino]-1-oxo-hexa-hydro-1lambda*4*-thiopyran-4-ol a) {(3R,4S,5S)-5-[3-Fluoro-4-nitro-5-((S)-2,2,2-trifluoro-1-methyl-ethoxy)-benzyl]-4-hydroxy-tetrahydro-thiopyran-3-yl}-carbamic acid tert-butyl ester The title compound was prepared in an analogous manner as described for example 24j, starting from [(3R,4S,5S)-5-(3,5-difluoro-4-nitro-benzyl)-4-hydroxy-tetrahydro-thiopyran-3-yl]-carbamic acid tert-butyl ester (0.409 g, 1 mmol), KOH (0.06 g, 1.05 mmol) and (S)-1,1,1-trifluoro-propan-2-ol (0.583 g, 5 mmol) and was obtained as a yellow oil, which was used as such in the next step: TLC (hexane-EtOAc 1:1) Rf=0.37; HPLC Rt$_A$=2.36 min; ESIMS [M+H-isobutylene]$^+$=443.

b) {(1R,3R,4S,5S)-5-[3-Fluoro-4-nitro-5-((S)-2,2,2-trifluoro-1-methyl-ethoxy)-benzyl]-4-hydroxy-1-oxo-tetrahydro-thiopyran-3-yl}-carbamic acid tert-butyl ester The title compound was prepared in an analogous manner as described for example 41a, starting from {(3R,4S,5S)-5-[3-fluoro-4-nitro-5-((S)-2,2,2-trifluoro-1-methyl-ethoxy)-benzyl]-4-hydroxy-tetrahydro-thiopyran-3-yl}-carbamic acid tert-butyl ester and was obtained after chromatographic separation of the diastereoisomers as a yellow foam: TLC (EtOAc-MeOH 19:1) Rf=0.40; HPLC Rt$_A$=1.98 min; ESIMS

[M+NH₄]⁺=532; ¹H NMR (600 MHz, DMSO-d₆): δ 7.23 (s, 1H), 7.11 (d, 1H), 6.84 (d, 1H), 5.48 (m, 1H), 5.13 (s, 1H), 4.01 (m, 1H), 3.12 (m, 1H), 3.08 (dd, 1H), 2.90 (d, 1H), 2.79 (m, 2H), 2.53 (m, 2H), 2.34 (t, 1H), 1.45 (d, 3H), 1.38 (s, 9H).

c) (1R,3R,4S,5S)-3-Amino-5-[3-fluoro-4-nitro-5-((S)-2,2,2-trifluoro-1-methyl-ethoxy)-benzyl]-1-oxo-tetrahydro-thiopyran-4-ol The title compound was prepared in an analogous manner as described for example 1g, starting from {(1R,3R,4S,5S)-5-[3-fluoro-4-nitro-5-((S)-2,2,2-trifluoro-1-methyl-ethoxy)-benzyl]-4-hydroxy-1-oxo-tetrahydro-thiopyran-3-yl}-carbamic acid tert-butyl ester and was obtained as a light yellow foam: TLC (CH₂Cl₂-MeOH-AcOH-H₂O 180:20:2:1) Rf=0.10; HPLC Rt_A=1.50 min; ESIMS [M+H]⁺=415; ¹H NMR (600 MHz, DMSO-d₆): δ 8.09 (s, 3H), 7.29 (s, 1H), 7.14 (d, 1H), 6.02 (s broad, 1H), 5.48 (m, 1H), 3.56 (m, 1H), 3.30 (t, 1H), 3.16 (m, 2H), 2.89 (d, 1H), 2.76 (t, 1H), 2.72 (dd, 1H), 2.5-2.6 (m, 2H), 1.46 (d, 3H).

d) 3,3-Dimethyl-1,3-dihydro-isobenzofuran-5-carbaldehyde

The title compound is prepared in analogous manner as described for example 47a from 6-bromo-1,1-dimethyl-1,3-dihydro-isobenzofuran to yield a light yellow oil: TLC (hexane-EtOAc 1:1) Rf=0.50; HPLC Rt_A=1.43 min; ¹H NMR (400 MHz, CDCl₃): δ10.02 (s, 1H), 7.78 (d, 1H), 7.65 (s, 1H), 7.36 (d, 1H), 5.11 (s, 2H), 1.53 (s, 9H).

e) (1R,3R,4S,5S)-3-[(3,3-Dimethyl-1,3-dihydro-isobenzofuran-5-ylmethyl)-amino]-5-[3-fluoro-4-nitro-5-((S)-2,2,2-trifluoro-1-methyl-ethoxy)-benzyl]-1-oxo-hexahydro-1lambda*4*-thiopyran-4-ol The title compound was prepared in an analogous manner as described for example 1h, starting from (1R,3R,4S,5S)-3-amino-5-[3-fluoro-4-nitro-5-((S)-2,2,2-trifluoro-1-methyl-ethoxy)-benzyl]-1-oxo-tetrahydro-thiopyran-4-ol (0.075 g, 0.19 mmol), 3,3-dimethyl-1,3-dihydro-isobenzofuran-5-carbaldehyde (0.036 g, 0.203 mmol), NaOAc (0.032 g, 0.38 mmol) and NaBH₃CN (0.013 g, 0.19 mmol) and was obtained as a light yellow foam after chromatographic purification on silica gel: TLC (EtOAc-MeOH 19:1) Rf=0.20; HPLC Rt_A=1.78 min; ESIMS [M+H]⁺=575; ¹H NMR (400 MHz, CDCl₃): δ 7.19 (m, 2H), 7.04 (s, 1H), 6.84 (s, 1H), 6.78 (d, 1H), 5.04 (s, 2H), 4.76 (m, 1H), 4.25 (s broad, 1H), 3.94 (d, 1H), 3.76 (d, 1H), 3.53 (ddd, 1H), 3.37 (ddd, 1H), 2.8-3.15 (m, 5H), 2.14 (m, 2H), 1.52 (d, 3H), 1.48 (s, 6H).

f) (1R,3S,4S,5R)-3-[4-Amino-3-fluoro-5-((R)-2,2,2-trifluoro-1-methoxymethyl-ethoxy)-benzyl]-5-[(3,3-dimethyl-1,3-dihydro-isobenzofuran-5-ylmethyl)amino]-1-oxo-tetrahydro-thiopyran-4-ol dihydrochloride The title compound was prepared in an analogous manner as described for example 1j, starting from (1R,3R,4S,5S)-3-[(3,3-dimethyl-1,3-dihydro-isobenzofuran-5-ylmethyl)-amino]-5-[3-fluoro-4-nitro-5-((R)-2,2,2-trifluoro-1-methoxymethyl-ethoxy)-benzyl]-1-oxo-tetrahydro-thiopyran-4-ol to provide the title compound as a white foam: TLC (EtOAc-MeOH 9:1) Rf=0.29; HPLC Rt_A=1.50 min; ESIMS [M+H]⁺=545; ¹H NMR (400 MHz, CDCl₃): δ 7.18 (m, 2H), 7.05 (s, 1H), 6.59 (d, 1H), 6.55 (s, 1H), 5.05 (s, 2H), 4.62 (m, 1H), 4.06 (s broad, 1H), 3.91 (d, 1H), 3.75 (d, 1H), 3.73 (s, 1H), 3.51 (ddd, 1H), 3.35 (ddd, 1H), 3.09 (t, 1H), 3.00 (dd, 1H), 2.92 (ddd, 1H), 2.78 (m, 1H), 2.71 (dd, 1H), 2.08 (m, 1H), 1.52 (d, 3H), 1.49 (s, 6H).

Example 53

(1R,3S,4S,5R)-3-[4-Amino-3-fluoro-5-((R)-2,2,2-trifluoro-1-methoxymethyl-ethoxy)-benzyl]-1-oxo-5-(3-trifluoromethoxy-benzylamino)-tetra-hydro-thiopyran-4-ol The title compound can be prepared in an analogous manner as described for example 41 steps c) and d) from (1R,3R,4S,5S)-3-amino-5-[3-fluoro-4-nitro-5-((R)-2,2,2-trifluoro-1-methoxymethyl-ethoxy)-benzyl]-1-oxo-tetrahydro-thiopyran-4-ol hydrochloride and 3-trifluoro-methoxy-benzaldehyde to afford the title compound as a pale yellow foam: TLC (CH₂Cl₂-MeOH 9:1) Rf=0.46; ESIMS [M+H]⁺=589; ¹H NMR (400 MHz, DMSO-d₆): δ 7.45 (t, 1H), 7.38 (d, 1H), 7.37 (s, 1H), 7.21 (d, 1H), 6.73 (s, 1H), 6.65 (d, 1H), 5.12-5.06 (m, 1H), 5.03 (d, 1H), 4.59 (s, 2H), 3.85 (d, 1H), 3.75-3.71 (m, 3H), 3.32 (s, 3H), 3.18-3.07 (m, 3H), 3.00 (dd, 1H), 2.71 (dd, 1H), 2.46-2.28 (m, 4H).

Examples 54 to 63

The compounds listed in Table 5 were prepared by procedures analogous to those used in examples 1h) and 41d).

TABLE 5

| Example | R₁ | R₂ | Chromatography Method | Chromatography Rt [min] | ESIMS [M + H]⁺ |
|---|---|---|---|---|---|
| 54 | (methoxymethyl-trifluoroethoxy group) | (benzylamino with C(CH₃)₂CH₂OH) | F | 1.48 | 577 |

TABLE 5-continued

| Example | R₁ | R₂ | Chromatography Method | Chromatography Rt [min] | ESIMS [M + H]⁺ |
|---|---|---|---|---|---|
| 55 | methoxy-trifluoro-methyl-propoxy group | HN-CH₂-(3-isopropylphenyl) | F | 1.75 | 547 |
| 56 | methoxy-trifluoro-methyl-propoxy group | HN-CH₂-(3-(2-hydroxypropan-2-yl)phenyl) | E | 0.97 | 563 |
| 57 | methoxy-trifluoro-methyl-propoxy group | HN-CH₂-(2,2-dimethyl-2,3-dihydrobenzofuran-5-yl) | F | 1.64 | 575 |
| 58 | methoxy-trifluoro-methyl-propoxy group | HN-CH₂-(4-tert-butylpyridin-2-yl) | G3 | 1.58 | 562 |
| 59 | methoxy-trifluoro-methyl-propoxy group | HN-CH₂-(3-methoxyphenyl) | G3 | 1.41 | 535 |
| 60 | methoxy-trifluoro-methyl-propoxy group | HN-CH₂-(3-ethoxyphenyl) | G3 | 1.55 | 548 |

TABLE 5-continued

[Structure: core scaffold with H2N, R1, F on benzene ring connected via CH2 to tetrahydrothiopyran-S-oxide bearing OH and R2 substituents]

| Example | R1 | R2 | Chromatography Method | Chromatography Rt [min] | ESIMS [M + H]+ |
|---|---|---|---|---|---|
| 61 | (R)-OCH(CF3)CH2OCH3 | 3-isopropoxybenzylamino (HN-CH2-C6H4-O-iPr) | G3 | 1.65 | 563 |
| 62 | (R)-OCH(CF3)CH2OCH3 | 3-(difluoromethoxy)benzylamino | G3 | 1.55 | 571 |
| 63 | OCH2CF2F (2,2-difluoroethoxy) | 3-(trimethylsilyl)benzylamino | G1 | 1.11 | 533 |

Example 64

(1R,3S,5R)-3-[4-Amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-one trifluoroacetate a) (3-tert-Butyl-benzyl)-{(1R,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester A solution of (1R,3R,4S,5S)-3-(3-tert-butyl-benzylamino)-5-[3-fluoro-4-nitro-5-((R)-2,2,2-trifluoro-1-methoxymethyl-ethoxy)-benzyl]-1-oxo-tetrahydro-thiopyran-4-ol (500 mg, 0.847 mmol, example 41c), Boc-anhydride (296 mg, 1.354 mmol) and DIPEA (328 mg, 2.54 mmol) in ACN (9 mL) was stirred at room temperature overnight. The reaction mixture was diluted with EtOAc, washed with 5% aq. NaHSO4 solution, sat. NaHCO3 solution and brine. The organic phase was dried over Na2SO4, filtered and evaporated. Chromatography over silica (40 g, toluene-EtOAc 1:1) afforded the title compound: TLC (cyclohexane: EtOAc 1:2) Rf=0.43; Rt$_E$=1.19 min; ESIMS [M+H]+=661; $^1$H NMR (400 MHz, DMSO-d$_6$ at 80° C.): δ 7.55 (s, 1H), 7.45 (d, 1H), 7.39-7.28 (m, 2H), 6.75 (s, 1H), 6.69 (d, 1H), 4.92 (m, 1H), 4.63 (s, 2H), 4.32-4.22 (m, 2H), 3.84-3.70 (m, 3H), 3.61 (t, 1H), 3.45 (d, 1H), 3.35 (s, 3H), 3.12 (d, 1H), 2.91-2.80 (m, 2H), 2.56 (m, 1H), 1.68 (s, 9H), 1.32 (s, 9H).

b) (3-tert-Butyl-benzyl)-{(1R,3R,5S)-5-[3-fluoro-4-nitro-5-((R)-2,2,2-trifluoro-1-methoxy-methyl-ethoxy)-benzyl]-1,4-dioxo-tetrahydro-thiopyran-3-yl}-carbamic acid tert-butyl ester To a solution of oxalyl chloride (110 mg, 0.869 mmol) in CH2Cl2 (4 mL) was added dropwise at −78° C. DMSO (271 mg, 3.47 mmol) dissolved in CH2Cl2 (2 mL). After 20 min at −78° C. (3-tert-buty 1-benzyl)-{(1R,3R,4S,5S)-5-[3-fluoro-4-nitro-5-((R)-2,2,2-trifluoro-1-methoxymethyl-ethoxy)-benzyl]-4-hydroxy-1-oxo-tetrahydro-thiopyran-3-yl}-carbamic acid tert-butyl ester (150 mg, 0.217 mmol) was added slowly in CH2Cl2 (4 mL) and stirring was continued for 1 h. NEt3 (175 mg, 1.74 mmol) was added in CH2Cl2 (2 mL) and the solution was warmed to to 0° C. 5% aq. NH4Cl solution (3 mL) was added for quenching and the solution was extracted with EtOAc, washed with 5% aq. citric acid, sat. NaHCO3 solution and brine. The organic phase was dried over Na2SO4, filtered and evaporated. Chromatography over silica gel (cyclohexane-EtOAc 2:3) afforded the title compound as a white foam: TLC (cyclohexane: EtOAc 1:2) Rf=0.38; Rt$_E$=1.24 min; ESIMS [M+H-isobutylene]+=633; [M−H]−=687.

c) {(1R,3R,5S)-5-[4-Amino-3-fluoro-5-((R)-2,2,2-trifluoro-1-methoxymethyl-ethoxy)-benzyl]-1,4-dioxo-tetrahydro-thiopyran-3-yl}-(3-tert-butyl-benzyl)-carbamic acid tert-butyl ester The title compound was prepared in an analogous manner as described for example 1j), starting from (3-tert-butyl-benzyl)-{(1R,3R,5S)-5-[3-fluoro-4-nitro-5-((R)-2,2,2-trifluoro-1-methoxymethyl-ethoxy)-benzyl]-1,4-dioxo-tetrahydro-thiopyran-3-yl}-carbamic acid tert-butyl ester to provide the title compound after HPLC purification (Waters Sunfire C18, 5 µm, 30×100 mm, 20-40% CAN in water+0.1% TFA gradient, 16 min): LCMS $Rt_{H1}$=1.48 min; ESMS $[M+H]^+$=659; ESIMS $[M+H-Boc]^+$=559; $[M-H]^-$=657.

d) (1R,3S,5R)-3-[4-Amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-one trifluoroacetate The title compound was prepared in an analogous manner as described for example 8h) starting from {(1R,3R,5S)-5-[4-amino-3-fluoro-5-((R)-2,2,2-trifluoro-1-methoxymethyl-ethoxy)-benzyl]-1,4-dioxo-tetrahydro-thiopyran-3-yl}-(3-tert-butyl-benzyl)-carbamic acid tert-butyl ester to provide the title compound after HPLC purification. UPLC $Rt_E$=1.05 min; ESMS $[M+H]^+$=559.

Example 65

Biological Activity of Compounds of the Formula I

The compounds of the Examples hereinbefore show the following $IC_{50}$ values in Test 1 described hereinbefore:

| Example | Bace $IC_{50}$ [µM] |
|---|---|
| 1 | 0.045 |
| 2 | 0.078 |
| 3 | 1.138 |
| 4 | 0.326 |
| 5 | 4.700 |
| 6 | 0.302 |
| 7 | 8.400 |
| 8 | 0.042 |
| 9 | 0.052 |
| 10 | 0.048 |
| 11 | 0.074 |
| 12 | 0.020 |
| 13 | 0.028 |
| 14 | 0.022 |
| 15 | 0.050 |
| 16 | 0.034 |
| 17 | 1.763 |
| 18 | 0.038 |
| 19 | 0.026 |
| 20 | 0.151 |
| 21 | 0.008 |
| 22 | 0.046 |
| 23 | 0.175 |
| 24 | 0.122 |
| 25 | 0.025 |
| 26 | 0.007 |
| 27 | 0.003 |
| 28 | 0.007 |
| 29 | 0.005 |
| 30 | 0.006 |
| 31 | 0.022 |
| 32 | 0.002 |
| 33 | 0.002 |
| 34 | 0.032 |
| 35 | 0.003 |
| 36 | 0.004 |
| 37 | 0.297 |
| 38 | 0.003 |
| 39 | 0.071 |
| 40 | 0.247 |
| 41 | 0.004 |
| 42 | 0.080 |
| 43 | 0.010 |
| 44 | 0.027 |
| 45 | 0.019 |
| 46 | 0.021 |
| 47 | 0.010 |
| 48 | 0.026 |
| 49 | 0.015 |
| 50 | 2.400 |
| 51 | 0.010 |
| 52 | 0.117 |
| 53 | 0.212 |
| 54 | 0.018 |
| 55 | 0.013 |
| 56 | 0.200 |
| 57 | 0.226 |
| 58 | 0.013 |
| 59 | 0.384 |
| 60 | 0.475 |
| 61 | 0.080 |
| 62 | 0.334 |
| 63 | 0.118 |
| 64 | 0.004 |

$R_4$ is hydrogen; $(C_{1-8})$alkyl; $(C_{1-8})$alkoxy-$(C_{1-8})$alkyl; $(C_{1-8})$alkylcarbonyloxy-$(C_{1-8})$alkyl; formyl; $(C_{1-8})$alkylcarbonyl; or $(C_{1-8})$alkoxycarbonyl;

$R_5$ is hydrogen; halogen; $(C_{1-8})$alkyl; halogen-$(C_{1-8})$alkyl; halogen-$(C_{1-8})$alkyl substituted by hydroxy; halogen-$(C_{1-8})$alkyl substituted by $(C_{1-8})$alkoxy; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; $(C_{2-8})$alkenyl; $(C_{3-8})$cycloalkyl-$(C_{2-8})$alkenyl; halogen-$(C_{2-8})$alkenyl; $(C_{1-8})$alkoxy; halogen-$(C_{1-8})$alkoxy; halogen-$(C_{1-8})$alkoxy substituted by hydroxy; halogen-$(C_{1-8})$alkoxy substituted by $(C_{1-8})$alkoxy; halogen-$C_{1-8})$alkoxy substituted by $(C_{1-8})$alkoxy-$(C_{1-8})$alkoxy; halogen-$(C_{1-8})$alkoxy substituted by amino; halogen-$(C_{1-8})$alkoxy substituted by N—$(C_{1-8})$alkylamino; halogen-$(C_{1-8})$alkoxy substituted by N,N-di-[$(C_{1-8})$alkyl]amino with two identical or different $(C_{1-8})$alkyl moieties, which two $(C_{1-8})$alkyl moieties, taken together, can complete, together with the nitrogen atom, to which they are attached, a ring with 3 to 7 ring members; $(C_{1-8})$alkoxy-$(C_{1-8})$alkyl; halogen-$(C_{1-8})$alkoxy-$(C_{1-8})$alkyl; $(C_{1-8})$alkoxy-$(C_{1-8})$alkoxy; halogen-$(C_{1-8})$alkoxy-$(C_{1-8})$alkoxy; $(C_{1-8})$alkoxy-$(C_{1-8})$alkoxy-$(C_{1-8})$alkyl; halogen-$(C_{1-8})$alkoxy-$(C_{1-8})$alkoxy-$(C_{1-8})$alkyl; formyl; $(C_{1-8})$alkylcarbonyl; $(C_{3-8})$cycloalkylcarbonyl; $(C_{3-8})$cycloalkyl-$(C_{1-8})$alkylcarbonyl; halogen-$(C_{1-8})$alkylcarbonyl; aminocarbonyl; N—$(C_{1-18}$alkylaminocarbonyl optionally substituted by halogen; N,N-di-[$(C_{1-8})$alkyl]aminocarbonyl with two identical or different $(C_{1-8})$alkyl moieties, which two identical or different $(C_{1-8})$alkyl moieties can be substituted, identically or differently, by halogen; N—$(C_{3-8})$cycloalkylaminocarbonyl; N—[$(C_{3-8})$cycloalkyl-$(C_{1-8})$alkyl]aminocarbonyl; $(C_{1-8})$alkoxycarbonyl; halogen-$(C_{1-8})$alkoxycarbonyl; or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group, which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group is optionally ring-substituted by 1 to 4 substituents independently selected from the group, consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy, and in which $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, non-aromatic heterocyclyl or non-aromatic heterocyclyloxy group 1 or 2 —$CH_2$— ring members are optionally replaced with —C(=O)— ring members;

either $R_6$ is absent; and $R_7$ is absent;

or $R_6$ is oxo; and $R_7$ is absent;

or $R_6$ is oxo; and $R_7$ is oxo; imino; $(C_{1-8})$alkylimino; benzylimino; formylimino; or $(C_{1-8})$alkylcarbonylimino;

either $R_8$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a (C3)cycloalkyl group, which $(C_{3-8})$cycloalkyl group is optionally substituted by 1 to 4 substituents independently selected from the group, consisting of halogen and $(C_{1-8})$alkyl; and $R_9$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$-alkyl; or a $(C_{3-8})$cycloalkyl group, which $(C_{3-8})$cycloalkyl group is optionally substituted by 1 to 4 substituents independently selected from the group, consisting of halogen and $(C_{1-8})$alkyl;

or $R_8$ and $R_9$, taken together, complete, together with the carbon atom, to which they are attached, a $(C_{3-8})$cycloalkylidene moiety, in which $(C_{3-8})$cycloalkylidene moiety 1 of its —$CH_2$— ring members can be replaced with —O—;

$R_{10}$ is an aryl or heteroaryl group, which aryl or heteroaryl group is optionally mono-, di-, tri- or tetra-substituted by substituents independently selected from the group, consisting of (i) the univalent substituents halogen, hydroxy, —Si[$(C_{1-8})$alkyl]$_3$ with 3 identical or 2 or 3 different $(C_{1-8})$alkyl moieties, $(C_{1-8})$alkyl, halogen-$(C_{1-8})$alkyl, hydroxy-$(C_{1-8})$alkyl, hydroxy-$(C_{1-8})$alkyl substituted by halogen, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, which heteroaryl group is optionally substituted by 1 to 4 substituents independently selected from the group, consisting of halogen, $(C_{1-8})$alkyl and halogen-$(C_{1-8})$alkyl, and a $(C_{3-8})$cycloalkyl group, in which $(C_{3-8})$cycloalkyl group 1 of its —$CH_2$— ring members can be replaced with —O—, and which $(C_{3-8})$cycloalkyl group, in which 1 of its —$CH_2$— ring members is optionally replaced with —O—, is optionally substituted by 1 to 4 substituents independently selected from the group, consisting of halogen, $(C_{1-8})$alkyl and halogen-$(C_{1-8})$alkyl, and (ii) the bivalent substituents $(C_{3-16})$alkylene, oxa-$(C_{2-16})$alkylene and $(C_{1-8})$alkylenoxa-$(C_{1-8})$alkylene, any such optional bivalent substituent being attached to two adjacent ring carbon atoms of the aryl or heteroaryl group; and either $R_{11}$ is hydrogen; and $R_{12}$ is hydroxy;

or $R_{11}$ and $R_{12}$ taken together are oxo, in free form or in salt form.

The invention claimed is:

1. A compound of the formula

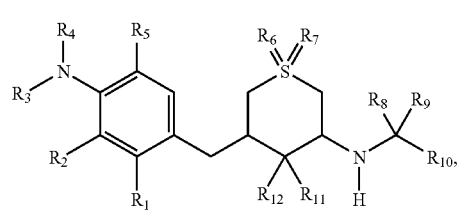

(I)

wherein $R_1$ is hydrogen, halogen, or $(C_{1-8})$alkyl;

$R_2$ is hydrogen, halogen, $(C_{1-8})$alkyl, halogen-$(C_{1-8})$alkyl, $(C_{1-8})$alkoxy, or halogen-$(C_{1-8})$alkoxy;

$R_3$ is hydrogen, and $R_4$ is hydrogen, $(C_{1-8})$alkoxy-$(C_{1-8})$alkyl, $(C_{1-8})$alkylcarbonyloxy-$(C_{1-8})$alkyl, amino-$(C_{1-8})$alkyl, N—$(C_{1-8})$alkylamino-$(C_{1-8})$alkyl, N,N-di-[$(C_{1-8})$alkyl]amino-$(C_{1-8})$alkyl with two identical or different $(C_{1-8})$alkyl moieties in the N,N-di-[$(C_{1-8})$alkyl] amino moiety, N—$(C_{3-8})$cycloalkylamino-$(C_{1-8})$alkyl, formyl, $(C_{1-8})$alkylcarbonyl, $(C_{1-8})$alkoxy-$(C_{1-8})$alkylcarbonyl, amino-$(C_{1-8})$alkylcarbonyl, N—$(C_{1-8})$alkylamino-$(C_{1-8})$alkylcarbonyl, N—$(C_{3-8})$cycloalkylamino-$(C_{1-8})$alkylcarbonyl, or $(C_{1-8})$alkoxycarbonyl, N,N-di-[$(C_{1-8})$alkyl]amino-$(C_{1-8})$alkylcarbonyl with two identical or different $(C_{1-8})$alkyl moieties in said N,N-di-[$(C_{1-8})$alkyl] amino moiety, where said two $(C_{1-8})$alkyl moieties are optionally taken together with the nitrogen atom to which they are attached to form a ring with 3 to 7 ring members;

$R_5$ is halogen, $(C_{1-8})$alkyl, halogen-$(C_{1-8})$alkyl, halogen-$(C_{1-8})$alkyl substituted by hydroxy, halogen-$(C_{1-8})$alkyl substituted by $(C_{1-8})$alkoxy, amino-$(C_{1-8})$alkyl, N—$(C_{1-8})$alkylamino-$(C_{1-8})$alkyl, N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety, $(C_{2-8})$alkenyl, $(C_{3-8})$cycloalkyl-$(C_{2-8})$alkenyl, halogen-$(C_{2-8})$alkenyl, $(C_{1-8})$alkoxy, halogen-$(C_{1-8})$alkoxy, halogen-$(C_{1-8})$alkoxy substituted by hydroxy, halogen-$(C_{1-8})$alkoxy substituted by $(C_{1-8})$alkoxy, halogen-$(C_{1-8})$alkoxy substituted by $(C_{1-8})$alkoxy-$(C_{1-8})$alkoxy, halogen-$(C_{1-8})$alkoxy substituted by amino, halogen-$(C_{1-8})$alkoxy substituted by N—$(C_{1-8})$alkylamino, halogen-$(C_{1-8})$alkoxy substituted by N,N-di-[$(C_{1-8})$alkyl]amino with two identical or different $(C_{1-8})$alkyl moieties, where said two $(C_{1-8})$alkyl moieties are optionally taken together with the nitrogen atom to which they are attached to form a ring with 3 to 7 ring members, $(C_{1-8})$alkoxy-$(C_{1-8})$alkyl, halogen-$(C_{1-8})$alkoxy-$(C_{1-8})$alkyl, $(C_{1-8})$alkoxy-$(C_{1-8})$alkoxy, halogen-$(C_{1-8})$alkoxy-$(C_{1-8})$alkoxy, $(C_{1-8})$alkoxy-$(C_{1-8})$alkoxy-$(C_{1-8})$alkyl, halogen-$(C_{1-8})$alkoxy-$(C_{1-8})$alkoxy-$(C_{1-8})$alkyl, formyl, $(C_{1-8})$alkylcarbonyl, $(C_{3-8})$cycloalkylcarbonyl, $(C_{3-8})$cycloalkyl-$(C_{1-8})$alkylcarbonyl, halogen-$(C_{1-8})$alkylcarbonyl, aminocarbonyl, N—$(C_{1-8})$alkylaminocarbonyl optionally substituted by halogen, N,N-di-[$(C_{1-8})$alkyl]aminocarbonyl with two identical or different $(C_{1-8})$alkyl moieties, where said two identical or different $(C_{1-8})$alkyl moieties are optionally substituted either identically or differently by halogen, N—$(C_{3-8})$cycloalkylaminocarbonyl, N—[$(C_{3-8})$cycloalkyl-$(C_{1-8})$alkyl]aminocarbonyl, $(C_{1-8})$alkoxycarbonyl, halogen-$(C_{1-8})$alkoxycarbonyl, or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group, where said $(C_{3-8})$cycloalkyl, said $(C_{3-8})$cycloalkyl-$(C_{1-8})$alkyl, said $(C_{3-8})$cycloalkyl-$(C_{1-8})$alkoxy, said $(C_{3-8})$cycloalkoxy, said aryl, said aryloxy, said heteroaryl, said heteroaryloxy, said non-aromatic heterocyclyl and said non-aromatic heterocyclyloxy group is optionally ring-substituted by 1 to 4 substituents each independently selected from the group consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy, and where 1 or 2 —$CH_2$— ring members of said $(C_{3-8})$cycloalkyl, said $(C_{3-8})$cycloalkyl-$(C_{1-8})$alkyl, said $(C_{3-8})$cycloalkyl-$(C_{1-8})$alkoxy, said $(C_{3-8})$cycloalkoxy, said non-aromatic heterocyclyl and said non-aromatic heterocyclyloxy group are optionally replaced with —C(=O)— ring members;

either $R_6$ is absent; and $R_7$ is absent;

or $R_6$ is oxo; and $R_7$ is absent;

or $R_6$ is oxo; and $R_7$ is oxo, imino, $(C_{1-8})$alkylimino, benzylimino, formylimino, or $(C_{1-8})$alkylcarbonyl-imino;

either $R_8$ is hydrogen, $(C_{1-8})$alkyl, halogen-$(C_{1-8})$alkyl, hydroxy-$(C_{1-8})$alkyl, $(C_{1-8})$alkoxy-$(C_{1-8})$alkyl, or a $(C_{3-8})$cycloalkyl group, where said $(C_{3-8})$cycloalkyl group is optionally substituted by 1 to 4 substituents each independently selected from the group consisting of halogen and $(C_{1-8})$alkyl, and $R_9$ is hydrogen, $(C_{1-8})$alkyl, halogen-$(C_{1-8})$alkyl, hydroxy-$(C_{1-8})$alkyl, $(C_{1-8})$alkoxy-$(C_{1-8})$alkyl, or a $(C_{3-8})$cycloalkyl group, where said $(C_{3-8})$cycloalkyl group is optionally substituted by 1 to 4 substituents each independently selected from the group consisting of halogen and $(C_{1-8})$alkyl;

$R_{10}$ is an aryl or heteroaryl group, where said aryl and said heteroaryl group are optionally substituted with 1 to 4 substituents each independently selected from the group consisting of (i) an univalent substituent selected from halogen, hydroxy, —Si[$(C_{1-8})$alkyl]$_3$ with 3 identical or 2 or 3 different $(C_{1-8})$alkyl moieties, $(C_{1-8})$alkyl, halogen-$(C_{1-8})$alkyl, hydroxy-$(C_{1-8})$alkyl, hydroxy-$(C_{1-8})$alkyl substituted by halogen, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, where said heteroaryl group is optionally substituted by 1 to 4 substituents each independently selected from the group consisting of halogen, $(C_{1-8})$alkyl, and halogen-$(C_{1-8})$alkyl, or a $(C_{3-8})$cycloalkyl group, where 1 —$CH_2$— ring member of said $(C_{3-8})$cycloalkyl group is optionally replaced with —O— and is optionally substituted by 1 to 4 substituents each independently selected from the group consisting of halogen, $(C_{1-8})$alkyl and halogen-$(C_{1-8})$alkyl, and (ii) a bivalent substituent selected from $(C_{3-16})$alkylene, oxa-$(C_{2-16})$alkylene, or $(C_{1-8})$alkylenoxa-$(C_{1-8})$alkylene, where said bivalent substituent is attached to two adjacent ring carbon atoms of said aryl and said heteroaryl group; and either $R_{11}$ is hydrogen, and $R_{12}$ is hydroxy;

or $R_{11}$ and $R_{12}$ taken together are oxo;

where said compound is in free form or in salt form.

2. The compound according to claim 1, wherein $R_1$ is hydrogen, halogen, or $(C_{1-8})$alkyl;

$R_2$ is hydrogen, halogen, $(C_{1-8})$alkyl, halogen-$(C_{1-8})$alkyl, $(C_{1-8})$alkoxy, or halogen-$(C_{1-8})$alkoxy;

$R_3$ is hydrogen; and $R_4$ is hydrogen, $(C_{1-8})$alkoxy-$(C_{1-8})$alkyl, $(C_{1-8})$alkylcarbonyloxy-$(C_{1-8})$alkyl, amino-$(C_{1-8})$alkyl, N—$(C_{1-8})$alkylamino-$(C_{1-8})$alkyl, N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety, N—$(C_{3-8})$cycloalkylamino-$(C_{1-8})$alkyl, formyl, $(C_{1-8})$alkylcarbonyl, $(C_{1-8})$alkoxy-$(C_{1-8})$alkylcarbonyl, amino-$(C_{1-8})$alkylcarbonyl, N—$(C_{1-8})$alkylamino-$(C_{1-8})$alkylcarbonyl, N—$(C_{3-8}$cycloalkylamino-$(C_{1-8}$alkylcarbonyl, $(C_{1-8})$alkoxycarbonyl, or N,N-di-[$(C_{1-8})$alkyl]amino-$(C_{1-8})$alkylcarbonyl with two identical or different $(C_{1-8})$alkyl moieties in the N,N-di-[$(C_{1-8})$alkyl]amino moiety, where said two $(C_{1-8})$alkyl moieties are optionally taken together with the nitrogen atom to which they are attached to form a ring with 3 to 7 ring members;

$R_5$ is halogen, $(C_{1-8})$alkyl, halogen-$(C_{1-8})$alkyl, halogen-$(C_{1-8})$alkyl substituted by hydroxy, halogen-$(C_{1-8})$alkyl substituted by $(C_{1-8})$alkoxy, amino-$(C_{1-8})$alkyl, N—$(C_{1-8})$alkylamino-$(C_{1-8})$alkyl, N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety, $(C_{2-8})$alkenyl, $(C_{3-8})$cycloalkyl-$(C_{2-8})$alkenyl, halogen-$(C_{2-8})$alkenyl, $(C_{1-8})$alkoxy, halogen-$(C_{1-8})$alkoxy, halogen-$(C_{1-8})$alkoxy substituted by hydroxy, halogen-$(C_{1-8})$alkoxy substituted by $(C_{1-8})$alkoxy, halogen-$(C_{1-8})$alkoxy substituted by $(C_{1-8})$alkoxy-$(C_{1-8})$alkoxy, halogen-$(C_{1-8})$alkoxy substituted by amino, halogen-$(C_{1-8})$alkoxy substituted by N—$(C_{1-8})$alkylamino, halogen-$(C_{1-8})$alkoxy substituted by N,N-di-[$(C_{1-8})$alkyl]amino with two identical or different $(C_{1-8})$alkyl moieties, where said two $(C_{1-8})$alkyl moieties are optionally taken together with the nitrogen atom to which they are attached to form a ring with 3 to 7 ring members, $(C_{1-8})$alkoxy-$(C_{1-8})$alkyl, halogen-$(C_{1-8})$alkoxy-$(C_{1-8})$alkyl, $(C_{1-8})$alkoxy-$(C_{1-8})$alkoxy, halogen-$(C_{1-8})$alkoxy-$(C_{1-8})$alkoxy, $(C_{1-8})$alkoxy-$(C_{1-8})$alkoxy-$(C_{1-8})$alkyl, halogen-$(C_{1-8})$alkoxy-$(C_{1-8})$alkoxy-$(C_{1-8})$alkyl, formyl, $(C_{1-8})$alkylcarbonyl, $(C_{3-8})$cycloalkylcarbonyl, $(C_{3-8})$cycloalkyl-$(C_{1-8})$alkylcarbonyl, halogen-$(C_{1-8})$alkylcarbonyl, aminocarbonyl, N—($C_{1-8}$)alkylaminocarbonyl optionally substituted by halogen, N,N-di-[($C_{1-8}$)alkyl]aminocarbonyl with two identical or different ($C_{1-8}$)alkyl moieties, where said two identical or different ($C_{1-8}$)alkyl moieties are optionally substituted either identically or differently by halogen, N—($C_{3-8}$)cycloalkylaminocarbonyl, N—[($C_{3-8}$)cycloalkyl-($C_{1-8}$)alkyl]aminocarbonyl, ($C_{1-8}$)alkoxycarbonyl, halogen-($C_{1-8}$)alkoxycarbonyl, or a ($C_{3-8}$)cycloalkyl, ($C_{3-8}$)cycloalkyl-($C_{1-8}$)alkyl, ($C_{3-8}$)cycloalkyl-($C_{1-8}$)alkoxy, ($C_{3-8}$)cycloalkoxy, aryl, aryloxy, heteroaryl, heteroaryloxy, non-aromatic heterocyclyl or non-aromatic heterocyclyloxy group, where said ($C_{3-8}$)cycloalkyl, said ($C_{3-8}$)cycloalkyl-($C_{1-8}$)alkyl, said ($C_{3-8}$)cycloalkyl-($C_{1-8}$)alkoxy, said ($C_{3-8}$)cycloalkoxy, said aryl, said aryloxy, said heteroaryl, said heteroaryloxy, said non-aromatic heterocyclyl and said non-aromatic heterocyclyloxy group are optionally ring-substituted by 1 to 4 substituents each independently selected from the group consisting of halogen, ($C_{1-8}$)alkyl, halogen-($C_{1-8}$)alkyl, ($C_{1-8}$)alkoxy-($C_{1-8}$)alkyl, halogen-($C_{1-8}$)alkoxy-($C_{1-8}$)alkyl, ($C_{3-8}$)cycloalkyl, ($C_{1-8}$)alkoxy and halogen-($C_{1-8}$)alkoxy, and where 1 or 2 —$CH_2$— ring members of said ($C_{3-8}$)cycloalkyl, said ($C_{3-8}$)cycloalkyl-($C_{1-8}$)alkyl, said ($C_{3-8}$)cycloalkyl-($C_{1-8}$)alkoxy, said ($C_{3-8}$)cycloalkoxy, said non-aromatic heterocyclyl and said non-aromatic heterocyclyloxy group are optionally replaced with —C(=O)— ring members, $R_6$ is absent, and
$R_7$ is absent;
or
$R_6$ is oxo, and
$R_7$ is absent;
or
$R_6$ is oxo, and
$R_7$ is oxo, imino, ($C_{1-8}$)alkylimino, benzylimino, formylimino, or ($C_{1-8}$)alkylcarbonyl-imino;
either
$R_8$ is hydrogen, ($C_{1-8}$)alkyl, halogen-($C_{1-8}$)alkyl, hydroxy-($C_{1-8}$)alkyl, ($C_{1-8}$)alkoxy-($C_{1-8}$)alkyl, or a ($C_{3-8}$)cycloalkyl group, where said ($C_{3-8}$)cycloalkyl group is optionally substituted by 1 to 4 substituents each independently selected from the group consisting of halogen and ($C_{1-8}$)alkyl, and
$R_9$ is hydrogen, ($C_{1-8}$)alkyl, halogen-($C_{1-8}$)alkyl, hydroxy-($C_{1-8}$)alkyl, ($C_{1-8}$)alkoxy-($C_{1-8}$)alkyl, or a ($C_{3-8}$)cycloalkyl group, where said ($C_{3-8}$)cycloalkyl group is optionally substituted by 1 to 4 substituents each independently selected from the group consisting of halogen and ($C_{1-8}$)alkyl;
$R_{10}$ is an aryl or heteroaryl group, where said aryl and said heteroaryl group are optionally substituted with 1 to 4 substituents each independently selected from the group consisting of (i) an univalent substituent selected from halogen, hydroxy, —Si[($C_{1-8}$)alkyl]$_3$ with 3 identical or 2 or 3 different ($C_{1-8}$)alkyl moieties, ($C_{1-8}$)alkyl, halogen-($C_{1-8}$)alkyl, hydroxy-($C_{1-8}$)alkyl, hydroxy-($C_{1-8}$)alkyl substituted by halogen, ($C_{1-8}$)alkoxy-($C_{1-8}$)alkyl, halogen-($C_{1-8}$)alkoxy-($C_{1-8}$)alkyl, cyano-($C_{1-8}$)alkyl, ($C_{1-8}$)alkoxy, halogen-($C_{1-8}$)alkoxy, a heteroaryl group, where said heteroaryl group is optionally substituted by 1 to 4 substituents each independently selected from the group consisting of halogen, ($C_{1-8}$)alkyl and halogen-($C_{1-8}$)alkyl, or a ($C_{3-8}$)cycloalkyl group, where 1 —$CH_2$— ring member of said ($C_{3-8}$)cycloalkyl group is optionally replaced with —O— and is optionally substituted by 1 to 4 substituents each independently selected from the group consisting of halogen, ($C_{1-8}$)alkyl and halogen-($C_{1-8}$)alkyl, and (ii) a bivalent substituent selected from ($C_{3-16}$)alkylene, oxa-($C_{2-16}$)alkylene and ($C_{1-8}$)alkylenoxa-($C_{1-8}$)alkylene, where said bivalent substituent is attached to two adjacent ring carbon atoms of said aryl or said heteroaryl group;

$R_{11}$ is hydrogen; and
$R_{12}$ is hydroxy;
where said compound is in free form or in salt form.

3. The compound according to claim 1, wherein
$R_1$ is hydrogen, halogen, or ($C_{1-8}$)alkyl;
$R_2$ is hydrogen, halogen, ($C_{1-8}$)alkyl, halogen-($C_{1-8}$)alkyl, ($C_{1-8}$)alkoxy, or halogen-($C_{1-8}$)alkoxy;
$R_3$ is hydrogen; and
$R_4$ is hydrogen, ($C_{1-8}$)alkoxy-($C_{1-8}$)alkyl, ($C_{1-8}$)alkylcarbonyloxy-($C_{1-8}$)alkyl, amino-($C_{1-8}$)alkyl, N—($C_{1-8}$)alkylamino-($C_{1-8}$)alkyl, N,N-di-[($C_{1-8}$)alkyl]amino-($C_{1-8}$)alkyl with two identical or different ($C_{1-8}$)alkyl moieties in the N,N-di-[($C_{1-8}$)alkyl]amino moiety, N—($C_{3-8}$)cycloalkylamino-($C_{1-8}$)alkyl, formyl, ($C_{1-8}$)alkylcarbonyl, ($C_{1-8}$)alkoxy-($C_{1-8}$)alkylcarbonyl, amino-($C_{1-8}$)alkylcarbonyl, N—($C_{1-8}$)alkylamino-($C_{1-8}$)alkylcarbonyl, N,N-di-[($C_{1-8}$)alkyl]amino-($C_{1-8}$)alkylcarbonyl with two identical or different ($C_{1-8}$)alkyl moieties in the N,N-di-[($C_{1-8}$)alkyl]amino moiety, where said two ($C_{1-8}$)alkyl moieties are optionally taken together with the nitrogen atom to which they are attached to form a ring with 3 to 7 ring members, N—($C_{3-8}$)cycloalkylamino-($C_{1-8}$)alkylcarbonyl, or ($C_{1-8}$)alkoxycarbonyl;
$R_5$ is halogen, ($C_{1-8}$)alkyl, halogen-($C_{1-8}$)alkyl, halogen-($C_{1-8}$)alkyl substituted by hydroxy, halogen-($C_{1-8}$)alkyl substituted by ($C_{1-8}$)alkoxy, amino-($C_{1-8}$)alkyl, N—($C_{1-8}$)alkylamino-($C_{1-8}$)alkyl, N,N-di-[($C_{1-8}$)alkyl]amino-($C_{1-8}$)alkyl with two identical or different ($C_{1-8}$)alkyl moieties in the N,N-di-[($C_{1-8}$)alkyl]amino moiety, ($C_{2-8}$)alkenyl, ($C_{3-8}$)cycloalkyl-($C_{2-8}$)alkenyl, halogen-($C_{2-8}$)alkenyl, ($C_{1-8}$)alkoxy, halogen-($C_{1-8}$)alkoxy, halogen-($C_{1-8}$)alkoxy substituted by hydroxy, halogen-($C_{1-8}$)alkoxy substituted by ($C_{1-8}$)alkoxy, halogen-($C_{1-8}$)alkoxy substituted by ($C_{1-8}$)alkoxy-($C_{1-8}$)alkoxy, halogen-($C_{1-8}$)alkoxy substituted by amino, halogen-($C_{1-8}$)alkoxy substituted by N—($C_{1-8}$)alkylamino, halogen-($C_{1-8}$)alkoxy substituted by N,N-di-[($C_{1-8}$)alkyl]amino with two identical or different ($C_{1-8}$)alkyl moieties, where said two ($C_{1-8}$)alkyl moieties are optionally taken together with the nitrogen atom to which they are attached to form a ring with 3 to 7 ring members, ($C_{1-8}$)alkoxy-($C_{1-8}$)alkyl, halogen-($C_{1-8}$)alkoxy-($C_{1-8}$)alkyl, ($C_{1-8}$)alkoxy-($C_{1-8}$)alkoxy, halogen-($C_{1-8}$)alkoxy-($C_{1-8}$)alkoxy, ($C_{1-8}$)alkoxy-($C_{1-8}$)alkoxy-($C_{1-8}$)alkyl, halogen-($C_{1-8}$)alkoxy-($C_{1-8}$)alkoxy-($C_{1-8}$)alkyl, formyl, ($C_{1-8}$)alkylcarbonyl, ($C_{3-8}$)cycloalkylcarbonyl, ($C_{3-8}$)cycloalkyl-($C_{1-8}$)alkylcarbonyl, halogen-($C_{1-8}$)alkylcarbonyl, aminocarbonyl, N—($C_{1-8}$)alkylaminocarbonyl optionally substituted by halogen, N,N-di-[($C_{1-8}$)alkyl]aminocarbonyl with two identical or different ($C_{1-8}$)alkyl moieties, where said two identical or different ($C_{1-8}$)alkyl moieties are optionally substituted identically or differently by halogen, N—($C_{3-8}$)cycloalkylaminocarbonyl, N—[($C_{3-8}$)cycloalkyl-($C_{1-8}$)alkyl]aminocarbonyl, ($C_{1-8}$)alkoxycarbonyl, halogen-($C_{1-8}$)alkoxycarbonyl, or a ($C_{3-8}$)cycloalkyl, ($C_{3-8}$)cycloalkyl-($C_{1-8}$)alkyl, ($C_{3-8}$)cycloalkyl-($C_{1-8}$)alkoxy, ($C_{3-8}$)cycloalkoxy, aryl, aryloxy, heteroaryl, heteroaryloxy, non-aromatic heterocyclyl or non-aromatic heterocyclyloxy group, where said $(C_{3-8})$cycloalkyl, said $(C_{3-8})$cycloalkyl-$(C_{1-8})$alkyl, said $(C_{3-8})$cycloalkyl-$(C_{1-8})$alkoxy, said $(C_{3-8})$cycloalkoxy, said aryl, said aryloxy, said heteroaryl, said heteroaryloxy, said non-aromatic heterocyclyl and said non-aromatic heterocyclyloxy group are optionally ring-substituted by 1 to 4 substituents each independently selected from the group consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy and halogen-$(C_{1-8})$alkoxy, and where 1 or 2 —CH$_2$— ring members of said $(C_{3-8})$cycloalkyl, said $(C_{3-8})$cycloalkyl-$(C_{1-8})$alkyl, said $(C_{3-8})$cycloalkyl-$(C_{1-8})$alkoxy, said $(C_{3-8})$cycloalkoxy, said non-aromatic heterocyclyl and said non-aromatic heterocyclyloxy group are optionally replaced with —C(=O)— ring members;

$R_6$ is absent, and
$R_7$ is absent;
or
$R_6$ is oxo, and
$R_7$ is absent;
or
$R_6$ is oxo, and
$R_7$ is oxo, imino, $(C_{1-8})$alkylimino, benzylimino, formylimino, or $(C_{1-8})$alkylcarbonyl-imino;
either
$R_8$ is hydrogen, $(C_{1-8})$alkyl, halogen-$(C_{1-8})$alkyl, hydroxy-$(C_{1-8})$alkyl, $(C_{1-8})$alkoxy-$(C_{1-8})$alkyl, or a $(C_{3-8})$cycloalkyl group, where said $(C_{3-8})$cycloalkyl group is optionally substituted by 1 to 4 substituents each independently selected from the group consisting of halogen and $(C_{1-8})$alkyl, and
$R_9$ is hydrogen, $(C_{1-8})$alkyl, halogen-$(C_{1-8})$alkyl, hydroxy-$(C_{1-8})$alkyl, $(C_{1-8})$alkoxy-$(C_{1-8})$alkyl, or a $(C_{3-8})$cycloalkyl group, where said $(C_{3-8})$cycloalkyl group is optionally substituted by 1 to 4 substituents each independently selected from the group consisting of halogen and $(C_{1-8})$alkyl;
$R_{10}$ is an aryl or heteroaryl group, where said aryl and said heteroaryl group are optionally substituted with 1 to 4 substituents each independently selected from the group consisting of
(i) an univalent substituent selected from halogen, hydroxy, —Si[$(C_{1-8})$alkyl]$_3$ with 3 identical or 2 or 3 different $(C_{1-8})$alkyl moieties, $(C_{1-8})$alkyl, halogen-$(C_{1-8})$alkyl, hydroxy-$(C_{1-8})$alkyl, hydroxy-$(C_{1-8})$alkyl substituted by halogen, $(C_{1-8})$alkoxy-$(C_{1-8})$alkyl, halogen-$(C_{1-8})$alkoxy-$(C_{1-8})$alkyl, cyano-$(C_{1-8})$alkyl, $(C_{1-8})$alkoxy, halogen-$(C_{1-8})$alkoxy, a heteroaryl group, where said heteroaryl group is optionally substituted by 1 to 4 substituents independently selected from the group consisting of halogen, $(C_{1-8})$alkyl, and halogen-$(C_{1-8})$alkyl, or a $(C_{3-8})$cycloalkyl group, where 1 —CH$_2$— ring member of said $(C_{3-8})$cycloalkyl group is optionally replaced with —O— and is optionally substituted by 1 to 4 substituents each independently selected from the group consisting of halogen, $(C_{1-8})$alkyl and halogen-$(C_{1-8})$alkyl, and
(ii) a bivalent substituent selected from $(C_{3-16})$alkylene, oxa-$(C_{2-16})$alkylene or $(C_{1-8})$alkylenoxa-$(C_{1-8})$alkylene, where said bivalent substituent is attached to two adjacent ring carbon atoms of said aryl or said heteroaryl group; and
$R_{11}$ and $R_{12}$ taken together are oxo;
where said compound is in free form or in salt form.

4. The compound according to claim 1, wherein
$R_1$ is hydrogen, halogen, or $(C_{1-8})$alkyl;
$R_2$ is hydrogen, halogen, $(C_{1-8})$alkyl, halogen-$(C_{1-8})$alkyl, $(C_{1-8})$alkoxy, or halogen-$(C_{1-8})$alkoxy;
$R_4$ is hydrogen, $(C_{1-8})$alkyl, $(C_{1-8})$alkoxy-$(C_{1-8})$alkyl, $(C_{1-8})$alkylcarbonyloxy-$(C_{1-8})$alkyl, formyl, $(C_{1-8})$alkylcarbonyl, or $(C_{1-8})$alkoxycarbonyl;
$R_5$ is halogen, $(C_{1-8})$alkyl, halogen-$(C_{1-8})$alkyl, halogen-$(C_{1-8})$alkyl substituted by hydroxy, halogen-$(C_{1-8})$alkyl substituted by $(C_{1-8})$alkoxy, amino-$(C_{1-8})$alkyl, N—$(C_{1-8})$alkylamino-$(C_{1-8})$alkyl, N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety, $(C_{2-8})$alkenyl, $(C_{3-8})$cycloalkyl-$(C_{2-8})$alkenyl, halogen-$(C_{2-8})$alkenyl, $(C_{1-8})$alkoxy, halogen-$(C_{1-8})$alkoxy, halogen-$(C_{1-8})$alkoxy substituted by hydroxy, halogen-$(C_{1-8})$alkoxy substituted by $(C_{1-8})$alkoxy, halogen-$(C_{1-8})$alkoxy substituted by $(C_{1-8})$alkoxy-$(C_{1-8})$alkoxy, halogen-$(C_{1-8})$alkoxy substituted by amino, halogen-$(C_{1-8})$alkoxy substituted by N—$(C_{1-8})$alkylamino, halogen-$(C_{1-8})$alkoxy substituted by N,N-di-[$(C_{1-8})$alkyl]amino with two identical or different $(C_{1-8})$alkyl moieties, where said two $(C_{1-8})$alkyl moieties are optionally taken together with the nitrogen atom to which they are attached to form a ring with 3 to 7 ring members, $(C_{1-8})$alkoxy-$(C_{1-8})$alkyl, halogen-$(C_{1-8})$alkoxy-$(C_{1-8})$alkyl, $(C_{1-8})$alkoxy-$(C_{1-8})$alkoxy, halogen-$(C_{1-8})$alkoxy-$(C_{1-8})$alkoxy, $(C_{1-8})$alkoxy-$(C_{1-8})$alkoxy-$(C_{1-8})$alkyl, halogen-$(C_{1-8})$alkoxy-$(C_{1-8})$alkoxy-$(C_{1-8})$alkyl, formyl, $(C_{1-8})$alkylcarbonyl, $(C_{3-8})$cycloalkylcarbonyl, $(C_{3-8})$cycloalkyl-$(C_{1-8})$alkylcarbonyl, halogen-$(C_{1-8})$alkylcarbonyl, aminocarbonyl, N—$(C_{1-8})$alkylaminocarbonyl optionally substituted by halogen, N,N-di-[$(C_{1-8})$alkyl]aminocarbonyl with two identical or different $(C_{1-8})$alkyl moieties, where said two identical or different $(C_{1-8})$alkyl moieties are optionally substituted either identically or differently by halogen, N—$(C_{3-8})$cycloalkylaminocarbonyl, N—[$(C_{3-8})$cycloalkyl-$(C_{1-8})$alkyl]aminocarbonyl, $(C_{1-8})$alkoxycarbonyl, halogen-$(C_{1-8})$alkoxycarbonyl, or a $(C_{3-8})$cycloalkyl, $(C_{3-8})$cycloalkyl-$(C_{1-8})$alkyl, $(C_{3-8})$cycloalkyl-$(C_{1-8})$alkoxy, $(C_{3-8})$cycloalkoxy, aryl, aryloxy, heteroaryl, heteroaryloxy, non-aromatic heterocyclyl or non-aromatic heterocyclyloxy group, where said $(C_{3-8})$cycloalkyl, said $(C_{3-8})$cycloalkyl-$(C_{1-8})$alkyl, said $(C_{3-8})$cycloalkyl-$(C_{1-8})$alkoxy, said $(C_{3-8})$cycloalkoxy, said aryl, said aryloxy, said heteroaryl, said heteroaryloxy, said non-aromatic heterocyclyl and said non-aromatic heterocyclyloxy group are optionally ring-substituted by 1 to 4 substituents each independently selected from the group consisting of halogen, $(C_{1-8})$alkyl, halogen-$(C_{1-8})$alkyl, $(C_{1-8})$alkoxy-$(C_{1-8})$alkyl, halogen-$(C_{1-8})$alkoxy-$(C_{1-8})$alkyl, $(C_{3-8})$cycloalkyl, $(C_{1-8})$alkoxy, and halogen-$(C_{1-8})$alkoxy, and where 1 or 2 —CH$_2$— ring members of said $(C_{3-8})$cycloalkyl, said $(C_{3-8})$cycloalkyl-$(C_{1-8})$alkyl, said $(C_{3-8})$cycloalkyl-$(C_{1-8})$alkoxy, said $(C_{3-8})$cycloalkoxy, said non-aromatic heterocyclyl and said non-aromatic heterocyclyloxy group are optionally replaced with —C(=O)— ring members;

$R_6$ is absent, and
$R_7$ is absent;
or
$R_6$ is oxo, and
$R_7$ is absent;
or
$R_6$ is oxo, and

87

R₇ is oxo, imino, (C₁₋₈)alkylimino, benzylimino, formylimino, or (C₁₋₈)alkylcarbonyl-imino;
either
R₈ is hydrogen, (C₁₋₈)alkyl, halogen-(C₁₋₈)alkyl, hydroxy-(C₁₋₈)alkyl, (C₁₋₈)alkoxy-(C₁₋₈)alkyl, or a (C₃₋₈)cycloalkyl group, where said (C₃₋₈)cycloalkyl group is optionally substituted by 1 to 4 substituents each independently selected from the group consisting of halogen and (C₁₋₈)alkyl; and
R₉ is hydrogen, (C₁₋₈)alkyl, halogen-(C₁₋₈)alkyl, hydroxy-(C₁₋₈)alkyl, (C₁₋₈)alkoxy-(C₁₋₈)alkyl, or a (C₃₋₈)cycloalkyl group, where said (C₃₋₈)cycloalkyl group is optionally substituted by 1 to 4 substituents each independently selected from the group consisting of halogen and (C₁₋₈)alkyl;
R₁₀ is an aryl or heteroaryl group, where said aryl and said heteroaryl group is optionally substituted with 1 to 4 substituents each independently selected from the group consisting of
(i) an univalent substituent selected from halogen, hydroxy, —Si[(C₁₋₈)alkyl]₃ with 3 identical or 2 or 3 different (C₁₋₈)alkyl moieties, (C₁₋₈)alkyl, halogen-(C₁₋₈)alkyl, hydroxy-(C₁₋₈)alkyl, hydroxy-(C₁₋₈)alkyl substituted by halogen, (C₁₋₈)alkoxy-(C₁₋₈)alkyl, halogen-(C₁₋₈)alkoxy-(C₁₋₈)alkyl, cyano-(C₁₋₈)alkyl, (C₁₋₈)alkoxy, halogen-(C₁₋₈)alkoxy, a heteroaryl group, where said heteroaryl group is optionally substituted by 1 to 4 substituents each independently selected from the group consisting of halogen, (C₁₋₈)alkyl and halogen-(C₁₋₈)alkyl, and a (C₃₋₈)cycloalkyl group, where 1 —CH₂— ring member of said (C₃₋₈)cycloalkyl group is optionally replaced with —O— and is optionally substituted by 1 to 4 substituents each independently selected from the group consisting of (C₁₋₈)alkyl, and halogen-(C₁₋₈)alkyl, and
(ii) a bivalent substituent selected from (C₃₋₁₆)alkylene, oxa-(C₂₋₁₆)alkylene or (C₁₋₈)alkylenoxa-(C₁₋₈)alkylene, where said bivalent substituent is attached to two adjacent ring carbon atoms of said aryl or said heteroaryl group; and
either
R₁₁ is hydrogen, and
R₁₂ is hydroxy;
or
R₁₁ and R₁₂ taken together are oxo,
where said compound is in free form or in salt form.

5. The compound according to claim 1 of the formula I, selected from the group of compounds consisting of

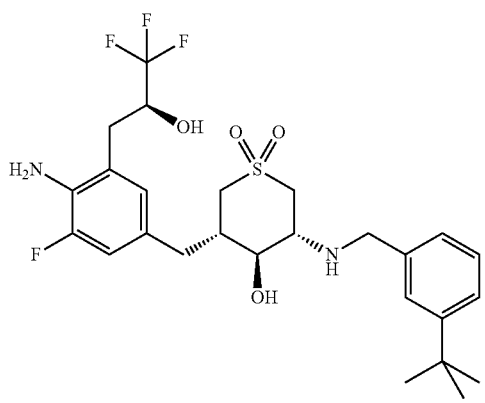

88

(3S*,4S*,5R*)-3-[4-amino-3-fluoro-5-((S)-3,3,3-trifluoro-2-hydroxy-propyl)-benzyl]-5-(3-tert-butyl-benzylamino)-1,1-dioxo-hexahydro-thiopyran-4-ol,

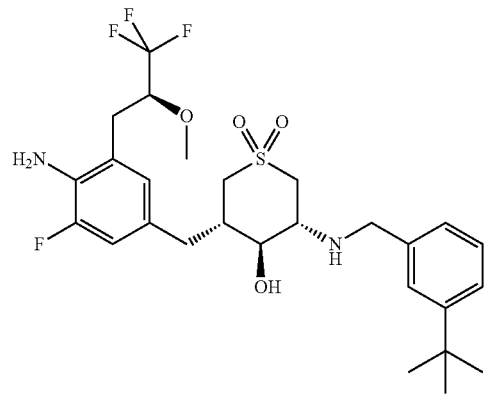

(3S*,4S*,5R*)-3-[4-amino-3-fluoro-5-((S)-3,3,3-trifluoro-2-methoxy-propyl)-benzyl]-5-(3-tert-butyl-benzylamino)-1,1-dioxo-hexahydro-thiopyran-4-ol,

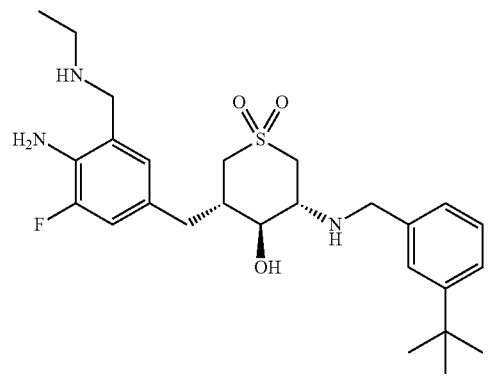

(3S*,4S*,5R*)-3-(4-amino-3-ethylaminomethyl-5-fluoro-benzyl)-5-(3-tert-butyl-benzylamino)-1,1-dioxo-hexahydro-thiopyran-4-ol,

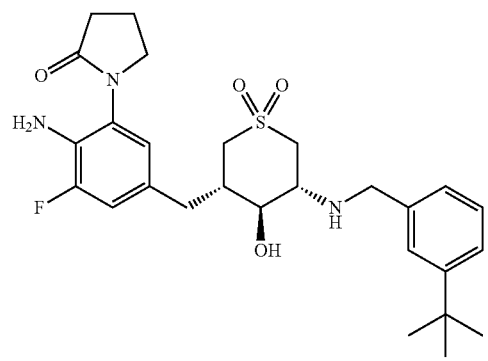

1-{2-amino-5-[(3S*,4S*,5*)-5-(3-tert-butyl-benzy-lamino)-4-hydroxy-1,1-dioxo-hexahydro-thiopyran-3-ylmethyl]-3-fluoro-phenyl}-pyrrolidin-2-one, (3R*,4S*,5S*)-3-(3-tert-butyl-benzylamino)-5 44-(2-dimethylamino-ethylamino)-3-fluoro-benzyl]-1,1-dioxo-hexahydro-thiopyran-4-ol,

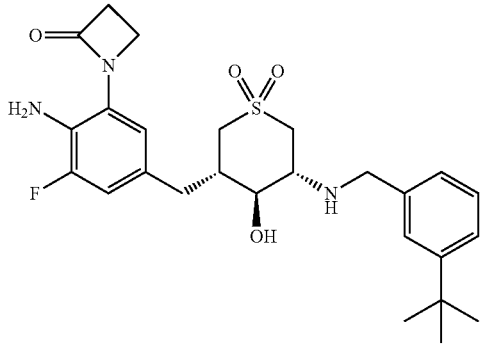

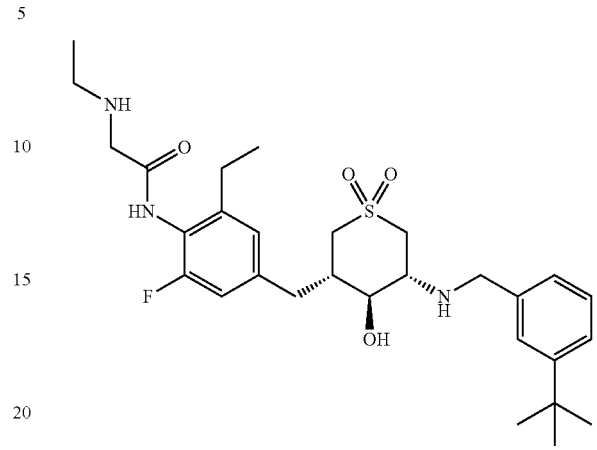

1-{2-amino-5-[(3S*,4S*,5R*)-5-(3-tert-butyl-benzy-lamino)-4-hydroxy-1,1-dioxo-hexahydro-thiopyran-3-ylmethyl]-3-fluoro-phenyl]-azetidin-2-one, N-{4-[(3S,4S,5R)-5-(3-tert-butyl-benzylamino)-4-hy-droxy-1,1-dioxo-hexahydro-thiopyran-3-ylmethyl]-2-ethyl-6-fluoro-phenyl}-2-ethylamino-acetamide,

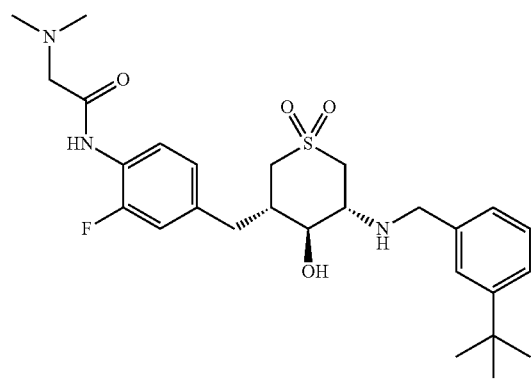

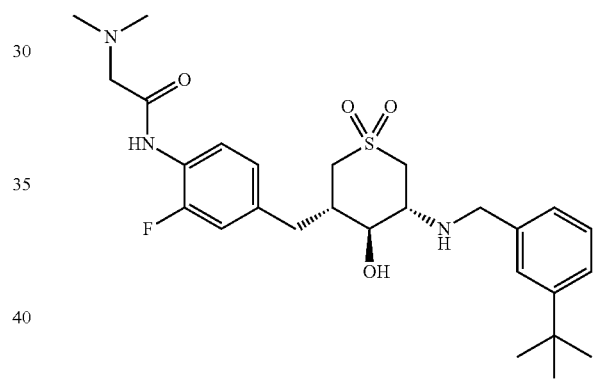

N-{4-[(3S*,4S*,5R*)-5-(3-tert-butyl-benzylamino)-4-hy-droxy-1,1-dioxo-hexahydro-thiopyran-3-ylmethyl]-2-fluoro-phenyl}-2-dimethylamino-acetamide, N-{-4-[(3S,4S,5R)-5-(3-tert-butyl-benzylamino)-4-hy-droxy-1,1-dioxo-hexahydro-thiopyran-3-ylmethyl]-2-ethyl-6-fluoro-phenyl}-2-dimethylamino-acetamide,

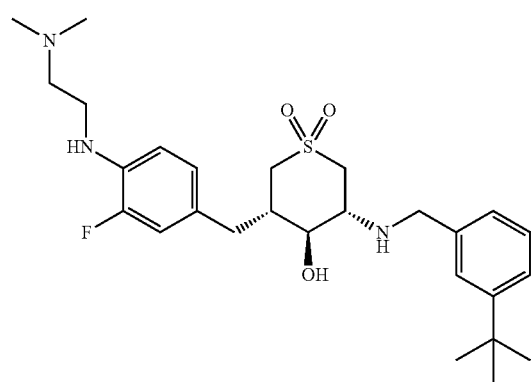

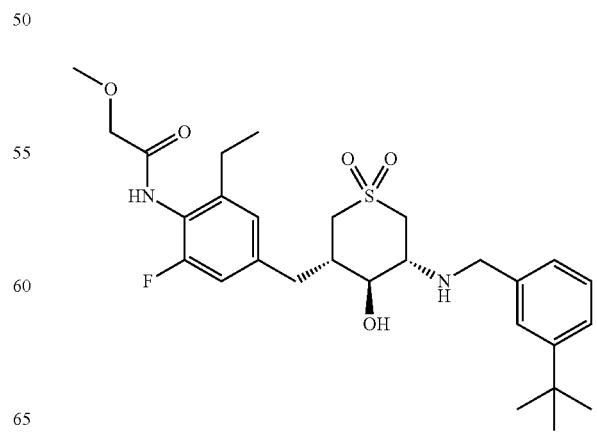

91

N-{4-[(3S,4S,5R)-5-(3-tert-butyl-benzylamino)-4-hydroxy-1,1-dioxo-hexahydro-thiopyran-3-ylmethyl]-2-ethyl-6-fluoro-phenyl]-2-methoxy-acetamide,

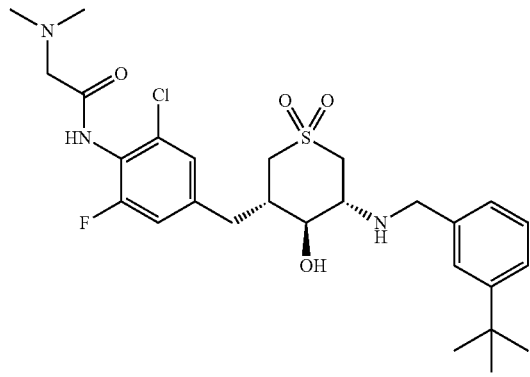

N-{4-[(3S,4S,5R)-5-(3-tert-butyl-benzylamino)-4-hydroxy-1,1-dioxo-hexa-hydro-thiopyran-3-ylmethyl]-2-chloro-6-fluoro-phenyl}-2-dimethylamino-acetamide,

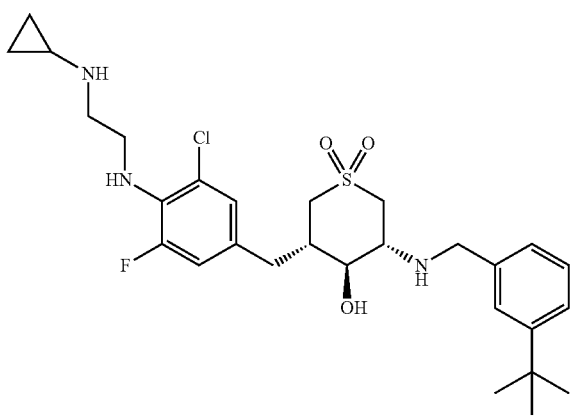

(3R,4S,5S)-3-(3-tert-butyl-benzylamino)-5-[3-chloro-4-(2-cyclopropylamino-ethylamino)-5-fluoro-benzyl]-1,1-dioxo-hexahydro-thiopyran-4-ol,

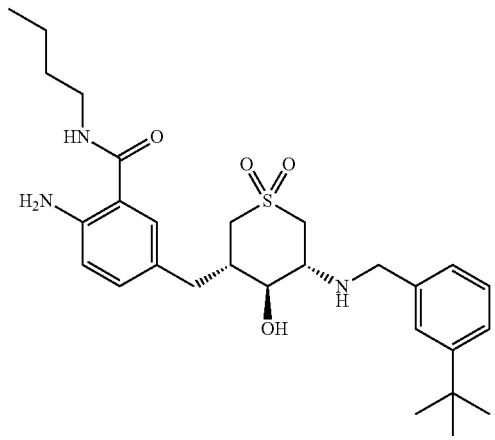

92

2-amino-N-butyl-5-[(3S*,4S*,5R*)-5-(3-tert-butyl-benzylamino)-4-hydroxy-1,1-dioxo-hexahydro-thiopyran-3-ylmethyl]-benzamide,

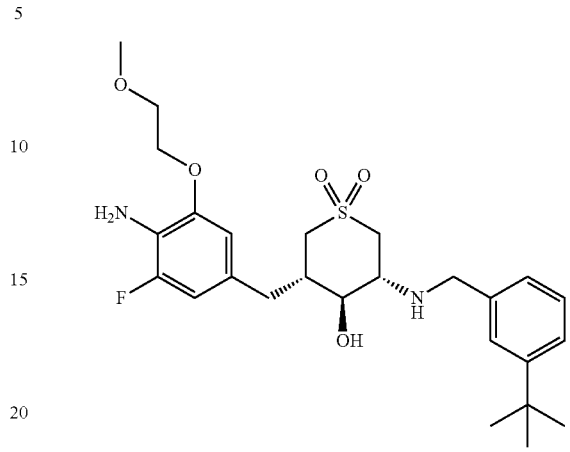

(3S,4S,5R)-3-[4-amino-3-fluoro-5-(2-methoxy-ethoxy)-benzyl]-5-(3-tert-butyl-benzylamino)-1,1-dioxo-hexahydro-thiopyran-4-ol,

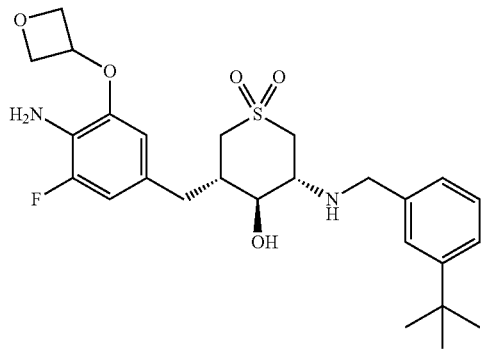

(3S,4S,5R)-3-[4-amino-3-fluoro-5-(oxetan-3-yloxy)-benzyl]-5-(3-tert-butyl-benzylamino)-1,1-dioxo-hexahydro-thiopyran-4-ol,

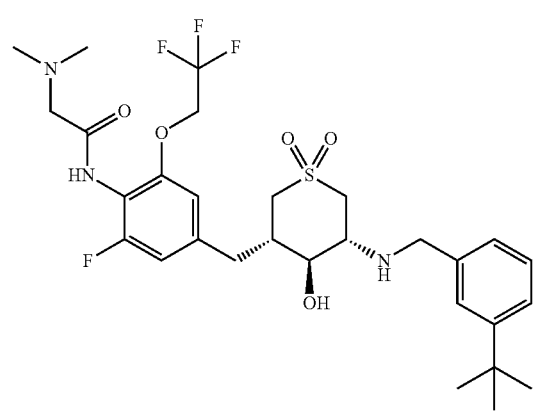

N-[4-[(3S,4S,5R)-5-(3-tert-butyl-benzylamino)-4-hydroxy-1,1-dioxo-hexahydro-thiopyran-3-ylmethyl]-2-fluoro-6-(2,2,2-trifluoro-ethoxy)-phenyl]-2-dimethylamino-acetamide,

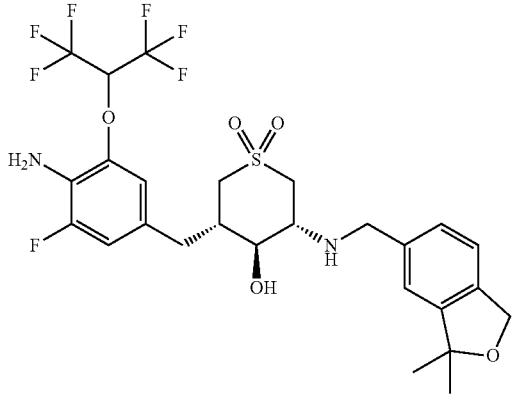

(3S,4S,5R)-3-[4-amino-3-fluoro-5-(2,2,2-trifluoro-1-trifluoromethyl-ethoxy)-benzyl]-5-[(3,3-dimethyl-1,3-dihydro-isobenzofuran-5-ylmethyl)-amino]-1,1-dioxo-hexahydro-thiopyran-4-ol,

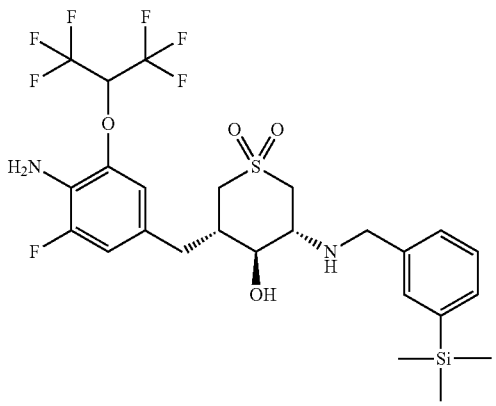

(3S,4S,5R)-3-[4-amino-3-fluoro-5-(2,2,2-trifluoro-1-trifluoromethyl-ethoxy)-benzyl]-1,1-dioxo-5-(3-trimethylsilanyl-benzylamino)-hexahydro-thiopyran-4-ol,

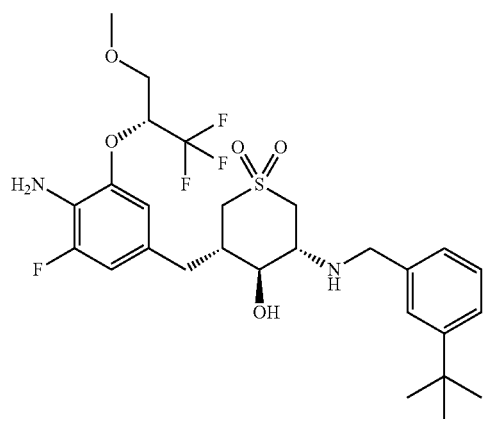

(3S,4S,5R)-3-[4-amino-3-fluoro-5-((R)-2,2,2-trifluoro-1-methoxymethyl-ethoxy)-benzyl]-5-(3-tert-butyl-benzylamino)-1,1-dioxo-hexahydro-thiopyran-4-ol,

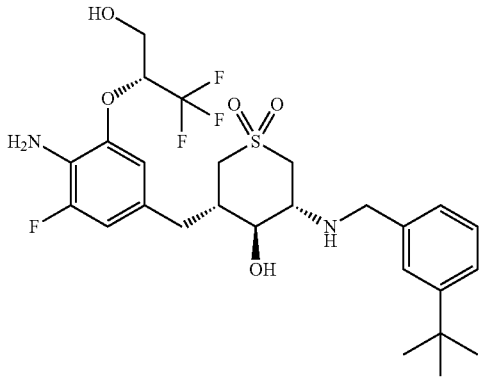

(3S,4S,5R)-3-[4-amino-3-fluoro-5-((R)-2,2,2-trifluoro-1-hydroxymethyl-ethoxy)-benzyl]-5-(3-tert-butyl-benzylamino)-1,1-dioxo-hexahydro-thiopyran-4-ol,

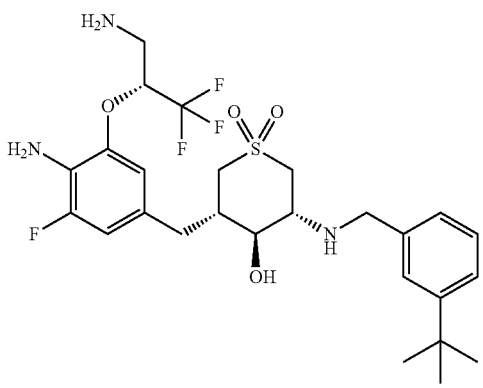

(3S,4S,5R)-3-[4-amino-3-((R)-1-aminomethyl-2,2,2-trifluoro-ethoxy)-5-fluoro-benzyl]-5-(3-tert-butyl-benzylamino)-1,1-dioxo-hexahydro-thiopyran-4-ol,

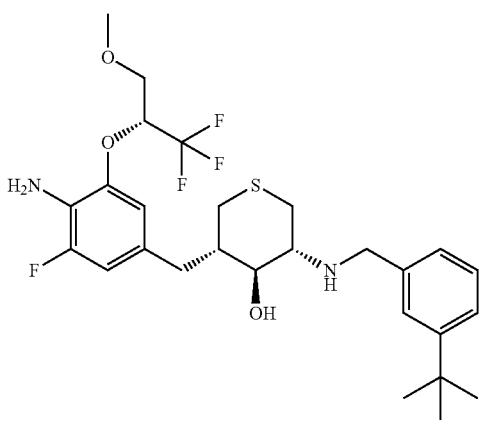

95

(3S,4S,5R)-3-[4-amino-3-fluoro-5-((R)-2,2,2-trifluoro-1-methoxymethyl-ethoxy)-benzyl]-5-(3-tert-butyl-benzylamino)-tetrahydro-thiopyran-4-ol,

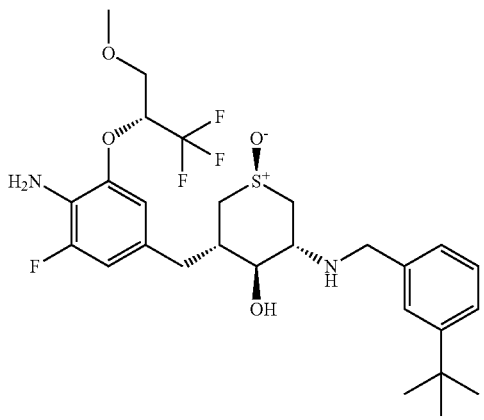

(1R,3S,4S,5R)-3-[4-amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-ol (cis-sulfoxide),

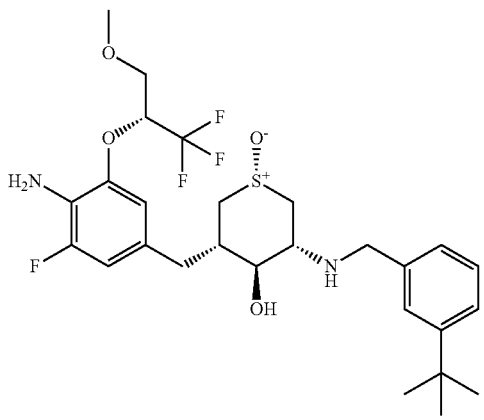

(1S,3S,4S,5R)-3-[4-amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-ol (trans-sulfoxide),

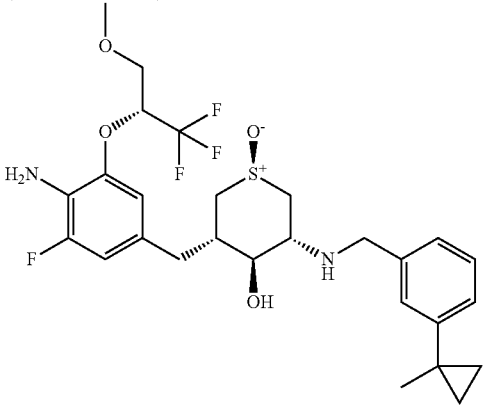

96

(1R,3S,4S,5R)-3-[4-amino-3-fluoro-5-((R)-2,2,2-trifluoro-1-methoxymethyl-ethoxy)-benzyl]-5-[3-(1-methyl-cyclopropyl)-benzylamino]-1-oxo-hexahydro-thiopyran-4-ol (cis-sulfoxide),

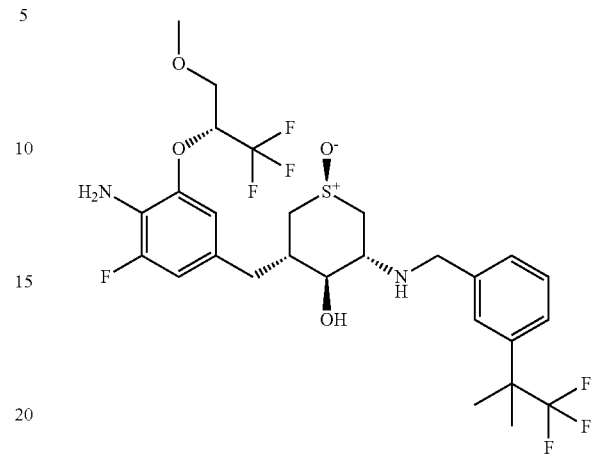

(1R,3S,4S,5R)-3-[4-amino-3-fluoro-5-((R)-2,2,2-trifluoro-1-methoxymethyl-ethoxy)-benzyl]-1-oxo-5-[3-(2,2,2-trifluoro-1,1-dimethyl-ethyl)-benzylamino]-tetrahydro-thiopyran-4-ol (cis-sulfoxide),

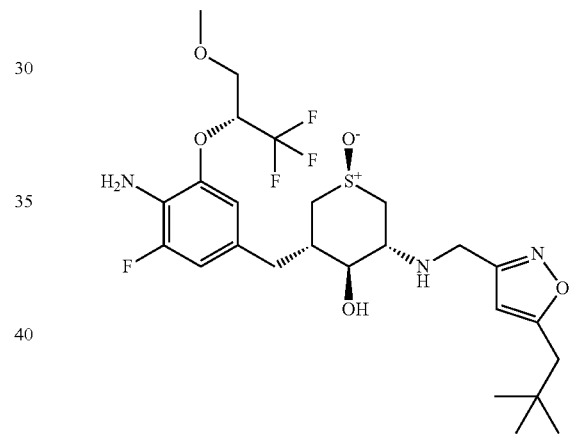

(1R,3S,4S,5R)-3-[4-amino-3-fluoro-5-((R)-2,2,2-trifluoro-1-methoxymethyl-ethoxy)-benzyl]-5-{[5-(2,2-dimethyl-propyl)-isoxazol-3-ylmethyl]-amino}-1-oxo-tetra-hydro-thiopyran-4-ol (cis sulfoxide),

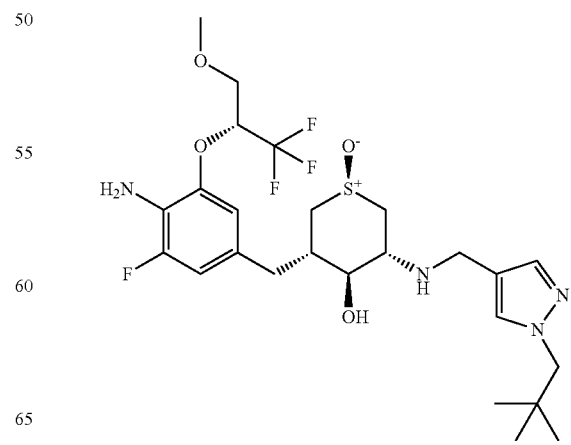

(1R,3S,4S,5R)-3-[4-amino-3-fluoro-5-((R)-2,2,2-trifluoro-1-methoxymethyl-ethoxy)-benzyl]-5-{[1-(2,2-dimethyl-propyl)-1H-pyrazol-4-ylmethyl]-amino}-1-oxo-tetra-hydro-thiopyran-4-ol (cis sulfoxide),

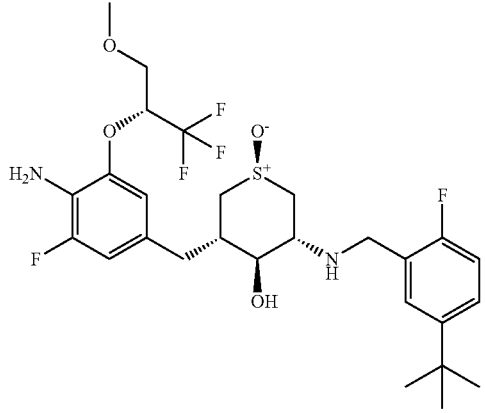

(1R,3S,4S,5R)-3-[4-amino-3-fluoro-5-((R)-2,2,2-trifluoro-1-methoxymethyl-ethoxy)-benzyl]-5-(3-tert-butyl-5-methoxy-benzylamino)-1-oxo-tetrahydro-thiopyran-4-ol (cis sulfoxide),

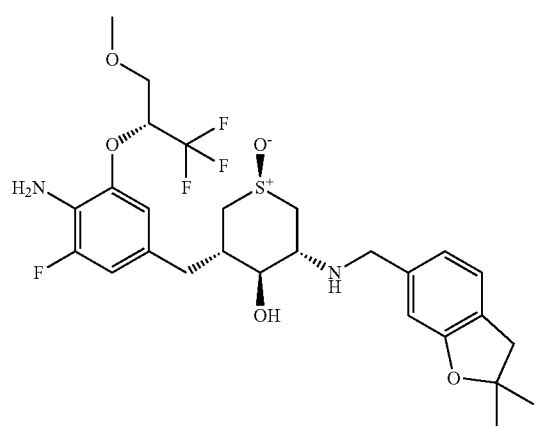

(1R,3S,4S,5R)-3-[4-amino-3-fluoro-5-((R)-2,2,2-trifluoro-1-methoxymethyl-ethoxy)-benzyl]-5-(5-tert-butyl-2-fluoro-benzylamino)-1-oxo-tetrahydro-thiopyran-4-ol (cis sulfoxide),

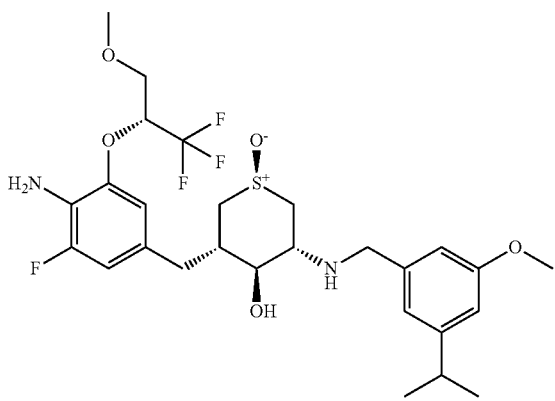

(1R,3S,4S,5R)-3-[4-amino-3-fluoro-5-((R)-2,2,2-trifluoro-1-methoxymethyl-ethoxy)-benzyl]-5-[(2,2-dimethyl-2,3-dihydro-benzofuran-6-ylmethyl)-amino]-1-oxo-tetrahydro-thiopyran-4-ol (cis sulfoxide),

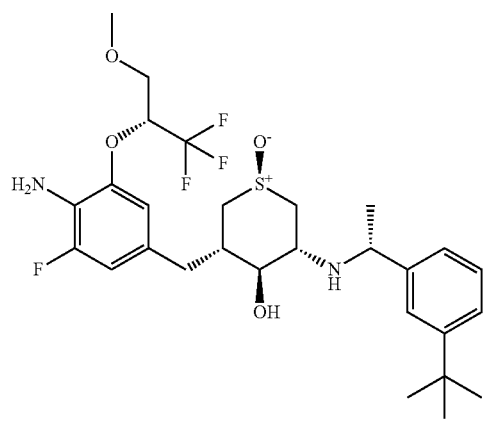

(1R,3S,4S,5R)-3-[4-amino-3-fluoro-5-((R)-2,2,2-trifluoro-1-methoxymethyl-ethoxy)-benzyl]-5-(3-isopropyl-5-methoxy-benzylamino)-1-oxo-tetrahydro-thiopyran-4-ol (cis sulfoxide),

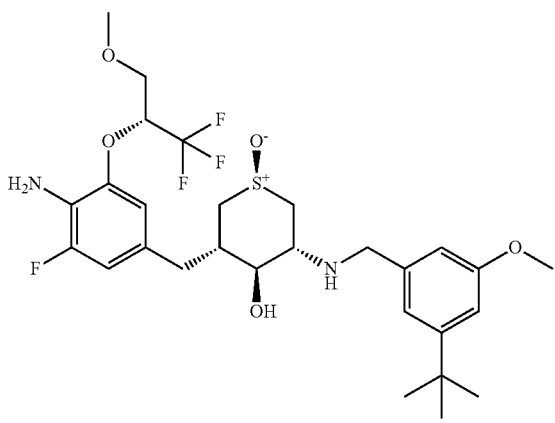

(1R,3S,4S,5R)-3-[4-amino-3-fluoro-5-((R)-2,2,2-trifluoro-1-methoxymethyl-ethoxy)-benzyl]-5-[(R)-1-(3-tert-butyl-phenyl)-ethylamino]-1-oxo-tetrahydro-thiopyran-4-ol (cis sulfoxide),

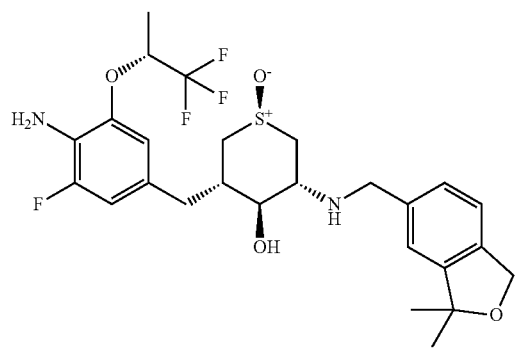

(1R,3S,4S,5R)-3-[4-amino-3-fluoro-5-((S)-2,2,2-trifluoro-1-methyl-ethoxy)-benzyl]-5-[(3,3-dimethyl-1,3-dihydro-isobenzofuran-5-ylmethyl)-amino]-1-oxo-hexahydro-thiopyran-4-ol (cis sulfoxide),

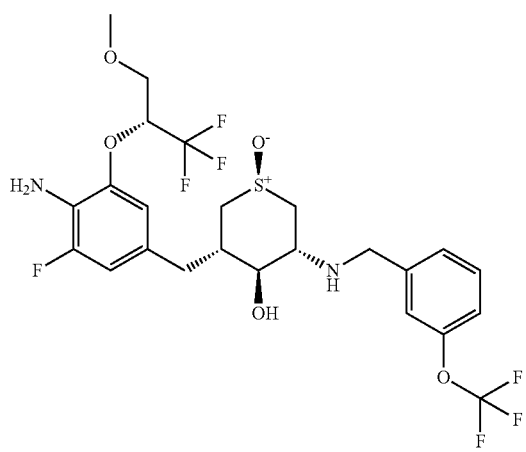

(1R,3S,4S,5R)-3-[4-amino-3-fluoro-5-((R)-2,2,2-trifluoro-1-methoxymethyl-ethoxy)-benzyl]-1-oxo-5-(3-trifluormethoxy-benzylamino)-tetra-hydro-thiopyran-4-ol (cis sulfoxide),

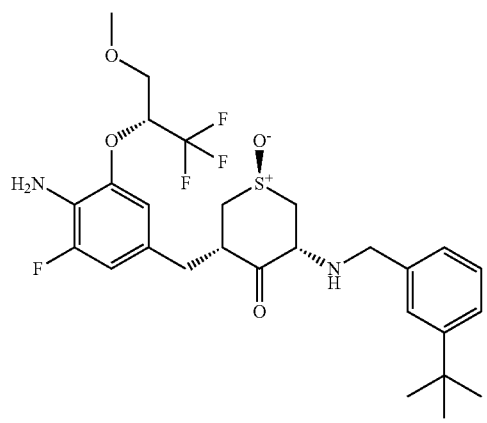

(1R,3S,5R)-3-[4-amino-3-fluoro-5-((R)-2,2,2-trifluoro-1-methoxymethyl-ethoxy)-benzyl]-5-(3-tert-butyl-benzylamino)-1-oxo-tetrahydro-thiopyran-4-one; and
the compounds listed in the following five tables where the asterisk denotes the point of attachment of R, $R_1$ and $R_2$:

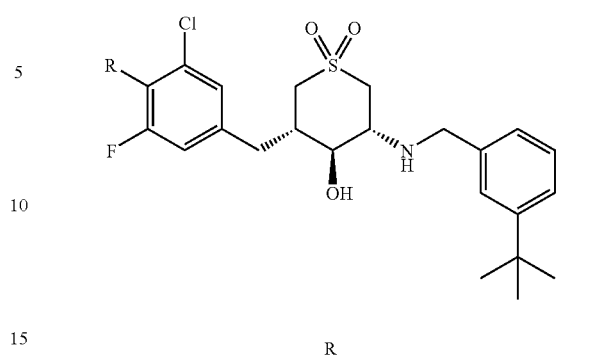

| R |
|---|

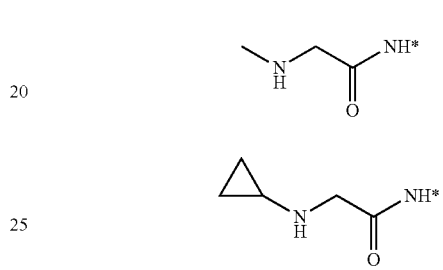

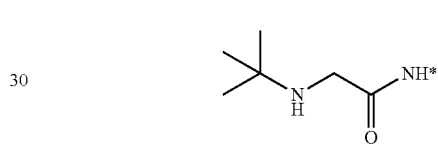

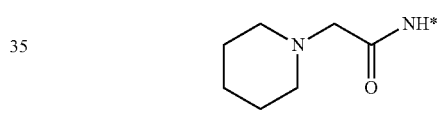

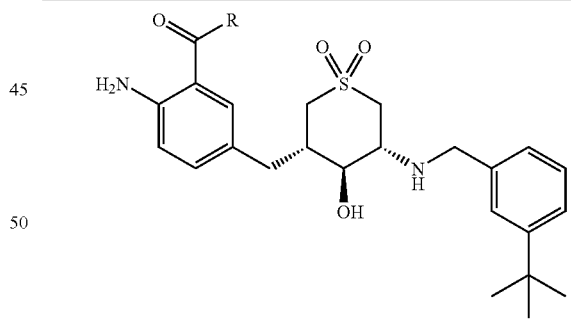

| R |
|---|

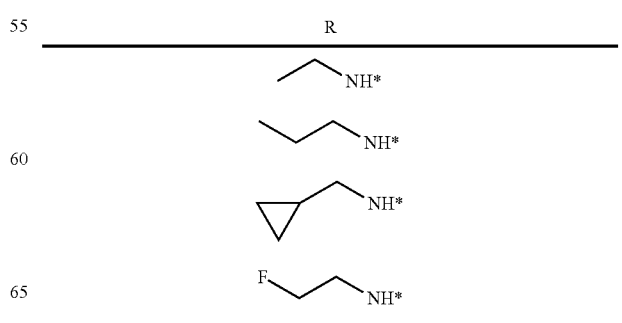

| 101 -continued | 102 |
|---|---|
| 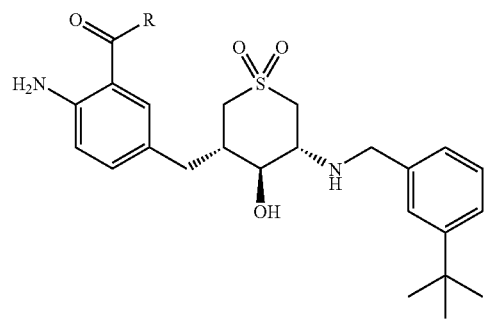 | 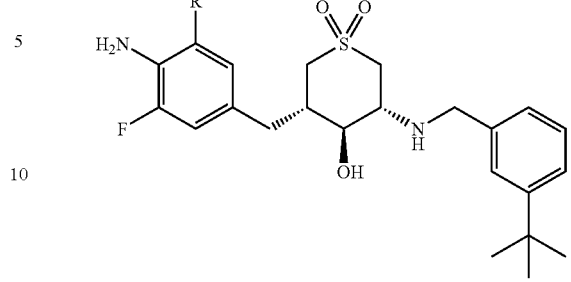 |
| R | R |
| 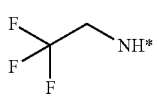 | 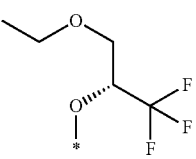 |
| 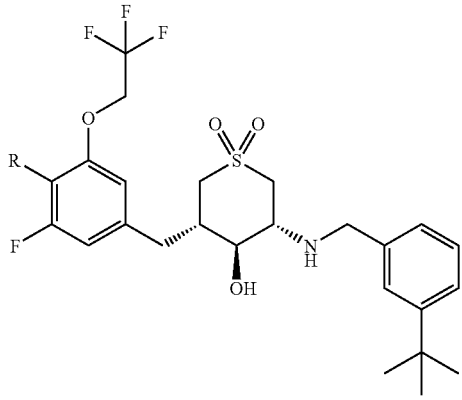 | 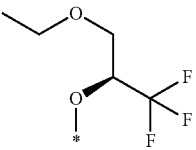 |
| R | 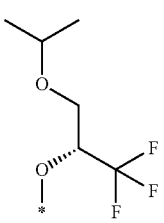 |
| 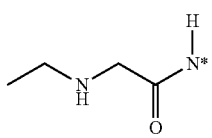 | 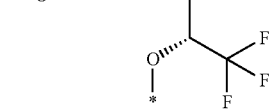 |
| 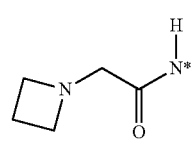 | 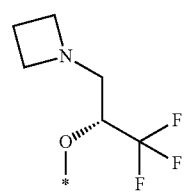 |
| 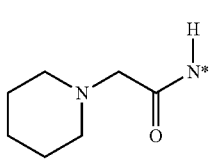 | |

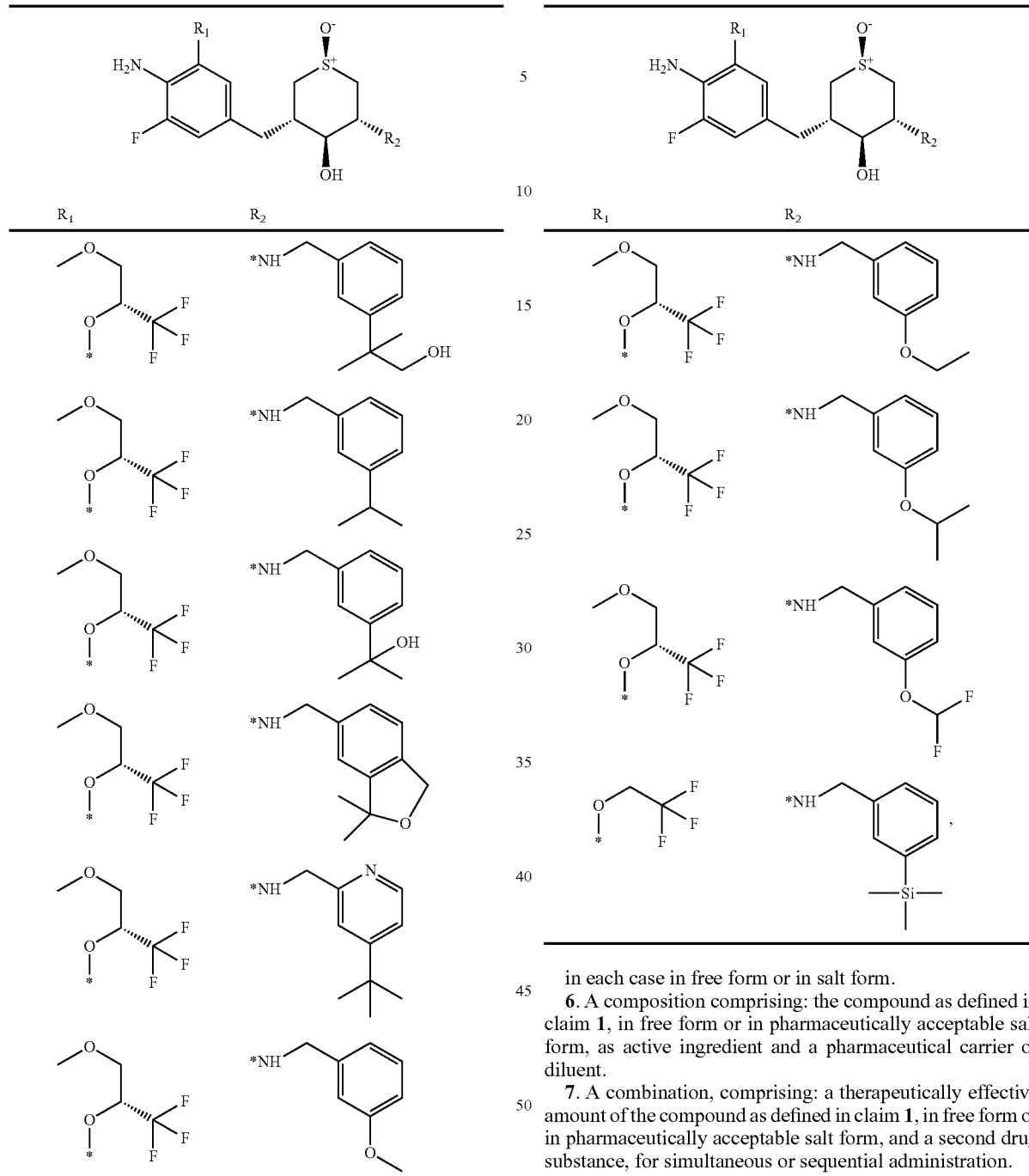

in each case in free form or in salt form.

6. A composition comprising: the compound as defined in claim 1, in free form or in pharmaceutically acceptable salt form, as active ingredient and a pharmaceutical carrier or diluent.

7. A combination, comprising: a therapeutically effective amount of the compound as defined in claim 1, in free form or in pharmaceutically acceptable salt form, and a second drug substance, for simultaneous or sequential administration.

* * * * *